US008535684B2

(12) United States Patent
Kinch et al.

(10) Patent No.: US 8,535,684 B2
(45) Date of Patent: Sep. 17, 2013

(54) METHODS OF INHIBITING HIV INFECTIVITY

(75) Inventors: Michael S. Kinch, Laytonsville, MD (US); Michael Goldblatt, McLean, VA (US); Wu-Bo Li, North Potomac, MD (US); Douty Bamba, Randallstown, MD (US); Shaojing Chang, Rockville, MD (US); Huosheng Chen, Germantown, MD (US); Zenbework Fesseha, Columbia, MD (US); Manu Kohli, Dunn Loring, VA (US); Hanwen Mao, Annandale, VA (US); Heather Thi Thu Ung-Medoff, Gaithersburg, MD (US); Ke Weng, Gaithersburg, MD (US)

(73) Assignee: Functional Genetics, Inc., Gaithersburg, MD (US)

(*) Notice: Subject to any disclaimer, the term of this patent is extended or adjusted under 35 U.S.C. 154(b) by 187 days.

(21) Appl. No.: 12/652,877

(22) Filed: Jan. 6, 2010

(65) Prior Publication Data
US 2010/0183628 A1 Jul. 22, 2010

Related U.S. Application Data

(60) Provisional application No. 61/142,664, filed on Jan. 6, 2009, provisional application No. 61/153,012, filed on Feb. 17, 2009, provisional application No. 61/158,015, filed on Mar. 6, 2009, provisional application No. 61/160,737, filed on Mar. 17, 2009, provisional application No. 61/178,112, filed on May 14, 2009, provisional application No. 61/180,457, filed on May 22, 2009.

(51) Int. Cl.
*A61K 39/21* (2006.01)
*A61K 49/00* (2006.01)
*A61K 39/395* (2006.01)
*A61K 39/42* (2006.01)

(52) U.S. Cl.
USPC .... 424/208.1; 424/9.1; 424/130.1; 424/148.1

(58) Field of Classification Search
None
See application file for complete search history.

(56) References Cited

U.S. PATENT DOCUMENTS

| 5,272,071 | A | 12/1993 | Chappel |
| 5,679,523 | A | 10/1997 | Li et al. |
| 7,745,148 | B2 | 6/2010 | Duan et al. |
| 7,981,410 | B2 | 7/2011 | Duan et al. |
| 2003/0236210 | A1* | 12/2003 | Geng ............ 514/44 |
| 2008/0124341 | A1 | 5/2008 | Duan et al. |
| 2010/0286248 | A1 | 11/2010 | Li et al. |

FOREIGN PATENT DOCUMENTS

| WO | WO 2004/020582 A2 | 3/2004 |
| WO | WO 2008/133711 A2 | 11/2008 |
| WO | WO 2008/140571 A2 | 11/2008 |

OTHER PUBLICATIONS

Anand et al., Concise Communication A novel role for Slit2/Robo1 axis in modulating HIV-1 replication in T cells, 2011, AIDS, vol. 25, pp. 2105-2111.*
Liu et al., Extracellular Ig domains 1 and 2 of Robo are important for ligand (Slit) binding, 2004, Molecular and Cellular Neuroscience, vol. 26, pp. 232-240.*
Rosenberg, Putting the brakes on leukocyte chemotaxis: an interview with Dr. Ramesh K. Ganju, 2007, Journal of Leukocyte Biology, vol. 82, p. 1 and 2.*
Reeves, et al., "Emerging Drug Targets for Antiretroviral Therapy", Drugs, 2005: 65(13): 1747-1766.
Thompson, et al., "Mortality Associated with Influenza and Respiratory Syncytial Virus . . . " JAMA, Jan. 8, 2003, vol. 289, No. 2.
Garrus, et al., "Tsg101 and the Vacuolar Protein Sorting Pathwa are Essential for HIV-1 Budding", Cell, vol. 107, 55-65, Oct. 5, 2001.
Grant, et al., "Time Trends in Primary HIV-1 Drug Resistance Among Recently Infected Persons", JAMA, Jul. 10, 2002, vol. 288, No. 2.
Liu, et al., "Homozygous Defect in HIV-1 Coreceptor Accounts for Resistance of . . . " Cell, vol. 86, 367-377, Aug. 9, 1996.
Richman, et al., "The Prevalence of Antiretroviral Drug Resistance in the United States", AIDS, 2004, 18:1393-1401.
Wei, et al., "Emergence of Resistant Human Immunodeficiency Virus Type 1 in . . . " Antimirobial Agents and Chemotherapy, Jun. 2002, pp. 1896-1905, 2002.
Wong, et al., "Slit Proteins: Molecular Guidance Cues for Cells Ranging from . . . ", Current Opinion in Genetics & Development 2002, 12:583-591.
Wu, et al., "The Neuronal Repellent Slit Inhibits Leukocyte Chemotaxis Induced by . . . " Nature, vol. 410, Apr. 19, 2001.
Reiske, et al., "Identification of Annexin A13 as a Regulator of Chemotherapy Resistance . . . " Analytical and Quantitative Cytology and Histology p. 1-9, 2010.
Yang, et al., "Targeting the Ubiquitin-Proteasome System for Cancer Therapy", Cancer Sci. Jan. 2009, vol. 100, No. 1.
MMWR, Trends in HIV/AIDS Diagnoses Among Men Who Have Sex with Men—33 States, 2001-2006, Morbidity and Mortality Weekly Report, Jun. 27, 2008, vol. 57, No. 25.
MMWR, "Interim Within-Season Estimate of the Effectiveness of Trivalent Inactivated . . . ", Morbidity and Mortality Weekly Report, Apr. 18, 2008, vol. 57, No. 15.

(Continued)

*Primary Examiner* — Benjamin P Blumel
(74) *Attorney, Agent, or Firm* — Steven B. Kelber; Berenato & White, LLC

(57) ABSTRACT

A method for identifying host genes and encoded proteins for potential targets for therapeutic intervention employs a Gene Search Vector that is either lentivirus or MMLV-based, and can be used to interrogate an entire cell genome without prior knowledge of the genomic sequence. This Random Homozygous Gene Perturbation (RUGP) technique is rapidly verifiable and is used to identify potential host targets for intervention for influenza, HIV and other viral infections. Using Thermal Assymetric Interlaced (TAIL)-PCR, the period for identification of promising targets is reduced from months to weeks or less. Specific targets including PTCH1, Robo1 and Nedd4 are reviewed in detail.

4 Claims, 20 Drawing Sheets

(56) References Cited

OTHER PUBLICATIONS

Luscher-Mattli, "Influenza Chemotherapy: A Review of the Present State of Art . . . ", Arch. Virol. (2000) 145:2233-2248.
Tan, et al., "Systems Biology and the Host Response to Viral Infection", Nature Biotechnology, vol. 25, No. 12, Dec. 2007.
Fox, "Antivirals Become a Broader Enterprise", Nature Biotechnology, vol. 25, No. 12, Dec. 2007.
Lombardo, et al., "Gene Editing in Human Stem Cells Using Zinc Finger Nucleases and Integrase-Defective . . . ", Nature Biotechnology, vol. 25, No. 11, Nov. 2007.
Ahlquist, et al., "Host Factors in Positive-Strand RNA Virus Genome Replication", Journal of Virology, Aug. 2003, p. 8181-8186.
Hao, et al., "Drosophila RNAi Screen Identifies Host Genes Important for Influenza Virus Replication", Nature, vol. 454, Aug. 14, 2008.
Shattock, et al., "Inhibiting Sexual Transmission of HIV-1 Infection", Nature Reviews, Microbiology, vol. 1, Oct. 2003.
Ataergin, et al., "New Generation Pharmacotherapy in Elderly Multiple Myeloma Patients", Expert Opin. Pharmacother. (2009) 10:(1).
Campos, "Anti-Epidermal Growth Factor Receptor Strategies for Advanced Breast Cancer", Cancer Investigation, 26:757-768, 2008.
Gottesman, et al., "The Molecular Basis of Multidrug Resistance in Cancer: The Early Years of P-Glycoprotein Research", FEBS Letters, 580 (2006) 998-1009.
Huesken, et al., "Design of a Genome-Wide siRNA Library Using an Artificial Neural Network", Nature Biotechnology, vol. 23, No. 8, Aug. 2005.
Li, et al., "tsg101: A Novel Tumor Susceptibility Gene Isolated by Controlled Homozygous Functional . . . ", Cell, vol. 85, 319-329, May 3, 1996.
Lih, et al., "Tsr1: A Transcriptional Regulator of Thrombospondin-1 That Modulates Cellular Sensitivity to Taxanes", Genes Dev. 2006 20:1082-2095.
Liu, et al., "Efficient Isolation and Mapping of Arabidopsis thaliana T-DNA Insert Junctions by Thermal Asymmetric Interlaced PCR", The Plant Journal (1995) 8:(3) 457-463.
Madarnas, et al., "Adjuvant/Neoadjuvant Trastuzumab Therapy in Women with HER-2/neu-Overexpressing Breast . . . ", Cancer Treatment Reviews (2008) 34, 539-557.
Pytel, et al, "Tyrosine Kinase Blockers: New Hope for Successful Cancer Therapy", Anticancer Agents Med. Chem., Jan. 9, 2009(1):66-76.
U.S. Appl. No. 61/142,664, filed Jan. 6, 2009, Sui, et al.
U.S. Appl. No. 61/153,012, filed Feb. 17, 2009, Li, et al.
U.S. Appl. No. 61/158,015, filed Mar. 6, 2009, Goldblatt, et al.
U.S. Appl. No. 61/160,737, filed Mar. 17, 2009, Kinch, et al.
U.S. Appl. No. 61/178,112, filed May 14, 2009, Chen, et al.
U.S. Appl. No. 61/180,457, filed May 22, 2009, Li, et al.
Levine, et al., "Conversion of Lytic to Persistent Alphavirus Infection by the bcl-2 Cellular Oncogene", Nature, vol. 361, Feb. 25, 1993.
Hinshaw, et al., "Apoptosis: a Mechanism of Cell Killing by Invluenza A and B Viruses", Journal of Virology, Jun. 1994, pp. 3667-3673.
Mishra, et al., "Activation of JNK-Dependent Pathway is Requirement for HIV Viral Protein . . . ", Journal of Biological Chemistry, vol. 282, No. 7, Feb. 16, 2007.
Wada, et al., "Amino-Terminal Fragment of Urokinase-Type Plasminogen Activator . . . " Biochemical and Biophysical Research Communications 284, 346-351 (2001).
Martinez, et al., "Distinct Gene Subsets are Induced at Different Time Points after Human . . . ", Journal of General Virology (2007) 88: 570-581.

JAMA, "Interim Within-Season Estimate of the Effectiveness of Trivalent Inactivated Influenza . . . ", JAMA 2008:299(20): 2381-2384.
Chen, et al., "Mechanisms for Enveloped Virus Buding: Can Some Viruses do without an ESCRT?", Virology 372 (2008) 221-232.
Kleinman, et al., "Sequence- and Target-Independent Angiogenesis Suppression . . . " Nature, vol. 452, Apr. 3, 2008.
Lamb, et al., "Death by Inflenza Virus Protein", Nature Medicine, vol. 7, No. 12, Dec. 2001.
Ong, et al., Neuraminidase Inhibitor (NAI) Development, JID 2007:196 (Jul. 15).
Brass, et al., "Identification of Host Proteins Required for HIV Infection Through a Functional Genomic Screen", Science, vol. 319, Feb. 15, 2008.
Konig, et al., "Global Analysis of Host-Pathogen Interactions that Regulate Early-STage HIV-1 Replication", Cell 135, 49-60, Oct. 3, 2008.
Krishnan, et al., "RNA Interference Screen for Human Genes Associates with West Nile Virus Infection", Nature, vol. 455, Sep. 11, 2008.
Lu, et al., "EST-Based Genome-Wide Gene Inactivation Identifies ARAP3 as a Host Protein Affecting . . . " PNAS, Dec. 7, 2004, vol. 101, No. 49, 17246-17251.
Ge, et al., "RNA Interference of Influenze Virus Production by Directly Targeting mRNA for Degradation . . . ", PNAS, Mar. 4, 2003, vol. 100, No. 5 2718-2723.
Mitchell, et al., "Retroviral DNA Integration: ASLV, HIV, and MLV Show Distinct Target . . . ", PLOS Biology, Aug. 2004, vol. 2, Issue 8.
Mi, et al., "The PANTHER Database of Protein Families, Subfamilies, . . . " Nucleic Acids Research, vol. 33, Database Issue, 2005.
Ndolo, et al., "Expression of Simian Immunodeficiency Virus Nef Protein in CD4 . . . ", Virology 353 (2006) 374-387.
Baldwin, et al., "Molecular Cloning and Expression of Receptor Peptides That Block . . . " Biochemical and Biophysical Research Communications 219, 668-673 (1996).
Howell, et al., Mutation of a Ubiquitously Expressed Mouse Transmembrane Protein . . . Genetics 176:699-707 (Feb. 2007).
Yu, et al., "Self-Inactivating Retroviral Vectors Designed for Transfer of Whole Genes into Mammalian Cells", Proc. Natl Acad. Sci May 1996; 83(10):3194-8.
Sui, et al., "The Use of Random Homozygous Gene Perturbation to Identify Novel Host-Oriented Targets for Influenze", Virology 387 (2009) 473-481.
Prasad, et al., "Pivotal Advance: Slit-2/Robo-1 Modulates the CXCL12/CXCR4-Induced Chemotaxis of TCells", Journal of Leukocyte Biology, vol. 82, Sep. 2007.
Pillai, et al., "Integration Site Analysis in Transgenic Mice by Thermal Asymmetric Interlaced (TAIL)-PCR: Segreating . . . ", Transgenic Res. (2008) 17:749-754.
Cui, et al., "Gene Expression of Xox5a, 5b, or 6b1 and THeir Roles in Preimplantation Mouse Embryos", Biology of Reproduction 74, 601-610 (2006).
Beckett, et al., "Identifying Stromal-Epithelial Interactions in the Mammary Gland Through Genome-Wide . . . ", Cancer Research, Jan. 15, 2009; vol. 69, Issue 2, Supplement 1.
Poli, "PRO-140 (Progenics)", IDrugs, Sep. 4, 2001(9) 1068-71.
Ludwig, et al., "A Fatal Relationship—Influenza Virus Interactions with the Host Cell", Viral Immunology, 1999, 12(3): 175-196.
Wheeler, et al., "Assessing Theoretical Risk and Benefit Suggested by Genetic Association Studies . . . ", Antiviral Therapy 12:233-245, 2007.
Mello, et al., "Revealing the World of RNA Interference", Nature, vol. 431, Sep. 16, 2009.

\* cited by examiner

| | Era of Drug Screening | Era of Targeted Intervention | Omics Based Target Discovery | Function-First Target Discovery |
|---|---|---|---|---|
| Function-First Screening | Yes | No | No | Yes |
| Target Identity Known? | No (but later deduced) | Yes | Yes | Yes |
| Breadth of Target Types | Broad | Narrow | Broad | Broad |
| Target Link to Disease | Direct | Direct | Correlative | Direct |
| Enabling Technologies | -HTS Screening<br>-Compound Libraries | -Oncogene Discovery<br>-Mechanistic Understanding | -Genome Knowledge<br>-Omics Technology | -siRNA<br>-RHGP |

FIG. 1

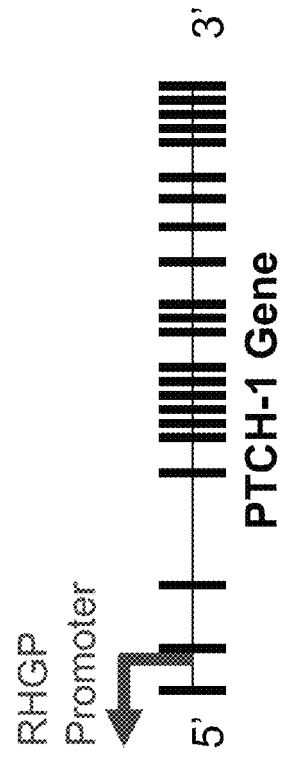
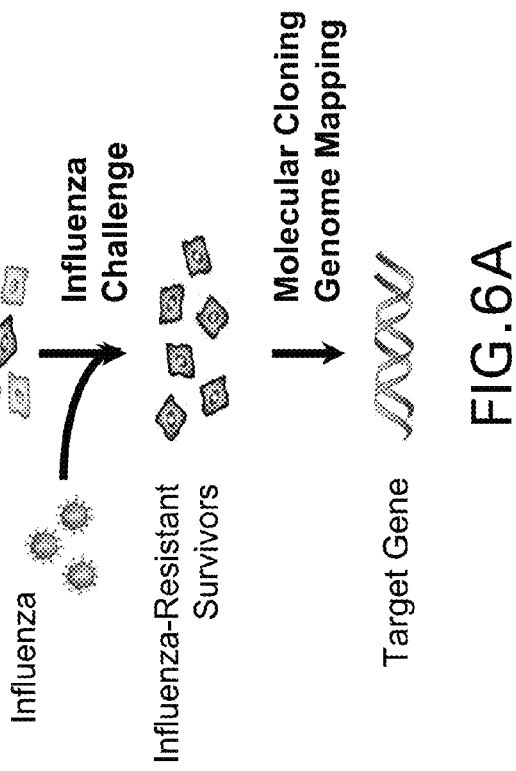
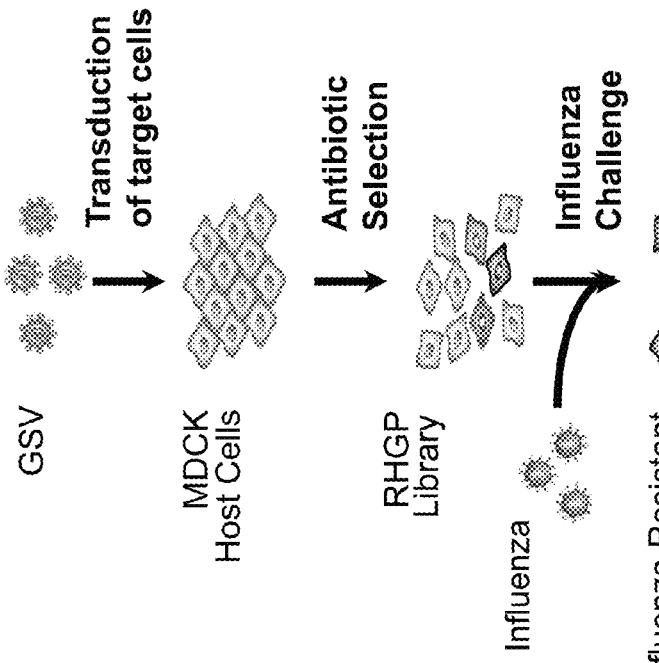

Classification by Biological Process

| Biological Process | RHGP-Influenza Frequency (%) | Human Genes (%) |
|---|---|---|
| Protein metabolism and modification | 22 | 12 |
| Nucleoside, nucleotide and nucleic acid metabolism | 26.4 | 13.1 |
| Signal transduction | 19.8 | 13.4 |
| Intracellular protein traffic | 9.9 | 4.0 |
| Development process | 12.1 | 8.5 |
| Transport | 11 | 5.1 |
| Cell structure and modility | 9.9 | 4.5 |
| Biological process unidentified | 22 | 44 |

Classification by Molecular Function

| Molecular Function | RHGP-Influenza Frequency (%) | Human Genes (%) |
|---|---|---|
| Nucleic acid binding | 23.1 | 11.2 |
| Kinase | 8.8 | 2.7 |
| Membrane traffic protein | 6.6 | 1.3 |
| Hydrolase | 6.6 | 2.9 |
| Ligase | 5.5 | 1.8 |
| Transferase | 6.6 | 3.5 |
| Select regulatory molecule | 5.5 | 4.7 |
| Transcription factor | 8.8 | 8.1 |
| Molecular function unclassified | 17.6 | 43 |

| GENE | POSITION | INSERTION SITE | ORIENTATION | DESCRIPTION | LOCATION | SURFACE EXPOSED? | EFFECT ON METASTASIS (ATTACHMENT) | DETAILS |
|---|---|---|---|---|---|---|---|---|
| DPY19L1 | 7p14.3 | intron 3 | sense | dpy-19-like 1 (C. elegans) | predicted multipass membrane protein | predicted | promotes | unknown function, though in C. elegans, DPY-19 is involved in orientation of migrating cells |
| PVR | 19q13.31 | intron 2 | antisense | poliovirus receptor (PVR), transcript variant 1 | transmembrane glycoprotein | yes | promotes | Poliovirus receptor that mediates attachment to vitronectin in ECM |
| USP11 | Xp11.3 | intron 1 | antisense | ubiquitin specific peptidase 11 | nucleus and cytoplasm | no | promotes | This protein has been demonstrated to regulate ubiquitination of the IKKalpha-p53 pathway, as well as BRCA2. |
| KIAA0753 | 17p13.2 | intron 14 | sense | KIAA0753 | N/A | N/A | promotes | N/A |
| EFEMP1 | 2p16.1 | intron 5 | antisense | EGF-containing fibulin-like extracellular matrix protein 1 (EFEMP1), transcript variant 2 | plasma membrane | yes | promotes | This protein is localized at basal membranes and regulated cell to cell and cell to matrix communication. It is thought to be an angiogenesis antagonist. Decreased expression correlates with higher incidence of breast cancer. Promoter hypermethylation is seen with lung cancer. In contrast, pancreatic cancer samples seem to show an upregulation of EFEMP1 (fibulin-3). |

FIG 16A

| | | | | | |
|---|---|---|---|---|---|
| ITPKC | 19q13.2 | intron 1 | antisense | inositol 1,4,5-trisphosphate 3-kinase C | cytoplasm | no | promotes | Inositol 1,4,5-trisphosphate 3-kinase (ITPK) modulates calcium homeostasis. ITPKC is associated with Kawasaki Disease, a pediatric systemic vasculitis. The gene is thought to be involved in the NFAT pathway for inhibition of T cell activation. |
| DGCR8 | 22q11.21 | intron 9 | sense | DiGeorge syndrome critical region gene 8 | nucleus | no | inhibits | Part of Microprocessor complex with Drosha, and required for miRNA maturation. Loss of miRNA synthesis associated with tumor progression. |
| SGPP2 | 2q36.1 | intron 2 | antisense | sphingosine-1-phosphate phosphatase 2 | endoplasmic reticulum | no | inhibits | SGPP2 appears to be a pro-inflammatory modulator, having NFkB binding sites in its promoter. |

FIG. 16B

SEQUENCE LISTING

```
<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: Forward primer for lentivirus RHGP vectors

<400> SEQUENCE: 1
cagcaagccg agtcctgcgt cg                                              22

<210> SEQ ID NO 2
<211> LENGTH: 22
<212> TYPE: DNA
<213> ORGANISM: Artificial Sequence
<220> FEATURE:
<223> OTHER INFORMATION: Forward primer for lentivirus RHGP vectors

<400> SEQUENCE: 2
tcgagagagc tcctctggtt tc                                              22

<210> SEQ ID NO 3
```

```
<211> LENGTH: 22
<212> TYPE: DNA
<213> ORGANISM: Artificial Sequence
<220> FEATURE:
<223> OTHER INFORMATION: Forward primer for lentivirus RHGP vectors

<400> SEQUENCE: 3
gtccctgttc gggcgccact gc                                                22

<210> SEQ ID NO 4
<211> LENGTH: 16
<212> TYPE: DNA
<213> ORGANISM: Artificial Sequence
<220> FEATURE:
<223> OTHER INFORMATION: Reverse primer for lentivirus RHGP vectors
<221> NAME/KEY: misc_feature
<222> LOCATION: 1, 11
<223> OTHER INFORMATION: n = A,T,C or G

<400> SEQUENCE: 4
ngtcgaswga nawgaa                                                       16

<210> SEQ ID NO 5
<211> LENGTH: 16
<212> TYPE: DNA
<213> ORGANISM: Artificial Sequence
<220> FEATURE:
<223> OTHER INFORMATION: Reverse primer for lentivirus RHGP vectors
<221> NAME/KEY: misc_feature
<222> LOCATION: 5, 10
<223> OTHER INFORMATION: n = A,T,C or G

<400> SEQUENCE: 5
tgwgnagsan casaga                                                       16

<210> SEQ ID NO 6
<211> LENGTH: 16
<212> TYPE: DNA
<213> ORGANISM: Artificial Sequence
<220> FEATURE:
<223> OTHER INFORMATION: Reverse primer for lentivirus RHGP vectors
<221> NAME/KEY: misc_feature
<222> LOCATION: 5, 10
<223> OTHER INFORMATION: n = A,T,C or G

<400> SEQUENCE: 6
agwgnagwan cawagg                                                       16

<210> SEQ ID NO 7
<211> LENGTH: 16
<212> TYPE: DNA
<213> ORGANISM: Artificial Sequence
<220> FEATURE:
<223> OTHER INFORMATION: Reverse primer for lentivirus RHGP vectors
<221> NAME/KEY: misc_feature
<222> LOCATION: 5, 10, 13
<223> OTHER INFORMATION: n = A,T,C or G

<400> SEQUENCE: 7
sttgntastn ctntgc                                                       16

<210> SEQ ID NO 8
<211> LENGTH: 15
<212> TYPE: DNA
<213> ORGANISM: Artificial Sequence
<220> FEATURE:
<223> OTHER INFORMATION: Reverse primer for lentivirus RHGP vectors
<221> NAME/KEY: misc_feature
<222> LOCATION: 1
<223> OTHER INFORMATION: n = A,T,C or G
```

<400> SEQUENCE: 8
ntcgastwts gwgtt                                                15

<210> SEQ ID NO 9
<211> LENGTH: 16
<212> TYPE: DNA
<213> ORGANISM: Artificial Sequence
<220> FEATURE:
<223> OTHER INFORMATION: Reverse primer for lentivirus RHGP vectors
<221> NAME/KEY: misc_feature
<222> LOCATION: 5, 10, 13
<223> OTHER INFORMATION: n = A,T,C or G

<400> SEQUENCE: 9
wgtgnagwan canaga                                               16

<210> SEQ ID NO 10
<211> LENGTH: 24
<212> TYPE: DNA
<213> ORGANISM: Artificial Sequence
<220> FEATURE:
<223> OTHER INFORMATION: Forward primer for MMLV RHGP vectors

<400> SEQUENCE: 10
ctgcatcctg ggatcaaagc cata                                      24

<210> SEQ ID NO 11
<211> LENGTH: 24
<212> TYPE: DNA
<213> ORGANISM: Artificial Sequence
<220> FEATURE:
<223> OTHER INFORMATION: Forward primer for MMLV RHGP vectors

<400> SEQUENCE: 11
cgtgaattgc tgccctctgg ttat                                      24

<210> SEQ ID NO 12
<211> LENGTH: 24
<212> TYPE: DNA
<213> ORGANISM: Artificial Sequence
<220> FEATURE:
<223> OTHER INFORMATION: Forward primer for MMLV RHGP vectors

<400> SEQUENCE: 12
cgtcctctag cgatgataag ctgt                                      24

<210> SEQ ID NO 13
<211> LENGTH: 21
<212> TYPE: DNA
<213> ORGANISM: Artificial Sequence
<220> FEATURE:
<223> OTHER INFORMATION: siRNA NP-1496 homologues for PTCH 1

<400> SEQUENCE: 13
ggaucuuauu ucuucggagu u                                         21

<210> SEQ ID NO 14
<211> LENGTH: 480
<212> TYPE: DNA
<213> ORGANISM: Artificial Sequence
<220> FEATURE:
<223> OTHER INFORMATION: PTCH1
<221> NAME/KEY: misc_feature
<222> LOCATION: 65, 87, 90, 126, 161, 184, 192, 222, 227, 244, 245, 278,
      319, 340, 341, 344, 350, 402, 406, 451
<223> OTHER INFORMATION: n = A,T,C or G

```
<400> SEQUENCE: 14
taaacgtaaa aagtagccaa gcgcacgggg gaagggcccc ggccggcgca ggcaggggtc      60
ccggntgggc tgcggctgat cccggcngcn gcgtgatctc ggcgctggcc gcatgccccg     120
gcgggncccc gtctgggtgc tcgccttccc cggattccac ncattgcagc gagcctcgta     180
aacncaatga anccggccgc ttggcagacc cgcaccgcgg anttaangtg gcaatttgtt     240
tacnnctttc cctctccccc caggctctgg gaagaggnga ctcaaaaact gaaaaggaag     300
aggggagatg ccctctttna aggataattt ttaagggggn nganatttcn agctcagcaa     360
aagcaaaacc ggatgccaaa aaaggaaacc acctttattt cngctncctc ccccccttcc     420
atctctccgc ctctctccac tccgctttcc nccctcaaaa gatgttaaaa aaatgtggca     480
```

METHODS OF INHIBITING HIV INFECTIVITY

PRIORITY DATA AND INCORPORATION BY REFERENCE

This application claims benefit of priority to U.S. Provisional Patent Application No. 61/142,664, filed Jan. 6, 2009; U.S. Provisional Patent Application No. 61/153,012, filed Feb. 17, 2009; U.S. Provisional Patent Application No. 61/158,015, filed Mar. 6, 2009; U.S. Provisional Patent Application No. 61/160,737, filed Mar. 17, 2009; U.S. Provisional Patent Application No. 61/178,112, filed May 14, 2009 and U.S. Provisional Patent Application No. 61/180,457, filed May 22, 2009; all of which are incorporated by reference in their entirety.

BACKGROUND OF THE INVENTION

Field of the Invention

The present invention relates to the use of a gene search vector system (GSV) to identify therapeutic host targets by Random Homozygous Gene Perturbation (RHGP) coupled with identification of the targets spotted through a process referred to as Thermal Assymetric Interlaced PCR, or TAIL-PCR. The combination of RHGP with TAIL PCR is referred to throughout this application as RHGP.

The sequencing of the human genome has not brought, immediately, the cascade of therapeutic targets for treatment once anticipated. Knowing the existence of a gene sequence does not allow one, without more, to characterize the phenotype(s) that gene or gene system is responsible for, or how the gene mediates the cell's ongoing evolution. And yet, host target identification has become a field of increasing importance for many researchers. Viral diseases, in particular, have challenged man's ingenuity in developing methods of preventing and treating mammals, and particularly humans, challenged with viral invaders. Although this invention has broad applicability, the focus in this application is the utility of RHGP as a device to identify host targets for therapeutic intervention.

Viruses have frustrated the ability to develop effective therapeutics in part because of their ability to mutate away from the effectiveness of a drug that targets the virus. Viruses also have a broad palette of differential actions available to them—they can be rapid invaders, like Influenza, or the viral takeover of the infected cell's machinery can be slow and delayed over time, like HIV. As an alternative to invader targeting, Functional Genetics, Inc, the assignees of this application, has led the paradigm shift away from designing therapeutics that target the virus, and developed both antibody and small molecule therapies that target host proteins, such as TSG101 and other host proteins. By targeting host proteins, the pressure on the virus to mutate away is reduced. The virus is allowed to infect a given cell, but by denying the virus access to host proteins essential for its life cycle, the spread of the virus from cell to cell is prevented.

In order to further the identification of potential host therapeutic proteins and genes, a sort of advanced search engine is required:

The inquiry is a basic one—does the gene in question, and/or the product it encodes, confer resistance of some sort against a viral invader. The inquiry can be in essence a yes/no inquiry. In other situations, with other diseases, the inquiry may be different. Thus, RHGP may be used to identify a human gene the expression of which correlates with the plaque formation phenotype found in Alzheimer patients. Those results are reported in U.S. patent application Ser. No. 12/566,951, filed Sep. 25, 2009. A variety of techniques have been developed over the years to identify host targets implicated in various diseases. An exemplary technology is competing RNA interference (RNAi). See, e.g., Nature, Revealing the World of iRNA, 431, pp. 338-342 (September, 2004) incorporated herein by reference. Small interfering (siRNA) has received a great deal of attention for the generation of genome-wide siRNA libraries to assist in target discovery. Becket et al, Cancer Research, 69(2), (2009). These methods do require some prior knowledge of the target to be identified, and the relevant genome. The past decade has witnesses remarkable advances in the diagnosis and treatment of many life threatening cancers. Much of the progress builds upon understanding of fundamental mechanisms that control cancer cell behavior. Such knowledge formed the foundation for the rationale design of targeted therapies against molecular changes and regulatory mechanisms that are selectively utilized by cancer cells. Prominent successes include targeting HER2 on breast cancer cells with trastuzumab (Herceptin®), proteosomes in multiple myeloma with bortezomib (Velcade®) and EGFR on non-small cell lung cancer cells with gefitinib (Iressa®) (Ataergin et al., 2009; Campos, 2008; Madarnas et al., 2008; Pytel et al., 2009; Yang et al., 2009). However, most rationally-designed therapies under development today are focused upon a relatively narrow set of targets. This emphasis logically follows from increased knowledge about these targets and commercial success with existing drugs that stimulate fast-follower drugs targeting the same or similar molecules. Nonetheless, these trends can stifle breakthroughs that might otherwise arise from under-appreciated or unknown targets or mechanisms. The key therefore is to develop novels means of identifying targets that critically control cancer cells drug sensitivity, metastatic potential and other hallmarks of the disease's pathophysiology.

The past decade has witnessed remarkable advances in the diagnosis and treatment of many life-threatening cancers. Much of the progress builds upon understanding of fundamental mechanisms that control cancer cell behavior. Such knowledge formed the foundation for the rationale design of targeted therapies against molecular changes and regulatory mechanisms that are selectively utilized by cancer cells. Prominent successes include targeting HER2 on breast cancer cells with trastuzumab (Herceptin®), proteosomes in multiple myeloma with bortezomib (Velcade®) and EGFR on non-small cell lung cancer cells with gefitinib (Iressa®) (Ataergin et al., 2009; Campos, 2008; Madarnas et al., 2008; Pytel et al., 2009; Yang et al., 2009). However, most rationally-designed therapies under development today are focused upon a relatively narrow set of targets. This emphasis logically follows from increased knowledge about these targets and commercial success with existing drugs that stimulate fast-follower drugs targeting the same or similar molecules. Nonetheless, these trends can stifle breakthroughs that might otherwise arise from under-appreciated or unknown targets or mechanisms. The key therefore is to develop novels means of identifying targets that critically control cancer cells drug sensitivity, metastatic potential and other hallmarks of the disease's pathophysiology.

In early exploration of the genomes of relatively simple creatures, such as bacteria, the presence of only a single copy of DNA, and therefore, a single allele of a target gene, made for quick identification of target genes. "Knocking out" the gene, by targeted recombination (homologous recombination) allowed one to delete the function of the gene in question. In contrast, diploid organisms, including mammals, present two copies of each gene. Destroying only a single copy on one string of the DNA present in the cell does not remove the gene, or the phenotype linked to it. A solution to this problem is presented in U.S. Pat. No. 5,679,523, Li et al, incorporated herein by reference, which is directed to Random Homozygous Knock Out or "RHKO" technology. In this method, a gene search vector inserts into the genome, and carries a transactivation factor which causes an antisense string to be generated. Thus, insertion of the vector into one string silences one allele, and the generation of the anti-sense string binds to and inactivates or silences the opposing allele.

There are some limits on RHKO technology. First, it is limited to knock out effects. One cannot determine the effect of upregulation of expression, to identify potential targets that can be valuable as targets of upregulation. See, U.S. Pat. No. 5,272,071 for methods of enhancing expression of a gene whose enhanced expression confers an important phenotype. An additional challenge presented by RHKO technology is the need for culturing multiple rounds of modified cells. Between the time required for culturing, and the time required for identification of the perturbation responsible for the changed phenotype (where did the vector insert) a great deal of "downtime" is introduced into the system In U.S. patent application Ser. No. 11/928,393, Duan et al, incorporated herein by reference, there is disclosed a method for enhancing the level of expression of antibodies in a cell that expresses antibodies at a low level, referred to as Random Homozygous Gene Perturbation, or RHGP. In this method a gene search vector, or GSV, that generates an anti-sense RNA that combines with the inserted vector to reduce or eliminate expression of whatever gene is perturbated is used to transfect a cell population. The examples of this application involve targeted perturbation of a specific gene, and again are directed largely to knock out technology, suppressing the expression of a specific cell for inspection of the result in enhanced antibody production (the desired phenotype). This technique also involves the need to expand and culture the cells resulting from the perturbation, and the delays that result.

The target search engine should not be limited to any particular disease or type of phenotype. Thus, in addition to viral disease, one can imagine a variety of situations in addition to antibody expression where the individual, such as a human, not just a host cell, could benefit from an improved phenotype. The history of oncology drug development has evolved with increasing understanding of cancer cell behavior. In the first period of drug development, compound libraries were analyzed for inhibition of tumor cell growth or survival. These approaches were made possible as a result of advances in the culture of tumor cells in the laboratory. Such improvements made it possible to develop experimental screens to identify compounds that killed or prevented the growth of cultured tumor cells. These assessments comprise a Function-First approach, which placed greatest value upon the ultimate outcome and less emphasis upon the identity of the target or mechanistic basis of antitumor activity. These approaches required and stimulated improvements in high-throughput screening procedures and fostered efforts to diversify the array of chemical structures via isolation of novel natural products, by creating novel chemical libraries and/or a combination of the two. The resulting cytotoxic therapies comprise much of our antineoplastic arsenal today, including alkylating agents (platinum compounds), antibiotics (doxorubicin), anti-metabolites (methotrexate, 5-Fluorouracil), alkaloids (vincristine) and taxanes (taxol). Often, the identity of the targets for the therapeutics was unknown or the mechanistic basis was identified later. Although effective, these cytotoxic antineoplastic agents were often accompanied by unwanted side effects, which could limit the use of the compounds over time. Compounding this, increased expression of the P-glycoprotein, coupled with the rapid mutation rate of tumor cells, tends to favor selection of drug resistant tumors (Gottesman and Ling, 2006).

The ability to culture tumor cells in the laboratory also allowed investigators to begin understanding changes that distinguish benign and malignant cells, which heralded an era of targeted intervention. Fundamental advances in the understanding of oncogenes that contribute to malignant transformation and in turn facilitated the identification of signaling pathways that govern cancer cell behavior (growth, survival, and invasion). This improved understanding facilitated new generations of chemotherapeutic agents based on known targets. The resulting compounds impacted known targets, such as topoisomerases (podophyllotoxins), and growth factors or their receptors. The improved selectivity for tumor cells resulted in more effective and selective antineoplastic drugs. Since targeted drugs were screened or engineered to selectively inhibit particular targets, the new molecular medicines were often accompanied by linked diagnostic agents, which might predict patient eligibility or treatment outcome. Though we remain in the midst of this era of targeted intervention, many of the same historical impediments remain, including unwanted side effects and the acquisition of drug resistance. Compounding this, many of the resulting drugs focus on a relatively narrow set of targets (e.g., tubulin, growth factors and kinases). This prioritization was a logical outcome of the need to intensively investigate validated targets. However, an unintentional outcome has been a steady narrowing of the types of targets under investigation. The development of various approaches to target identification are set foth in FIG. 1.

With improved understanding of the genetic links to disease, increased appreciation of the genetic basis of cancer drove interest in genomic and then proteomic sampling of tumor cells. The growth of "-omics" to identify potential targets for cancer cells coincided with dramatic technological advances in DNA sequencing and garnered much attention, leading academic and pharmaceutical communities to invest considerable infrastructure into the technologies. Genomics, proteomics and related strategies increased the number and breadth of targets. Thus, the field found itself awash in a wide array of targets and the perceived need for continued target discovery reached a nadir. However, it was increasingly understood that the correlative links identified using "-omics" often did not distinguish targets that cause or contribute to disease pathology from those that arise as side effects of the disease process. This ambiguity has required considerable investment to resolve questions surrounding cause-and-effect, thus decreasing the general appetite for novel oncology targets since many organization had invested considerable infrastructure into the technologies needed to investigate "-omics" research and its resultant targets Accordingly, it remains a goal of those of skill in the art to develop a method for rapid detection of potential therapeutic candidates which, when identified, may be made the subject of further experimentation to develop their therapeutic potential, either through reduced expression (e.g., gene therapy) or silencing of the proteins encoded thereby (ligand binding therapy) or merely to identify genes that should be made the subject of diagnostics—their presence, or presence in multiple copies, indicating the individual is a likely candidate for whatever phenotype is correlated with the gene in question. Ideally, the technique should be capable of identifying phenotypes resulting from upregulation as well as down regulation, and not require knowledge of the genome, or target gene.

To avoid the expenditure of large sums of money and human resources unnecessarily, the technique needs to yield verifiable potential targets (that is, the new phenotype is due to the change in the genome itself, and not a consequence of either modification per se, or exposure to a challenge condition). It needs to yield results on a basis that reduces the time delays due to cloning and expansion of potential candidates.

SUMMARY OF THE INVENTION

Random Homozygous Gene Perturbation (RHGP) is a method to randomly disrupt genes in a given cell population, allowing for the screening of any desired phenotype and the identification of its associated gene. Instrumental to the power of RHGP is its antisense technology, which allows for the simultaneous inactivation of all copies of a gene, unlike traditional knockout approaches which require repeated targeting to disable every copy in a given cell. Moreover, RHGP is more powerful than the competing RNA interference (RNAi) technology, since it affords the following advantages: the ability to affect any genetic locus in an unbiased way without prior knowledge of targets or pathways; the ability to overexpress or knockdown any targets (including microRNAs) or protein domains regardless of their epigenetic status (silenced or unsilenced); built-in reversibility for immediate validation of phenotypes; and the ability to study phenotypes in vivo with the same vector system. In addition, RHGP is not subject to the off-target affects of RNAi, because the RHGP vectors integrate into the genome and do not use homology as a basis for their activity. RHGP in its current incarnation, however, takes substantially longer to identify gene targets compared to RNAi, because it requires that every targeted locus of interest be cloned into bacteria and individually identified through sequencing. In this invention, we describe the adaptation of a method to rapidly identify all RHGP insertion targets using PCR, thereby bringing the speed of target gene discovery in line with RNAi methodologies. This powerful technique is not limited to identifying potential host proteins for fighting viral or bacterial disease—any syndrome where a host protein is implicated, such as cancer, can be made subject to the powerful process of RHGP.

Building on the techniques of RHKO, where the initial approach was developed to overcome barriers arising from the fact that eukaryotic cells generally have two sets of chromosomes (Li and Cohen, 1996) RHGP employs the same basic approach. The diploid nature of eukaryotic cells precluded simple knockout based evaluation of target genes that have proven to be so powerful in our understanding of bacterial pathways. Unlike siRNA, which is limited to the knockout of known targets, RHGP-based approaches include the ability to simultaneously knockdown both copies of any target gene, independent of any prior knowledge or annotation of that gene. The potent inhibition is possible because the integration event itself is sufficient to knockout the first copy of the gene while antisense expression of the target gene knocks down the second allele (FIG. 2). RHGP can also up-regulate gene expression, including whole genes or individual domains (FIG. 3A). To date, approximately one half of the targets identified using RHGP to date have represented integration in a Sense orientation with the remaining half representing antisense integration events. Consequently, RHGP provides a means to interrogate the entire genome for any genetic change that is causative of the phenotype under investigation.

A central feature of RHGP is a unique lentiviral-based (or monkey murine leukemia virus-based) genetic element, known as a gene search vector (GSV), which was designed to interrogate the entire genome and identify target genes that cause the phenotype of interest. The GSV integrates at a single site within the genome, where it regulates expression of the target gene via an inducible promoter (FIG. 4). A single integration per cell is controlled by transducing cells with GSV at a relatively low multiplicity of infection (MOI). The vector itself encodes for a self-inactivating lentiviral LTR, which prevents the GSV from re-emerging from a transduced cell.

The GSV can integrate into the genome in either a sense or an antisense orientation. In the antisense configuration, the integration event itself inactivates one allele and facilitates expression of an antisense construct, which knocks down genes encoded on the other allele (FIG. 3A). When integrated in the opposite (sense) orientation, RHGP can facilitate overexpression or un-silencing of target genes. This outcome could extend beyond simple overexpression of an entire gene (e.g., insertion upstream of the start site) or trigger overexpression of particular domains when integrating downstream of the start site, which could produce a dominant-negative inhibitor of wild-type gene function. As such, RHGP allows for interrogation of the entire cell genome to identify different types of targeting events.

RHGP requires construction of a "library" of GSV-transduced cells (FIG. 3B). This library comprises GSV integration events that cover the entire genome, both in terms of overexpression and antisense expression. RHGP is flexible and unbiased by the type of cells to be analyzed (lymphoid or adherent), species (human or non-human) or transformed character (primary or immortalized or transformed). The RHGP strategy excludes GSV transduction events that are intrinsically toxic. For example, RHGP transduction events that disrupt the expression of a vital gene will be toxic to the host cells and thus these clones will be eliminated from the RHGP library. Once transduced, the same library can be archived and used for other screens.

RHGP-TAIL has been used to study a variety of phenomena and phenotypes that may be responsive to a disease or insufficiency condition. Discussed herein are various results from using RHGP to study phenotypes implicated in resistance top influenza, resistance to human immunodeficiency virus (HIV) and associated AIDS and cancer. Targets generated by these RHGP studies are also followed up on.

BRIEF DESCRIPTION OF THE FIGURES

FIG. 1 is a chart reflecting recent developments in target discovery methods.

FIG. 6 is a schematic depicting the identification of PTCH1 as a possible target for therapeutic inhibition of influenza by RHGP techniques. Panel 6A reflects the specific process of transducing target cells to identify genes that may influence influenza resistance in those cells, while panel B reflects the genomic DNA sequences flanking the RHGP vector insertion site. As shown in Panel C, integration occurred in an antisense orientation.

FIG. 11A, right panel, shows the survival of a RHGP perturbed cell clone that survived HIV-1 challenge.

FIG. 16 is a chart identifying key characteristics of targets identified by RHGP that may be used to inhibit the formation of metastatic cancer. The identified genes, their insertion site, orientation and characterization is set forth in this chart.

DETAILED DESCRIPTION OF THE INVENTION

Gene Search Vectors

Figure 2:
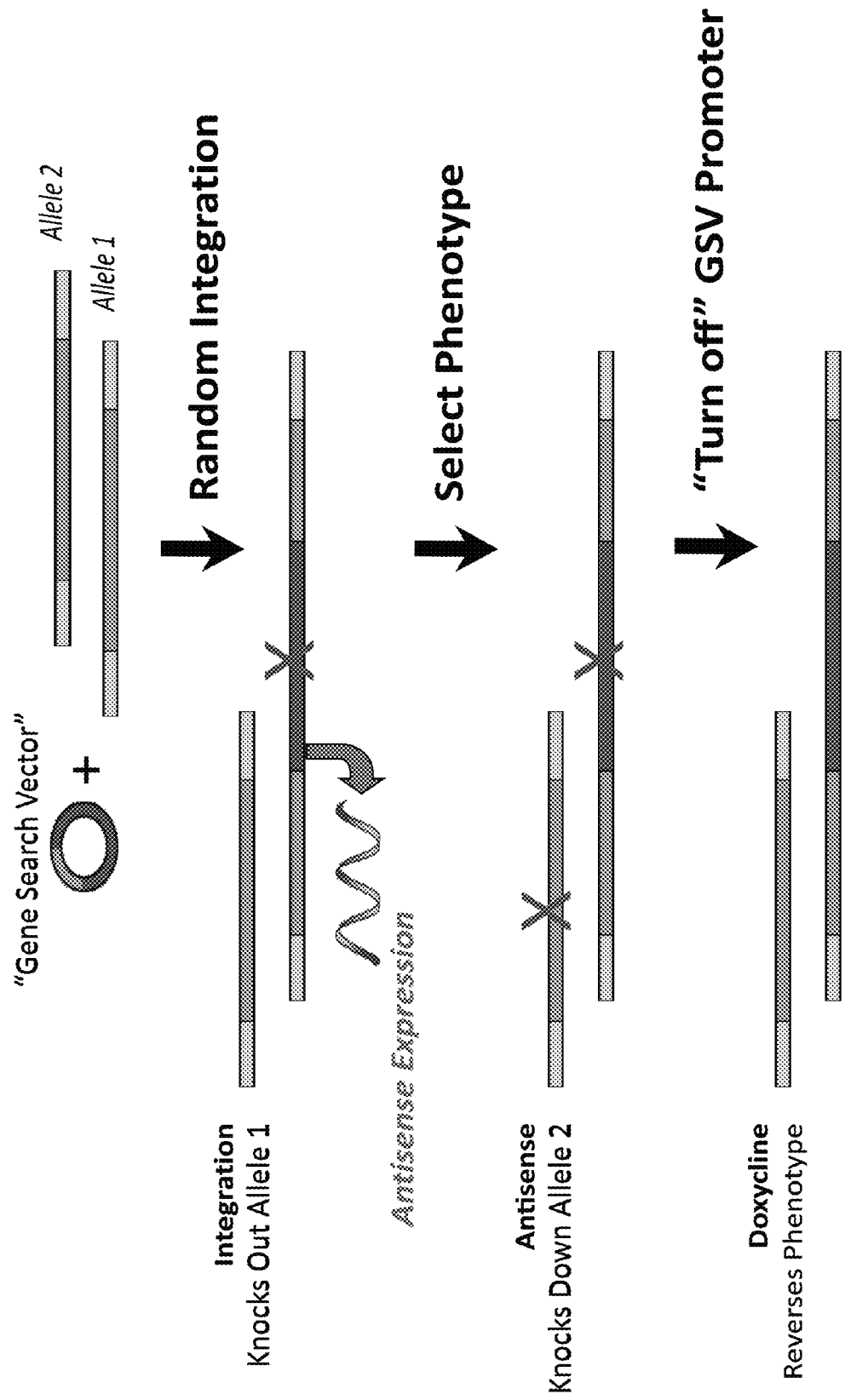
FIG. 2 is a schematic demonstrating the use of the gene search vecor (GSV) of the invention of this application.
Figures 3A, 3B:
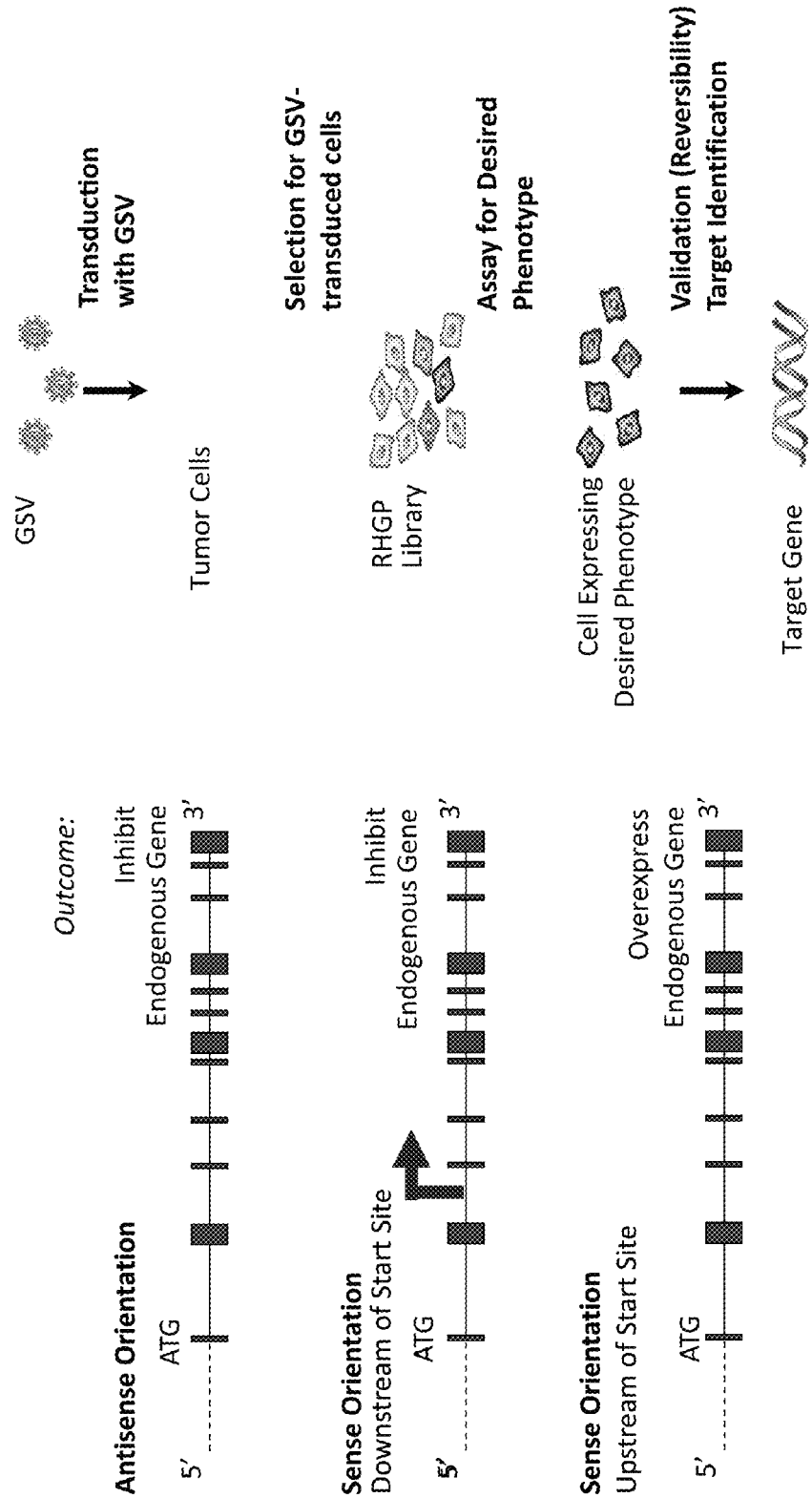
FIG. 3 is a schematic demonstrating the sense and antisense insertion of the GSV of the invention. In panel A, the ability of the GSV to insert in a sense, or antisense, orientation is illustrated. In panel B, the flow path of transduction of cells with the GSV to form a library, identifying the proper phenotype and validations is illustrated.

The RHGP gene search vectors come in two flavors: a Moloney Murine Leukemia Virus (MMLV) version, and a lentivirus version. Understanding how the search vector is constructed and used is an important first step in understanding the detailed practice of this invention.

The MMLV vectors have the advantage that they favor insertions into the promoter regions of genes, thereby ensuring that the entire gene is upregulated or down-regulated. Moreover, MMLV is not biased towards active genes, so that they can insert relatively randomly throughout the genome. The lentivirus vectors have a broad host range of infection as compared to MMLV (on account of them being pseudotyped with the vesicular stomatitis virus G-protein, or VSV-G), and they have the ability to infect both dividing and non-dividing cells. However, they suffer from the fact that they insert relatively non-randomly, in that that they favor actively transcribed genes. The lentivirus versions do not have a bias of insertion within the gene itself, unlike the MMLV versions, which tend to favor promoter regions. The lentivirus versions have consistently yielded higher titers compared to the MMLV vectors for unknown reasons.

The MMLV vectors have the same general structure, in that they have the MMLV 5' and 3' LTRs (long terminal repeats) at either end, and flanking the Cre gene which is used to automatically excise the unimportant elements of the virus after integration (there are LoxP elements so that the Cre and unnecessary elements are automatically removed).

Specific Vector Features

RHGP48: This vector contains a promoter with fourteen (14) copies of a tetracycline responsive element (14xTRE) driving the expression of a puromycin resistance gene without a transcriptional terminator, which creates an antisense transcript (this antisense is the basis of RHGP-based gene inactivation). The TRE is a Tet-Off promoter, in that in the absence of tetracycline, the promoter is active and drives antisense expression. Once tetracycline is added to the media, the promoter shuts off, and the antisense transcript also shuts off, which is the basis of the reversibility feature of RHGP.

RHGP48-RSB: This vector is similar to structure as RHGP48, but instead of a TRE driving the antisense expression, it uses New England BioLabs' RheoSwitch promoter, which is activated by the RSL1 ligand. There are five (5) copies of the RheoSwitch element to which the RheoSwitch activator binds. This promoter drives the expression of the blasticidin resistance gene, which is also without a transcription terminator, so that an antisense product can be made.

RHGP48-RSN: This MMLV vector contains a RheoSwitch regulated promoter driving an antisense transcript, but there is no resistance gene transcribed from the antisense. This "naked" promoter is thought to facilitate both down- and up-regulation events of targeted genes, because theoretically having a gene downstream of a promoter may impair the ability of translating a downstream target (because a gene such as blasticidin or puromycin has a translation stop codon). In order to allow for selection of insertion events, a constitutive phosphoglyerate kinase (PGK) promoter is present and driving a blasticidin resistance gene (this is a normal gene in the sense orientation, and does not produce an antisense transcript)

The lentivirus vectors contain both 5' and 3' LTRs, but the 3' LTR is self-inactivating (called a 3' SIN-LTR), so that after insertion into the genome, the vector cannot replicate and produce virus. This increases the safety profile dramatically. These vectors do not contain the Cre gene, but they all have LoxP sites so that they can be removed (reversed) in the genome by adding Cre exogenously. These vectors also contain the RSV enhancer element in the 5' LTR to allow for higher transcription, and hence, production, of lentivirus.

RHGP11: This vector has the 14xTRE driving EGFP to produce a regulated antisense product, as well as green fluorescent protein. This allows the cells to be seen under a fluorescent microscope, and sorted by FACS if necessary. In addition, this vector has the zeocin resistance gene being driven off of a PGK promoter to allow for drug selection.

RHGP11-CMVE: This vector is similar to RHGP11, but instead of a regulated TRE driving the antisense expression with EGFP, the antisense is constitutive, since a CMV promoter is driving the EGFP antisense construct. This may be important in cases where one cannot reverse the phenotype easily (such as in vivo studies).

RHGP22: This vector has a pTight TRE instead of the typical TRE. There are five (5) copies of the pTight response elements. The pTight is also a tetracycline regulated promoter for the antisense, but it is less leaky than the original TRE. This pTight is driving antisense expression through the blasticidin resistance gene.

Figure 5A:
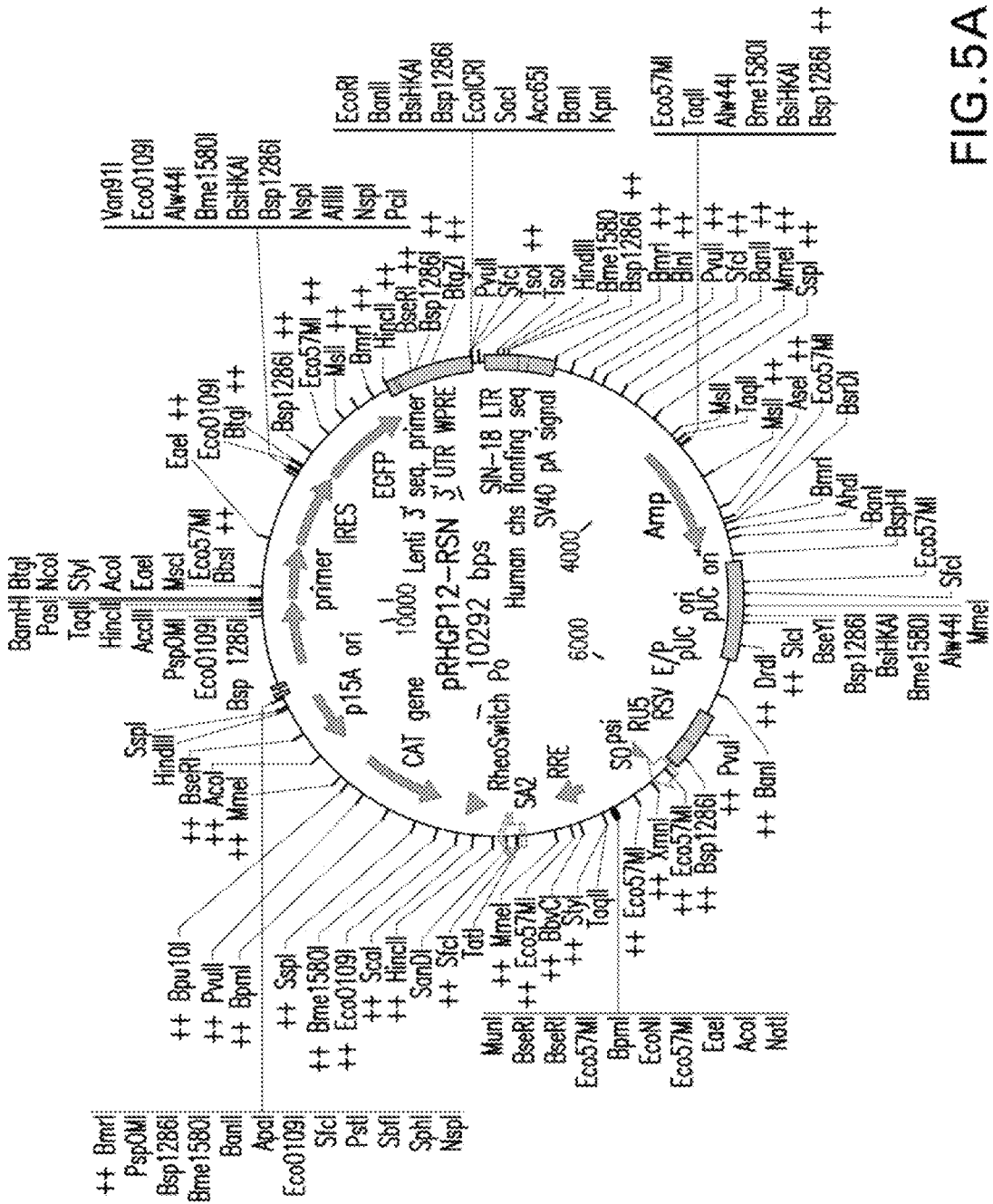
FIG. 5 is a Gene Map for GSV pRHGP-12RSN used in this invention. The proper mapping is given in the upper illustration—the corresponding linear representation is set for the in the lower portion of FIG. 5.
Figure 5B:
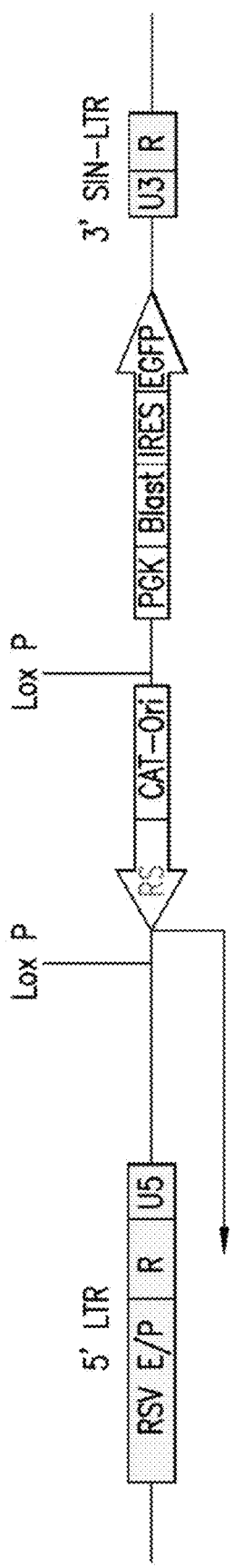

RHGP12-RSN: This vector uses the RheoSwitch promoter to drive a "naked" antisense transcript. In addition, the vector can be selected by drugs by the fact that a PGK promoter is driving the expression of the blasticidin gene. In addition, the EGFP gene is placed downstream of the blasticidin gene via an IRES (internal ribosomal entry site) element, so that the PGK promoter can drive production of both proteins. A gene map for this vector is set forth in FIG. 5.

RHGP13-CMVN: This vector also has a "naked" promoter generating an antisense transcript, but this promoter is constitutive (the CMV promoter), and not regulated like the RheoSwitch or TRE/pTight promoters. This, again, is useful for in vivo studies, where a stable non-regulated antisense production makes sense. This vector has the same PGK-BS-IRES-EGFP construct as in the RHGP12-RSN vector.

RHGP-TAIL Protocol

The success of RHGP screening is dependent upon the assay that is used to screen the phenotype. Similar to other screening procedures, the desired phenotype must be unambiguous and robust. Once those minimal criteria are satisfied, RHGP can be applied to virtually any application in which the desired phenotype allows the cells to be physically isolated. As one example, our laboratory and others have utilized RHGP to identify targets that cause tumor cells to become resistant to chemotherapeutic challenge with cytotoxic agents (Lih, Wei, and Cohen, 2006; Reiske et al., 2009) or hormone therapy. Under these conditions, drug sensitive cells perished while a subset of RHGP-perturbed cells survived. Unlike the correlative findings that typify "-omics" based approaches, survival in the face of drug challenge was directly caused by the RHGP transduction event. The selection of a desired phenotype is not limited to cell-based assays and RHGP can likewise be used for applications in vivo. For example, one can isolate cells that gain tumorigenic or metastatic potential in animal models. Beyond survival as an outcome, RHGP can also select for other properties, such as affinity-based isolation of cells that express particular markers. Such outcomes are possible when the expression of a specific marker (as the desired phenotype) can be used to physically isolate cells with the using flow cytometry or panning procedures.

Considerable efforts have been invested to optimize the robustness and efficiency of RHGP. The reversible promoter that drives expression from the GSV provides an efficient means to rapidly validate targets of interest. After the desired phenotype is obtained, the experiment can be repeated with a silenced GSV promoter to reverse the phenotype. If the phenotype persists using a silenced GSV, that clone would be deprioritized since the phenotype might have arisen as the result of an unrelated artifact. As such, once an RHGP library has been constructed, it is possible to select for a phenotype of interest and validate the reversibility of the phenotype, all in a single study.

Once a phenotype has been validated using the reversible promoter, the GSV encodes for motifs to identify the target genes and determine the orientation of the GSV integration (e.g., sense or antisense). Early versions of RHGP required physical isolation of the host genomic DNA followed by conventional sequencing. This procedure required the outgrowth of clones to sufficient number to isolate enough genomic DNA for bacterial transformation. Individual bacterial colonies were then isolated and the plasmid isolated for sequencing of GSV integration event. This process required weeks of effort with limited throughput. Target identification has been approved using a modification of Thermal Asymmetric Interlaced (TAIL)-PCR. TAIL-PCR was originally developed to identify gene insertion in plants (Liu et al., 1995). More recently, it has been used to identify gene insertion in the mouse genome (Pillai et al., 2008). We incorporated TAIL-PCR to implement high throughput identification of GSV insertion sites since small numbers of cells are needed to isolate genomic DNA. These improvements facilitate high throughput screening and yield information about the GSV insertion site within days rather than weeks.

This is the first application of TAIL-PCR for high throughput genome wide identification of transgene insertion sites, as well as the first application of TAIL-PCR for transgene insertion site identification in human cells.

The original RHGP cloning technique involves growth of mammalian cell clones to sufficient number (for example, to a 6-well plate density) to isolate a substantial quantity of genomic DNA for restriction digestion and self-ligation. Afterwards, the self-ligated plasmids are transformed into bacteria, and a number of colonies are individually picked, grown overnight, and plasmid is isolated from these cultures the next day. These plasmids are then sent off for sequencing to identify the site of transgene insertion.

With TAIL-PCR, mammalian cell clones can be directly processed for genomic DNA extraction in 96 well plates, thereby making the procedure amenable for high throughput screening. The DNA is then subjected to three cycles of TAIL-PCR in a 96 well plate format using a mix of known and random primers, and then the plate is submitted directly for sequencing after the third PCR round, yielding insertion site information in as little as three days. The following table compares the various technologies and an estimate of their relative rates (at optimal efficiency):

|  | RNAi | RHGP (cloning) | RHGP (PCR) |
| --- | --- | --- | --- |
| Time to identify 200 genes from cells | Weeks | Months | Weeks |
| Relative Cost | +++++ | +++ | ++ |

This is a typical TAIL-PCR protocol:

Use approximately 50-100 ng genomic DNA per well in a PCR reaction. Less DNA can certainly be used if DNA is limiting. For example, the usual genomic DNA preps have yields in the range of 0.2 to 0.8 ug/ul, so a 1:10 dilution in TE or H$_2$O for a PCR reaction has worked well. Since each DNA sample will be divided into six (6) reactions having one forward and one of six reverse PCR primers, all in independent wells, a premix of eight (8) reactions per genomic DNA sample is prepared using the Immomix Red polymerase from Bioline. The stock concentration of the forward primer is 1 uM, and the reverse primers are 10 uM each (for a final concentration of 0.15 uM and 2 uM, respectively).

| Component | Volume | Rxn |
| --- | --- | --- |
| H20 | 1.3 | 10.4 |
| forward primer (1 uM) | 1.5 | 12 |
| reverse primer (10 uM) | 2 | 16 |

-continued

| Component | Volume | Rxn |
|---|---|---|
| template DNA | 0.2 | 1.6 |
| 2x Immomix Red | 5 | 40 |
| TOTAL | 10 | 80 |

Primary TAIL-PCR cycling conditions (approximately 6 hours):
94 deg C. 10'×1
94 deg C. 10", 64 deg C. 30", 72 deg C. 3'×10
94 deg C. 10", 25 deg C. 3', 72 deg C. 2.5°×1
94 deg C. 10", 64 deg C. 3', 72 deg C. 2.5', 94 deg C. 10", 64 deg C. 3', 72 deg C. 2.5', 94 deg C. 10", 44 deg C. 1', 72 deg C. 2.5°×15

For lentivirus RHGP vectors, the following primers are used per DNA sample (six (6) reactions each):
Primary TAIL-PCR: ISP1 (forward)+AD1 through AD6 (reverse)
Secondary TAIL-PCR: GSP3new (forward)+AD1 through AD6 (reverse)
Tertiary TAIL-PCR: ISP2 (forward)+AD1 through AD6 (reverse)
Forward primers [SEQ ID NOS.: 1-3]:

```
ISP1      CAGCAAGCCGAGTCCTGCGTCG
GSP3new   TCGAGAGAGCTCCTCTGGTTTC
ISP2      GTCCCTGTTCGGGCGCCACTGC
```

Reverse primers [SEQ ID NOS.: 4-9]:

```
AD1    NGTCGASWGANAWGAA
AD2    TGWGNAGSANCASAGA
AD3    AGWGNAGWANCAWAGG
AD4    STTGNTASTNCTNTGC
AD5    NTCGASTWTSGWGTT
AD6    WGTGNAGWANCANAGA
```

For MMLV RHGP vectors, the following primers are used:
Forward primers [SEQ ID NOS.: 10-12]:

```
48RS1    CTGCATCCTGGGATCAAAGCCATA
48RS2    CGTGAATTGCTGCCCTCTGGTTAT
48RS3    CGTCCTCTAGCGATGATAAGCTGT
```

Reverse primers: (same as above)
The samples in #1 can be run on a 1% agarose gel to visualize bands. Afterwards, do a 1:200 dilution of each sample. This is done by doing a 1:20 dilution of each sample into water first, and then using 1 ul of this in the subsequent 10 ul PCR reaction (to achieve a 1:200 final dilution factor) for secondary TAIL-PCR. Sometimes there is volume loss in the PCR samples, so 5 ul of water can be added to each well if desired prior to dilution (the same can be done before tertiary TAIL-PCR). The premix per reaction for secondary TAIL-PCR is as follows:

| Component | Volume |
|---|---|
| H20 | 0.5 |
| forward primer (1 uM) | 1.5 |
| reverse primer (10 uM) | 2 |
| template DNA (1:20 dilution) | 1 |
| 2x Immomix Red | 5 |
| TOTAL | 10 |

The reverse primers and template DNA can be aliquoted using multichannel pipettes. Secondary TAIL-PCR cycling conditions (approximately 4 hours):
94 deg C. 10'×1
94 deg C. 10", 64 deg C. 3', 72 deg C. 2.5', 94 deg C. 10", 64 deg C. 3', 72 deg C. 2.5', 94 deg C. 10", 44 deg C. 1', 72 deg C. 2.5°×12

Run the samples in #2 on a gel if desired, and do 1:200 dilution as indicated in #2, and using the same premix in #2, do tertiary TAIL-PCR with the following cycling conditions (approximately 2 hours):
94 deg C. 10'×1
94 deg C. 10", 44 deg C. 1', 72 deg C. 2.5°×20

The samples in #3 can be run on a 1% agarose gel if desired. The plate can then be directly sent for sequencing using the final specific primer (such as ISP2 for lentivirus, or 48RS3 for MMLV). If there is a concern for low volumes, 15 ul of water can be added to each well for easier handling.

This procedure has successfully identified the same sites of virus integration in clones where the integration sites have been identified using the original RHGP cloning approach, using both RHGP lentivirus and MMLV vectors in human and non-human cell lines.

EXAMPLE 1

Investigation of Influenza Factors and Identification of PTCH1

Influenza infection remains a leading cause of infectious disease-mediated morbidity and mortality. Accumulating evidence indicates that most variants of seasonal and pandemic influenza have developed resistance to conventional therapies. Such information has spawned new interest in identifying novel approaches to target influenza. Our laboratories have been developing a new strategy of Host-Oriented Therapeutics, which seeks to target host molecules in a safe and effective manner that prevents the virus from causing disease. Using an improved discovery technology, RHGP, we identify PTCH1 as an essential host target that critically controls influenza virus infection. We further demonstrate that targeted intervention against PTCH1 using antibodies or siRNA decreases influenza infection. Finally, we demonstrate the involvement of PTCH1 in influenza infection outside of the laboratory by showing that genetic variations of PTCH1 relate to decreased disease morbidity in the field. Altogether, these findings have important implications for the development of novel, host-directed therapeutics to improve influenza disease management.

Influenza remains one of largest causes of infectious disease-mediated suffering and death. In average year, influenza claims 20-30,000 lives and billions of dollars in economic damages. Despite its widespread prevalence, vaccination remains sporadic and recent studies indicate vaccines may be effective in less than half of those treated. Compounding this, only a handful of therapeutics have been developed to treat influenza infection and increasing evidence indicates many seasonal and pandemic (avian) strains have become resistant to these compounds, thus obviating their application. The inevitable outgrowth of drug-resistant strains is not unique to influenza and the emergence of resistant strains of influenza, HIV, herpes and other viruses has forced the medical community to reconsider strategies for antiviral therapy.

Conventional antivirals have targeted viral-encoded pathways. The fundamental rationale has assumed that targeting of viral pathways will minimize toxicity to normal host cells. However, many of the resulting compounds are indeed quite toxic and worse still, a focus on viral targets places selective pressure on the pathogen to derive variants that are resistant to therapy. This need for alternatives has driven the approach practiced herein, which seeks to develop new therapeutics that are insensitive to drug resistance and which can be applied to a broad spectrum of different virus types.

Our laboratory has been developing a concept of Host Oriented Therapeutics for Infectious Disease. This approach seeks to identify host-derived targets that are mis-expressed or functionally altered in virus-infected cells. In doing so, we have postulated that the altered expression or function would provide opportunities for novel therapeutics that are safe an effective in treating viral diseases. By identifying, and then targeting, pathways that are essential to different types of influenza, we might develop a much-needed antiviral with a broad-spectrum of application. A clear gap in knowledge is the need to identify safe and effective host targets and, ideally the means to prosecute those targets. To that end, we successfully utilized our core technology, RHGP. Our experimental strategy centered upon integration of the GSV at a single site in the genome, where it can either cause overexpression or loss of expression of the target gene. As such, RHGP allows us to interrogate the entire cell genome to identify different types of events that allow host cells to resist or survive influenza infection RHGP was used to identify PTCH1 as an essential host target in influenza infection. Targeting intervention against PTCH1 can block influenza infection. Finally, SNP analyses demonstrate that PTCH1 relates to disease outcome during natural outbreaks of influenza in porcine populations.

Materials and Methods

Cell culture. Human MDA-MB231 breast cancer cells were purchased from the American Type Culture Collection (ATCC). The Phoenix A cell line was a gift from Dr. Nolan, Stanford University and mouse N2a cell line was a gift from Dr. Xu, Rockefeller University. MDA-MB231 cells were cultured in DMEM containing 10% FBS and N2a cells were cultured in 50% DMEM and 50% Opti-MEM media containing 5% FBS.

RHGP Library Generation and Screening. The RHGP gene search vector was applied to generate RHGP libraries in MDCK cells. RHGP libraries infected with influenza virus A/Udorn/72 at a multiplicity of infection (MOI) of 0.1 or 0.001 as indicated. Two weeks after second round of infection, genomic DNA was obtained using the BIO-RAD AquaPure Genomic DNA Isolation Kit, Self-ligated genomic DNA was concentrated and electroporated into *E. coli* cells and selected using chloramphenicol.

Validation of host target genes with siRNA. The human duplex siRNA homologues for PTCH1 were prepared as recommended by the manufacturer. The siRNA NP-1496 sequence [SEQ ID NO.: 13] (GGAUCUUAUUUCUUCG-GAGUU), which targets the nucleocapsid (NP) gene of influenza virus, provided a positive control (Ge et al., 2003). Non-targeting siRNA, siCONTROL1 provided a negative control. HEK293 cells were plated in 24-well plates at $1 \times 10^5$ cells per well, respectively. After 24 hours incubation, the cells were transfected with 20 nM of siRNA and TransIT-TKO, according to the manufacturer's instruction (Minis). Twenty-four hours after second round of transfection, the samples were washed with MEM followed by infection with influenza virus A/Udorn/72 (MOI 1). The cells were incubated for 1 hour with gentle rocking every 15 minutes. The culture medium from each well was collected 48 hours post-transfection and progeny viruses in the medium were titrated using standard plaque assays.

Flow cytometry: For flow cytometric analysis, MDCK cells were suspended using trypsin and $1 \times 10^5$ cells were incubated on ice with 10 mg/mL antibody for 30 minutes. Cells were washed three times with PBS containing 1% BSA (Sigma, St. Louis, Mo.) in PBS on ice and incubated with FITC conjugated goat anti-rabbit (Becton Dickinson, San Jose, Calif.) for 30 minutes on ice. After washing the cells were fixed in PBS with 1% paraformaldehyde. Data were acquired in an EasyCyte Flow Cytometer (Guava Technologies, Hayward, Calif.) and analyzed using FlowJo analysis software.

SNPs and Datasets. PTCH1 SNPs were selected to fulfill two criteria: (a) acceptable allele frequency; and (b) successful formatting by external genotyping provider (Sequenom).

The Influenza dataset was collected in a commercial pig production system using PIC genetics. During the study period, the farm experienced an outbreak of swine influenza virus. Four (4) growth traits were measured: (1) Growth: This is a 0/1 trait that compared high and low growth animals; (2) Life DG: Lifetime daily gain (g/day); (3) LDG Carcass Gain: (grams/day) and (4) Wean:—end daily gain (g/day)

LSM favorable genotype—LSM unfavorable genotype/2

Results

To identify targets that render host cells resistant to influenza, an RHGP library was generated as described above in MDCK cells and influenza challenge performed as indicated (FIG. 6A). The library was challenged by infection with influenza A/Udorn/72 to select for influenza-resistant cells. We had previously established that infection with A/Udorn/72 (MOI of $10^{-1}$) reproducibly killed all MDCK cells within 48 hours (not shown). As a control, parallel cultures of mock-transduced cells were treated identically and no survivors were observed after 48 hours.

After selecting for RHGP-transduced cells that survived multiple rounds of influenza challenge, we focused on one particular culture (R26-7), which survived influenza infection. The RHGP gene search vector allowed us to efficiently locate target genes and determine the orientation (sense or antisense) of the integration event. Genomic DNA was isolated from R26-7 cells and genomic DNA sequences flanking the RHGP vector insertion sites was sequenced and mapped against the canine genome using the UCSC Genome Browser (FIG. 6B). The integration event in R26-7 occurred in canine chromosome one, in an antisense orientation, in the PTCH1 gene (FIG. 6C). As such, the integration physically disrupted the first copy of PTCH1 and the resulting antisense knocked down expression of the second allele.

Validation of PTCH1 Using Naive Cells

Figure 7:
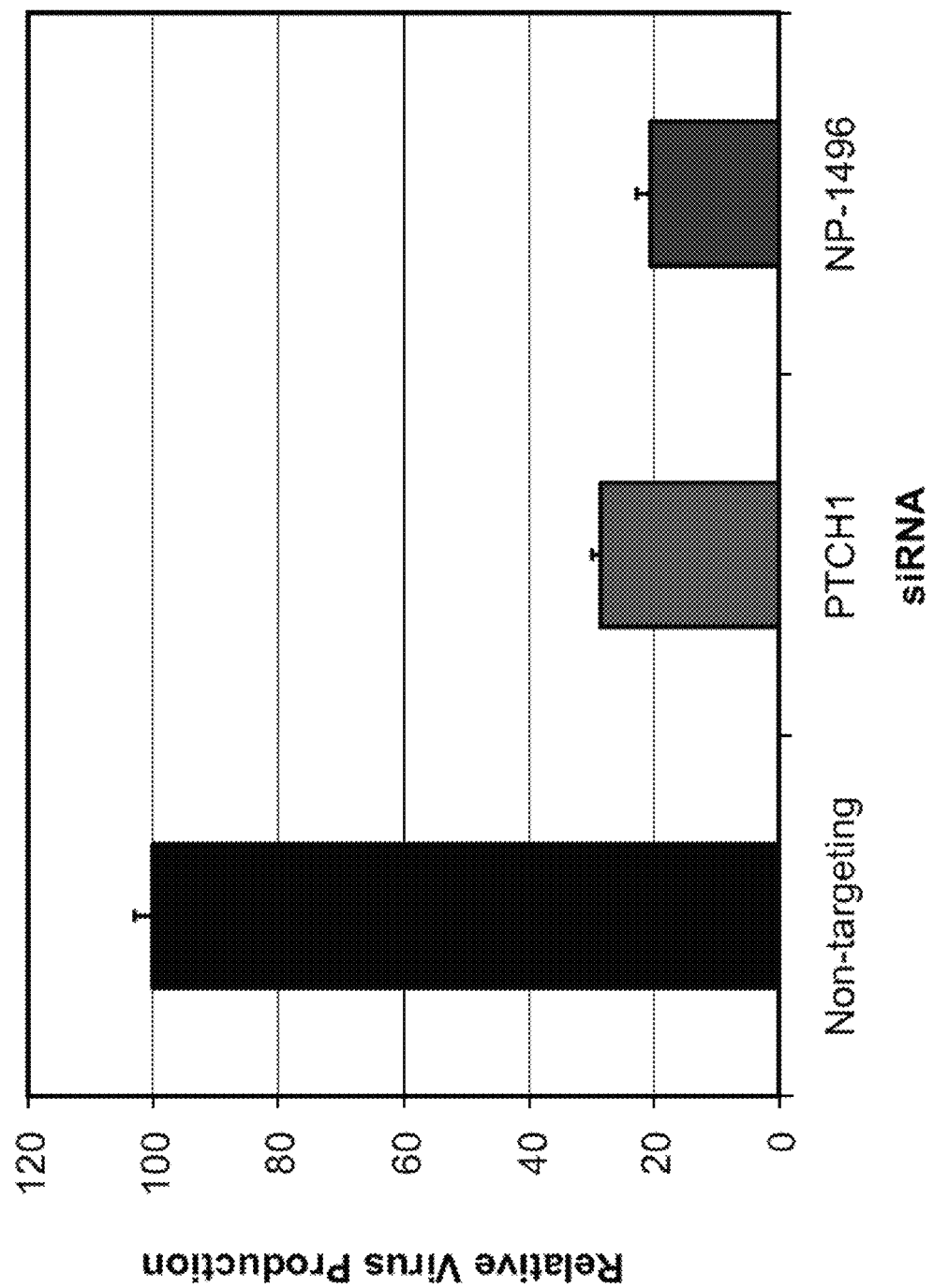
FIG. 7 is a graph showing the relative inhibition in virus production caused by inhibition of PTCH1 as compared with a control.

We then sought to verify PTCH1 as a candidate target that prevents influenza-mediated killing of host cells. These studies were meant to exclude artifacts that might arise from RHGP or the use of MDCK cells. Since PTCH1 had been isolated from canine-derived MDCK cells, we identified its human homologue and expressed siRNAs selective for these targets in human HEK-293 cells. Duplex siRNAs were generated and transfected into HEK293 cells. Non-targeting siRNAs provided a matched control for the transfection and a reference standard. NP-1496 duplex siRNAs, which target a critical influenza gene and have been demonstrated to inhibit influenza infection, provided a positive control (Ge et al., 2003). Since influenza infection does not efficiently kill HEK293 cells, we modified our experimental protocol to measure viral titers (instead of host cell survival) as the primary endpoint for efficacy. The siRNA-treated HEK293 cells were infected with A/Udorn/72 for 48 hours and viral titers were measured by plaque assays. PTCH1 duplex siRNAs decreased influenza virus production and at levels comparable to the positive control (NP-1496 siRNAs). (FIG. 7).

Additional Targets

Using the same procedures in similar cells and with similar challenges, RHGP technology was used to identify additional targets. Among these are SLC25A25 (previously characterized as a protein involved in mitochondrial transfers across the membrane and possibly Mg-ATP exchange), Rgnef (observed to have a role in cell adhesion, cell motility and B-lymphocytes activation, and possibly cell apoptosis), Nedd4 and Herc6 (both ubiquitin ligases) all as potential targets for influenza and Robo1 (a receptor implicated in cell mobility and axon guidance) as a potential target for HIV. Some of these are discussed, below. As these proteins, in a viral infection mode, are manifested on the cell surface, each could be targeted using monoclonal antibodies, peptides, antisense, siRNA, etc.

Antibody Targeting of PTCH1 Decreases Influenza Infection

Figure 8A:
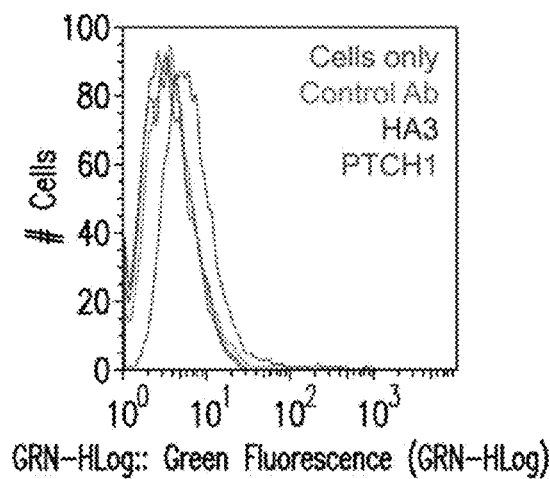
FIG. 8 is a graphic identification of the effect of inhibition of PTCH1 at different MOIs. PTCH1 antibodies are shown binding influenza infected cells, with substantially more staining (binding) observed with infected cells than non-infected cells (contrast 8A and 8B). The MOI for antibody treatment was repeated at a higher MOI, giving a decrease in influenza, as shown in Panel 8C.
Figure 8B:
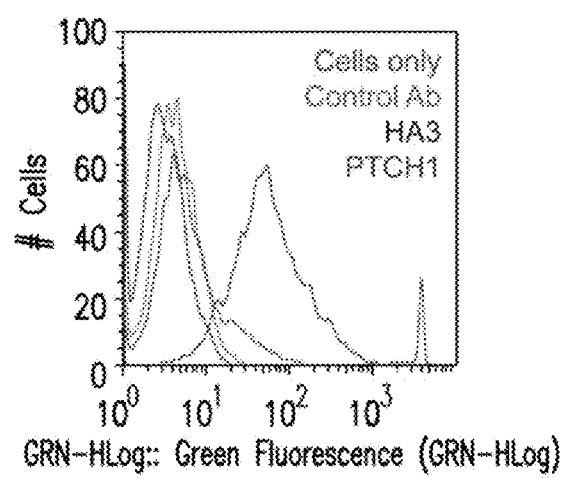

PTCH1 is a multipass transmembrane protein. As such, we considered that it might provide a target for antibody-based intervention. To evaluate this possibility, affinity purified antisera were obtained and tested for their abilities to recognize PTCH1 on the surface of influenza-infected cells. MDCK cells were infected with A/Udorn influenza for 18 hours prior to staining of intact cells. This experimental design was utilized to minimize the potential for artifacts that could arise as a result of prolonged incubation with virus or fixation, either of which could disrupt membrane integrity. Antibodies specific for viral-encoded hemagglutinin and a matched control, which does not recognize PTCH1, provided positive and negative controls, respectively. PTCH1 antibodies bound influenza-infected cells and considerably more staining was observed with infected cells than non-infected controls (FIGS. 8A and 8B). This outcome did not represent a loss of membrane integrity since the cells continued to exclude Trypan Blue and other vital dyes under the conditions utilized.

Figure 8C:
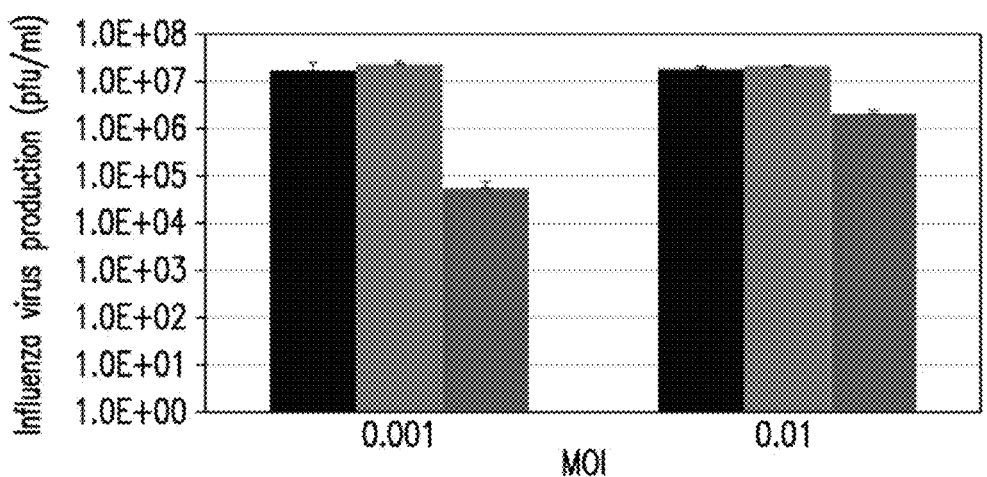

Based on the abilities of PTCH1 antibodies to bind influenza-infected cells, we then asked if treatment with these antibodies might alter influenza infectivity. MDCK cells were infected with influenza in the presence of absence of PTCH1 antibodies. Culture supernatants were then harvested and the number of infectious influenza particles was quantified using standard plaque assays. These studies demonstrated that PTCH1 antibodies decreased influenza propagation by 2-3 logs (100-1000 fold) as compared with untreated cells or controls that had been treated with non-specific antisera. We then asked if this outcome might represent antibody inhibition of initial infection or later stages of the viral life cycle. This question was addressed by repeating infection at a higher multiplicity of infection (MOI) of 0.1 (rather than 0.001). We reasoned that if PTCH1 antibodies comparably inhibited influenza at a relatively high MOI, they might be blocking initial attachment or entry into the infected cells. On the other hand, if the antibodies impacted a later stage of the life cycle (e.g., budding or release), then inhibitory activity would be decreased at a higher MOI. Consistent with the latter idea, the antiviral effect of PTCH1 antibody treatment was decreased at a higher MOI, imparting a one log (10 fold) decrease in influenza. (FIG. 8C). These results suggest that PTCH1 may provide a suitable target for antibody therapy and that the antibodies appear to be blocking a relatively late stage of the viral life cycle.

Translating PTCH1 from the Laboratory to Influenza Infection in the Field

Based on intriguing findings with cell-based assays, we asked if PTCH1 would relate to influenza susceptibility outside of the laboratory. For this, we utilized a single nucleotide polymorphism (SNP) assessment of robustness traits in swine populations during a swine influenza virus outbreak. Specifically, we asked if the PTCH1 SNPs were associated with changes in swine weight gain, which is an understood outcome of influenza infection in pigs.

A series of different SNPs within or near PTCH1 (known as 619, 661, 662 and 663) were selected based on several criteria, including level of significance, allele frequency, additive verses dominance effects, and size of effect (phenotypic standard deviation). We then asked if the SNPs were associated with influenza resistance in the field. For this, DNA from pigs exposed to virus infections in the field was extracted, genotyped for each SNP, and statistical associations between SNP genotype and performance traits were determined. The studies utilized a dataset from a large farm that had undergone a swine influenza outbreak during the period of dataset collection. Our analyses related two different PTCH1 SNPs (619 and 660) with increased average daily weight gain and weight gain since time of weaning (Table I). These outcomes were statistically significant and suggest that PTCH1 can relate to weight gain, which is a significant indicator of influenza morbidity in the porcine population.

Thus, using RHGP technology, a major finding is a demonstration that the PTCH1 cell surface receptor is essential for infection by influenza virus and that targeted intervention against PTCH1, using either siRNA or antibodies, can decrease influenza infection. We have also shown that PTCH1 is broadly utilized by influenza during infection of cells from many different species, including humans, dogs and pigs. Finally, we translate the importance of these basic findings to the situation in the field by demonstrating that PTCH1 relates to disease outcome during natural infection of porcine populations.

One novel aspect of our present study is the demonstration that PTCH1 regulates influenza infection of host cells. PTCH1 is the human homolog of the cellular receptor for sonic hedgehog, a secreted molecule that governs cellular organization, growth and survival during embryogenesis. PTCH1 has also been implicated with roles as a tumor suppressor and is linked with various epithelial malignancies. From a mechanistic standpoint, the basis of influenza is unknown but the differential effect of antibody treatment at different MOIs may suggest a role for PTCH1 in relatively late stages of the viral life cycle.

Another important aspect of our present report is the utilization of RHGP to identify novel, host-directed targets for antiviral diseases. RHGP provides an opportunity to identify any target in a cell that regulates the phenotype under investigation, whether via overexpression or loss of expression. A central feature of RHGP is that one need not have prior knowledge of the target to determine its involvement in a disease process and our results further bolster this concept since PTCH had not been previously linked with influenza.

From the standpoint of disease management, there are interesting and important potential implications for our present findings. First, PTCH1 may provide an opportunity to intervene against infection by influenza using antibody or other approaches that target PTCH1 expression or function. The fact that comparable findings were obtained using multiple species (human, dog, pig) may indicate that PTCH1 represents an important core mechanism used for influenza infection. A central tenet of our host-directed approach to target infectious disease focuses on the idea that identification of fundamental pathways could provide a means to target multiple virus strains and future investigation should detail further the role of PTCH1 in different seasonal and pandemic forms of the viral pathogen. A second opportunity arising from host-directed therapies is the concept that viruses may not have developed alternatives to important host mechanisms. If correct, then effective targeting of PTCH1 might provide an opportunity to overcome issues associated with the acquisition of drug resistance that have long plagued the treatment of influenza.

Table I. PTCH1 Polymorphisms Relate to Increased Weight Gain of Porcine Populations In the Context of a Swine Influenza Outbreak—(The effect of PTCH1 polymorphisms on the growth (grams/day) of one copy of favorable allele (relative to the major allele). All results are shown as the relative increases in weight gain relative to the major allele (p value). Lifetime Daily Gain=Final weight minus birth weight. Wean End Daily Gain=Final weight minus weight at time of weaning.)

TABLE 1

| Marker | Lifetime Daily Gain (grams/day) | Wean End Daily Gain (grams/day) |
|---|---|---|
| 619 | 23.69 (0.023) | 21.88 (0.036) |
| 660 | 14.19 (0.047) | 15.16 (0.033) |
| 661 | 11.93 (0.149) | 13.53 (0.105) |
| 662 | 6.81 (0.120) | 7.81 (0.076) |

EXAMPLE 2

RHGP Used to Identify Other Influenza Factors

Conventional approaches for therapeutic targeting of viral pathogens have consistently faced obstacles arising from a development of resistant strains and a lack of broad-spectrum application. Influenza represents a particularly problematic therapeutic challenge since seasonal antigen shift and drift, combined with a high viral mutation rate, have confounded many conventional antivirals. Newly emerging or engineered strains of influenza represent even greater threat as typified by recent interest in avian subtypes of influenza. Based on the limitations associated with targeting virally-encoded molecules, we have taken an orthogonal approach of targeting host pathways in a manner that prevents viral propagation or spares the host from virus-mediated pathogenicity. To this end, Random Homozygous Gene Perturbation (RHGP) was used to identify host-oriented targets that are well-tolerated in normal cells but inhibit influenza. Use of TAIL-PCR with RHGP facilitated a thorough screening of the entire genome, both for overexpression or loss of expression, to identify targets that render host cells resistant to influenza infection. We identify a set of host-oriented targets that prevent influenza killing of host cells and validate these targets using multiple approaches. These studies provide further support for a new paradigm to combat viral disease and demonstrate the power of RHGP to identify novel targets and mechanisms.

One new approach for addressing viral infection is to target host factors that are essential to the pathogenesis of viral disease. A prominent example from the war on HIV/AIDS is the development of antagonists of CCR5. These antagonists seek to prevent the function of a surface-exposed co-receptor that is necessary for the binding and internalization and early findings suggest these agents may provide much-needed options for the treatment of the subset of patients infected with CCR5-trophic viruses.

In Example 2, a different investigation of possible targets for therapeutic intervention with respect to influenza in mammals including humans is investigated. As noted above, this invention includes the application of an improved form of RHGP, which can also cause up-regulation of any target in the cell, including whole genes or individual domains. Consequently, RHGP provides a means to interrogate the entire genome for any genetic change that is causative of the phenotype under investigation. We applied RHGP to identify and validate a set of host-oriented targets that are required for influenza infection.

MATERIALS AND METHODS

Chemicals and cell culture. MDCK cells, human 293HEK cells and MEM medium were purchased from the American Type Culture Collection (ATCC). Fugene 6 was purchased from Roche. The Lipofectamine 2000, Doxycycline (Dox), T4 DNA ligase, ElectroMax DH10B competent cells and ViraPower Packaging kit were purchased from Invitrogen. The vector pIREShyg3 and pTRE-luc were obtained from Clontech. The RNase A and proteinase K were purchased from Sigma. Influenza virus A/Udorn/72 was provided by Charles River Lab. All the restriction enzymes were purchased from New England BioLab. The cell culture media and supplements were from either Invitrogen or Hyclone. All short siRNA oligonucleotides were synthesized by Dharmacon Research. The TransIT-TKO, siRNAs transfection reagent was purchased from Mints. The MDCK cells were cultured in MEM containing 10% FBS. All the cell culture was incubated with 5% $CO_2$ at 37° C. The Bright-Glo luciferase Assay System used for Dox inductivity assay was purchased from Promega.

Construction of pTet-Off transactivator vector and the MDCK/Tet-off stable cell lines. The pTet-Off transactivator vector was constructed using the pIREShyg3 vector as a backbone. A PCR-generated tTA fragment was inserted into the BamHI and SofI sites of the pIREShyg3 vector to generate the pTet-Off transactivator vector, pIREShyg3-tTA.

To create MDCK/Tet-Off cell lines, $1-2 \times 10^6$ MDCK cells in 10-cm plates were transfected with 10 ng of pIREShyg3-tTA vector and 30 µl of fugene 6 according to the manufacturer's instruction. Twenty-four hours post-transfection, the MDCK cells were split by 1:10 dilution and cultured with 200 µg/ml of hygromycin. The medium was changed every three (3) days until the untransfected cells were killed and the transfected stable cell colonies were formed. The visible individual colonies were picked and subcultured in 24-well plates. The hygromycin resistant clones were screened for the Dox induction activity using pTRE-luc vector and the Bright-Glo luciferase assay kit according to the manufacturer's instruction. The stable clones with inductivity above forty (40) folds were used as target cells for creating the RHGP libraries.

Construction of the RHGP gene search vector, pRHGP22. The RHGP gene search vectors, pRHGP22 was constructed using pLEST vector as a backbone from Cohen's lab (17, Lu, 2004). The DNA sequence of $Neo^R$-TRE-CMV in pLEST was first replaced with a expression cassette of pTRE-Tight-CMV-Blasticidin$^R$. The 3' UTR WPRE element was removed and the p15A ori-Chloramphenicol acetyltransferase (CAT)

resistant gene was inserted in the same site. Two LoxP sites were inserted into down stream to the Blasticidin$^R$ gene and up stream to the p15A ori-CAT, respectively. The LoxP sites along with the Cre recombinase will allow us to reversibly validate the phenotypes by excising the TRE-CMV promoter from the chromosome.

Production of RHGP virus and Construction of RHGP libraries. The RHGP lentiviruses were produced using Invitrogen's ViroPower Lentiviral Expression System. The cells of 293FT were plated in 10-cm plates at about $1-2 \times 10^6$ cells per plate, respectively. After 24 hours incubation, the cells were transfected with 3 µg of RHGP22 vector and 9 µg of ViraPower Packaging Mix using Lipofectimine 2000. The medium was changed with the fresh transfection medium after 5 hours incubation at 37° C. After 48 hours incubation, the viruses in medium were collected and filtrated through a 0.45 µm filter. The lentivirus was tittered according to the manufacturer's instruction.

To construct the RHGP library, the MDCK/Tet-off cells were plated in 150-mm plates at $2 \times 10^6$ cells per plate, respectively a day before harvesting the RHGP viruses. Next day, the cells ($4.6 \times 10^6$ cells per plate) were washed with 10 ml of PBS and transduced with 10 ml of freshly harvested RHGP viruses with at 6 µg/ml of polybrene. The cells were incubated at 37° C. for 2 hours and mixed every 20 minutes by rocking. After 2 hours incubation, the medium was replenished with 10 ml of transduction medium. Twenty-four hours post-transduction, the cells were washed with 10 ml of PBS followed by infection with influenza virus A/Udorn/72 at MOI of 0.1 for 2 hours in 5 ml of infection DMEM medium containing 0.2% of BSA, 200 µg/ml of hygromycin and 6 mg/ml of Blasticidin. The cells were mixed by gently rocking every 15 minutes. After 2 hours infection, the cells were added 15 ml of infection medium. After 24 hours post-infection, the cells were washed with PBS and infected with influenza virus A/Udorn/72 again at the same MOI. Two days after the second round of infection, the cells were washed with 10 ml of PBS and added 20 ml of 50% condition media containing 200 µg/ml of hygromycin and 6 µg/ml of blasticidin. The medium was changed every 3 days until the untransduced cells were killed and the virus resistant colonies were formed. Two weeks after second round of infection, the visible individual colonies were picked and subcultured in 24-well plates.

Reversibility assay for influenza virus resistant cell clones. To verify the reversibility of the influenza virus resistant clones, the phenotypes and the parental MDCK/Tet-Off cells were cultured in absence or presence of Dox for 3 days. The cells were plated in 100-mm plates at $2 \times 10^6$ cells per plate and cultured with or without Dox. After 24 hours, the cells were infected with influenza virus A/Udorn/72 at MOI of $1 \times 10^{-2}$ and $1 \times 10^{-5}$, respectively. After 3 days incubation, the cells were subjected to the crystal violet staining.

Identification of the candidate genes from influenza virus resistant clones. Typically, $1-10 \times 10^6$ cells of each clone were collected and washed once with PBS solution. The cell pellet was resuspended in 10 ml of lysis buffer containing 0.32 M Sucrose, 10 mM Tris pH 7.5, 5 mM $MgCl_2$ and 1% Triton X-100. The lysate was centrifuged at 1500×g for 15 minutes. The pellet was treated with 100 µg of proteinase K in 0.5 ml of proteinase K buffer containing 25 mM EDTA, 150 mM NaCl and 40 mM Tris pH 7.5 followed by addition of 0.5% SDS. The mixture was incubated overnight at 37° C. The proteinase K treated lysate was added 50 µg of RNase A and incubated at 37° C. for 2-4 hours. The genomic DNA was extracted twice with phenol/isoamyl alcohol/chloroform followed by precipitation with equal volume of isopropanol. The DNA pellet was washed with 70% ethanol and dissolved in 200 µl of TE (pH 7.5) buffer.

Genomic DNA (10 µg) in 250 µl was digested with restriction enzyme BamHI or XbaI for 2-4 hours. The digested DNA was extracted with phenol/isoamyl alcohol/chloroform, precipitated with ethanol and dissolved in 30 µl of TE buffer. The digested DNA (2.5 µg) in 250 µl was self-ligated overnight with 20 units of T4 ligase at 16° C. The ligated DNA was precipitated with ethanol and washed with 70% ethanol. The DNA pellet was dissolved in 20 µl of TE buffer and electroporated into DH10B ElectroMax competent cells. The colonies (8-16) from each ligated DNA were picked for plasmid DNA preparation and digestion with the restriction enzyme for size analysis. The candidate plasmid DNA was further used to identify the target genes involved in the phenotype by DNA sequencing and genome mapping.

Validation of host target genes with siRNA. The human duplex siRNA homologues for candidate gene MRPL42, COX5A, SLC25A25 and TAPT1 were prepared as siGENOME SMART pool by the manufacturer. The siRNA NP-1496 sequence [SEQ ID NO.: 13](GGAUCUUAUUU-CUUCGGAGUU) against the nucleocapsid (NP) gene of influenza virus was used as a positive control (18, Ge, 2003). The non-targeting siRNA, siCONTROL 1 was used as negative control. The HEK293 cells were plated in 24-well plates at $1 \times 10^5$ cells per well, respectively. After 24 hours incubation, the cells were transfected with 20 nM of siRNA and 1.5 µl of TransIT-TKO, according to the manufacturer's instruction. The cells were re-transfected with siRNA after 24 hours incubation. Twenty-four hours after second round of transfection, the cells were washed with 0.5 ml of MEM followed by infection with influenza virus A/Udorn/72 at MOI of 1.0 in 300 µl of DMEM and 0.05% FBS. The cells were incubated for 1 hour with gently rocking every 15 minutes. The cells were washed twice with MEM and added 0.5 ml of infection medium for virus production. The medium from each well was collected at 24 or 48 hours of post-transfection. The progeny viruses in the medium were tittered by plaque assay.

RESULTS

Construction of the RHGP Cellular Library

RHGP seeks to interrogate the entire cell genome to evaluate both over-expression and knockout events. This challenge requires the creation of an RHGP library with enough integration events to ensure coverage of the host whole genome. It is also important that the library be limited to a single RHGP integration event per cells to preclude complications arising from multiple perturbations of the same cells. As the average gene size in the human genome is estimated to be 27 kb (19), we calculated that $10^5$ independent integration events are required to ensure random coverage of the whole genome (one vector insertion per gene). Prior studies with RHKO focused on MMLV-based integration vectors (16) but the titer of these vectors is generally limited to $10^3$ transducing units (TU) per mL. To improve the efficiency of the approach, a lentiviral system was developed. As outlined in the Materials and Methods, pRHGP22 was constructed using an improved expression cassette consisting of a pTRE-Tight-CMV promoter driving a Blasticidin resistance gene, which provided a selectable marker under strict inducible control. An ori-chloramphenicol acetyltransferase (CAT) resistance gene provided an independent reporter and to rescue the host genomic DNA to identify the target gene and site of vector integration.

Screening the Influenza Virus Resistant Phenotypes

To identify targets that render host cells resistant to influenza, an RHGP library was generated in MDCK cells. This particular cell model was selected based on its well-established responsiveness to influenza infection. Following library construction via transduction with the pRHGP22 vector, an RHGP cellular library was created, ensuring 100-fold coverage of the human genome. To minimize the potential for multiple insertions within a single cell, a low MOI (0.15) was employed during the transduction of the target cells for RHGP library preparation.

The MDCK cell library was selected using an otherwise lethal concentration of blasticidin (administered 24 hours post-infection) to ensure vector integration. The library was also challenged by infection with influenza A/Udorn/72 (at a relatively high MOI of 0.1) to select for influenza-resistant cells. To ensure thorough elimination of influenza-susceptible cells, the cultures were subjected to multiple rounds of influenza infection. As a control, a matched control was included that lacked the RHGP transduction, but was otherwise treated identically. In general, after the second round influenza challenge, no surviving cells were detected in the matched control. Thereafter, the surviving cells in the RHGP-transduced group were cloned and expanded, yielding approximately 3,000 clones per study (Table 2). From these, a total of 194 individual colonies were isolated from a single library for further analysis. To ask that the individual clones retained the influenza-resistant phenotype, these were re-challenged with influenza. The re-challenge study allowed us to de-prioritize clones that were somewhat susceptible to influenza challenge and a subset of 14 highly-resistant clones was selected for further characterization Reversibility Assay of the Virus Resistant Clones A key feature of the RHGP technology is the ability to validate candidate targets via regulation by an inducible promoter. This allowed us to eliminate any candidate clones that might have become resistant to influenza as a result of spontaneous mutation or other artifacts of the infection assay. Specifically, the promoter for the RHGP vector incorporated into the influenza-resistant clones was under the control of a Tet-off system. Therefore, in the presence of exogenously-added tetracycline (Tet) or doxycycline (Dox), the RHGP vector can be "turned off". This feature allowed us to de-prioritize those candidates that remained resistant to influenza when challenged in the presence of exogenously-added Dox. In the course of these studies, we considered that influenza resistance at a high multiplicity of infection (MOI) might favor targets or pathways associated with early stages of the influenza life cycle whereas a low MOI might favor mechanisms required for later stages of the influenza life cycle. Thus, influenza challenge was conducted at two widely different multiplicities of infection ($10^{-5}$ or $10^{-2}$) to exclude the possibility that the assay system might bias for either early or late stage mechanisms of viral resistance. Cell viability was determined by staining with crystal violet at 72 hours post-infection. Control cells lacking an RHGP integration event provided a positive control for virus-mediated killing of host cells. Of the 14 clones analyzed, 12 (86%) regained sensitivity to influenza in the presence of Dox and the remaining 2 were de-prioritized for further investigation.

The RHGP gene search vector was designed to efficiently locate target genes and determine the orientation (sense or antisense) of the integration event. Specifically, the gene search vector encodes for a CAT reporter gene which can be rescued by restriction enzyme-based genomic DNA cloning. Genomic DNA was isolated from those clones that were validated to demonstrate Dox-mediated reversibility of the influenza resistance. The genomic DNA was digested with suitable restriction enzymes and self-ligated to derive circularized vector-genomic DNA. These constructs were used to transform $E$ $coli$ and chloramphenicol-resistant subclones were isolated and sequenced. To confirm the genomic sites of the vector integration, at least 8-16 different chloramphenicol resistant colonies were isolated and sequenced from each MDCK clone. The resulting genomic DNA sequences flanking the RHGP vector insertion sites were subjected to genome mapping against the canine genome using standard search algorithms. Consistent with the experimental design, most targets consisted of a single integration site per MDCK cells. However, some clones contained multiple integration events, which could have arisen as a result of multiple RHGP integration sites or if that particular candidate had consisted of multiple clones. In addition, we were unable to isolate candidate genes from a small subset of other candidates due to technical limitations. Altogether, genomic DNA cloning identified a total of 70 different target genes that related to influenza resistance.

Validation of Target Genes Using Naive Cells

RHGP identified a series of targets that conferred resistance to influenza infection and the reversibility of the phenotype validated the applicability of the targets within the experimental system. We also sought to verify these candidates using an independent experimental system to exclude the potential for unexpected outcomes that might be unique to RHGP the choice of the host cell system (MDCK) or the influenza variant (Udorn virus).

As an independent confirmation of the targets identified using RHGP, a subset of these targets was selected to be tested using more conventional approaches. Specifically, we emphasized targets, where decreased expression related to influenza resistance since, in part, knock-down targets may be amenable to future targeting strategies to comparably knock down expression or function using small molecule or biologics-based therapies. Importantly, while the results from MDCK cells identified canine targets, the siRNAs were designed against the human homologue of target genes. The duplex siRNAs were generated for 4 such targets (MRPL42, COX5A, TAPT1 and SLC25A25) and were used to transfect HEK293 cells. Since influenza is generally not toxic to HEK293, measurements of viral titers served as the endpoint to assess efficacy. For our first series of studies, the siRNA-treated 293 cells were infected with the same strain of influenza used for the RHGP studies (A/Udorn/72). Following challenge with Udorn, viral titers were assessed, demonstrating lower levels of virus in siRNA-transfected cells. In light of recent evidence for artifact-based effects of siRNA on the elaboration of cytokines, parallel studies were conducted with irrelevant siRNA constructs, thus verifying the specificity of the antiviral effect for the targets of interest.

After validating the findings using Udorn, we then extended the results to other influenza variants. For example, siRNA also conferred resistance to a distinct strain of influenza, A/WSN/33 and comparable findings were obtained at different multiplicities of infection. Altogether, these findings validate the application of RHGP to identify novel host-based targets and suggest the potential for broad-spectrum application to different forms of influenza.

In this example it is shown that RHGP can provide an efficient means to conduct genome-wide screening of any host factor required for influenza virus infection, including targets that have been over-expressed or knocked-down and validate these targets using internal elements within the RHGP vector. This genome-wide screen prioritized MRPL42, COX5A, TAPT1 and SLC25A25 protein as effective host-oriented targets for influenza and the efficacy of these targets was further validated in independent studies using conventional siRNA approaches.

One unique aspect of our present study is the use of an improved form of RHGP. Previous studies had employed MMLV-based vectors to inhibit both copies of a gene in diploid cells. However, the MMLV vector was intrinsically limited low titers of production and we demonstrate that a lentiviral system overcomes the previous limitations. The resulting system was sufficient to ensure a 100-fold coverage of the entire human genome which is important for conducting thorough assessments of both over-expressed and knocked-down targets. Furthermore, the use of a lentiviral vector strongly favors single site insertion into sites of active gene transcription, which increases the efficiency of the screening procedure.

Figure 9A:
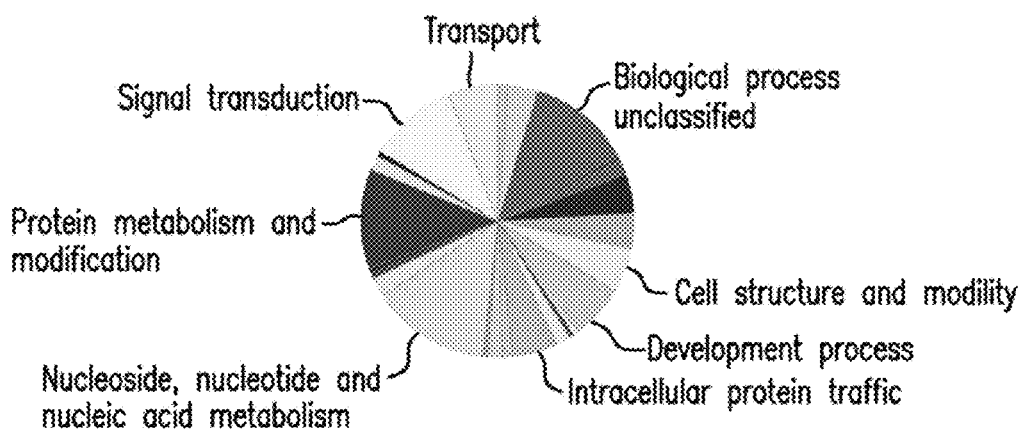
In FIG. 9A, classification is made by biological processes, where the nature of the process is set forth. In Panel B, classification is achieved via molecular function, with the function being set forth.
Figure 9B:
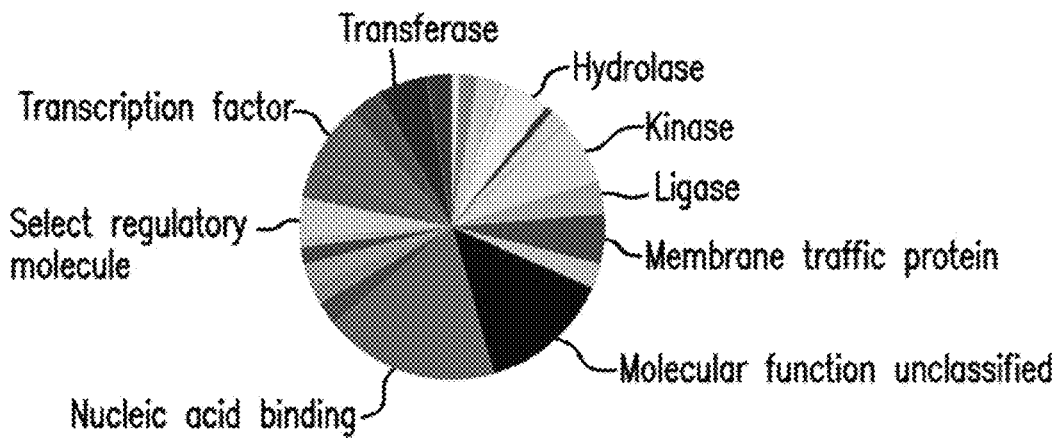
FIG. 9 is a chart showing classification of RHGP-identified influenza targets by biological processes and molecular function.

One distinct advantage is that RHGP is not biased by prior knowledge of the target and identified target genes have often not yet been annotated. Nonetheless, we analyzed the human homologues of the RHGP-influenza genes with the PAN-THER Classification System (Mi, 2005) to identify putative biological pathways. These targets were broadly classified into the categories of biological processes and molecular functions (FIG. 9). Of the 70 targets, 61 (87%) could be classified and 9 (13%) could not. Those 61 genes identified 7 major biological processes and 8 major molecular functions. Prominent among the biological processes were pathways associated with nucleic acid and protein metabolism, signal transduction and intracellular protein trafficking. Specifically, the target functions included intrinsic activities associated with binding to nucleic acids, enzymatic activities (kinases, ligase, hydrolase, Redox), cell signaling and intracellular transport. Early indications suggest these target classes are not random since the frequency of kinase, membrane traffic protein, ligase, hydrolase and transfer/carrier protein identified herein were at least 3 fold higher than would be expected if conducting a random search of known target classes.

Increasing evidence has supported the concept of host-oriented therapeutics for viral diseases. In particular, a series of recent siRNA-based studies have been conducted to identify host targets associated with infection by influenza, HIV or West Nile virus. siRNA is increasingly utilized for target discovery but is intrinsically by the need for robust and sustained over-expression of the siRNA and the outcomes of some siRNA findings have been clouded by concerns about how the technology itself might otherwise alter cell behavior. In particular, recent reports that siRNA could alter cytokine expression is particular problematic for applications to infectious disease. We believe RHGP may provide an improved alternative since it is not limited by these same constraints. Indeed, most (73%) of the targets and pathways identified herein are novel. This outcome likely reflects the fact that RHGP also has the capacity to identify targets that have not yet been annotated as well as proteins or domains that are over-expressed. In contrast, siRNA approaches are generally limited to the knock-down of known or annotated targets. Interestingly, 27% of the targets or pathways identified herein using RHGP interrogation of MDCK cells have some relationship (in terms of sequence, protein families or mechanistic pathways) to genes linked with HIV or West Nile infection of human cells (Table 3). This observation suggests that different viral pathogens convergently evolved to share certain critical host pathways and these pathways are often conserved among different mammalian species (e.g., dogs and humans). Notably, the genes identified herein are less similar to the recent influenza study. We postulate that this seeming discrepancy represents that fact that the previous study with influenza utilized a *Drosophila* cell line, which is important because the fruit fly is more genetically distinct from mammalian cells and because the *Drosophila* genome is limited to approximately 14,000 genes, fewer than the human or canine genome.

Figure 10:
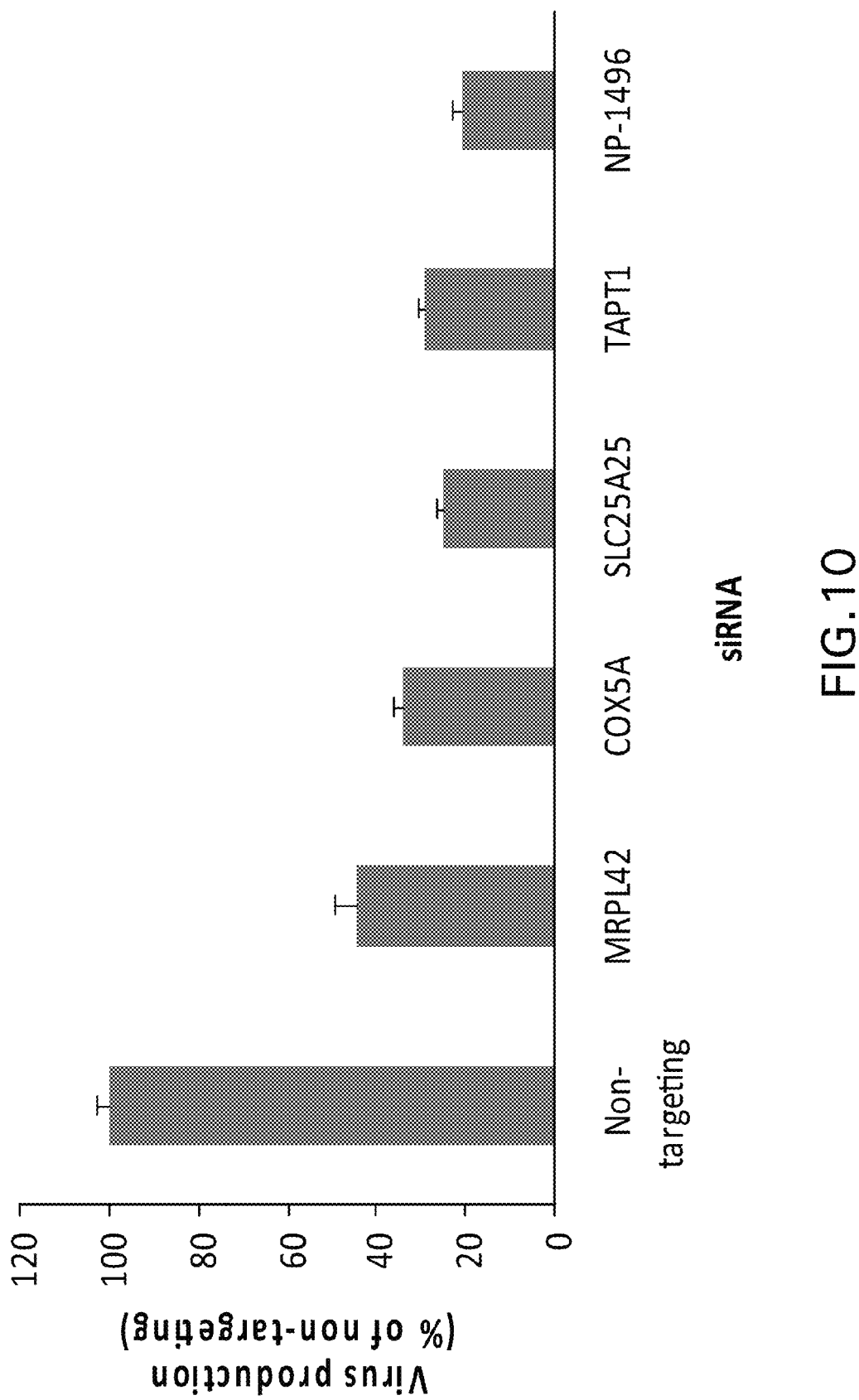
FIG. 10 is a graph reflecting the reduction in viral production caused by inhibition of therapeutic targets identified by RHGP.

Further investigation reveals potential mechanistic information linking some of the targets identified using RHGP with viral infections. For example, decreased MRPL42, COX5A, TAPT1 and SLC25A25 expression decreases susceptibility to influenza infection (FIG. 10). MRPL42 is a mitochondrial ribosomal protein, encoded by a nuclear gene, involved in mitochondrial protein synthesis. A recent report demonstrated that introduction of SIV-Nef in $CD4^+$ T cells stimulated expression of related host mitochondrial ribosomal proteins, MRPL1, MRPL14 and MRPL19. This report suggested up-regulation of these factors may facilitate the production of viral messages required at later stages of the viral life cycle. If correct, our present results extend this finding to MRPL42 and indicate that influenza might utilize a similar mechanism. A similar finding links another target identified herein, COX5A with a viral infection COX5A is one component of the cytochrome C oxidase (COX) complex and a different subunit, COX6A1, reportedly is required for influenza virus replication. Interestingly, the transmembrane protein TAPT1 (Transmembrane anterior posterior transformation 1) required for axial skeletal patterning during development in vertebrate embryos was uncovered that part of the gene encodes the HCMV gH receptor identified by screening of cDNA expression libraries with monoclonal antibodies against the gH receptor. Although the mechanism how TAPT1 was involved in the pathogenesis remains unknown, it is possible that the TAPT1 may also be involved in influenza virus infection. The SLC25A25 (Solute carrier family 25, member 25) protein is a member of the super family of mitochondrial and phosphate carrier. A number of similar proteins in the super family have been reportedly involved in HIV and WNV infection.

In addition to gene inactivation, RHGP-induction of other genes decreases influenza susceptibility. Prominent among these are B-cell CLL/lymphoma 2 (BCL2) and plasminogen activator urakinase (PLAU) gene. The proto-oncogene, BCL2, is a well-characterized regulator of cell survival and recent report have linked BCL2 with the regulation of cell survival following apoptosis caused by Sindbis, influenza viruses or HIV-1. Likewise, RHPG also linked overexpression of the PLAU serine protease with influenza. Notably, the amino-terminal fragment of PLAU was recently shown to suppress the assembly and budding of HIV-1 from infected cells (Wada, 2001). Genomic correlations have also linked PLAU and its receptor, PLAUR, with infection by human respiratory syncytial virus.

EXAMPLE 3

Further Identification of Potential Influenza Targets Using RHGP

Using techniques very similar to those set forth in Example 2 above, additional potential targets for therapeutic intervention to prevent or treat infection with influenza virus were identified.

MATERIALS AND METHODS

Chemicals and cell culture. MDCK cells, human 293HEK cells and MEM medium were purchased from the American Type Culture Collection (ATCC). Influenza virus A/Udorn/72 was purchased from Charles River Lab. All siRNA oligonucleotides were synthesized by Dharmacon Research.

Construction of pTet-Off transactivator vector and the MDCK/Tet-off stable cell lines. The pTet-Off transactivator vector was constructed using pIREShyg3 (Clontech) as a backbone. A PCR-generated tTA fragment was inserted into the BamHI and SofI sites of the pIREShyg3 vector to generate the pTet-Off transactivator vector, pIREShyg3-tTA.

To create MDCK/Tet-Off cell lines, $2 \times 10^6$ MDCK cells were cultured in 10 cm plates and transfected with 10 ng pIREShyg3-tTA vector using Fugene 6 (Roche). Twenty-four hours post-transfection, log-phase cultures of MDCK cells selected using 200 ng/mL hygromycin and the medium was changed every 3 days until all controls cells were killed. Hygromycin resistant clones were screened for the Doxycylcine (Dox; Invitrogen) induction activity using pTRE-luc (Clontech) vector and the Bright-Glo luciferase assay kit (Promega). Stable clones with at least 40-fold induction were used to create RHGP libraries.

Construction of the RHGP gene search vector, pRHGP22. The RHGP gene search vector, pRHGP22 was constructed using the pLEST vector as a backbone (provided by Dr. Stanley Cohen, Stanford) (Lu et al., 2004). The pTRE-Tight-CMV-Blasticidin$^R$ was substituted as the promoter. The 3' UTR WPRE element was removed and the p15A ori-Chloramphenicol acetyltransferase (CAT) resistant gene was inserted at the same site. Two LoxP sites were inserted downstream from the Blasticidin$^R$ gene and upstream from the p15A ori-CAT, respectively.

Production of RHGP virus and Construction of RHGP libraries. RHGP lentiviruses were produced using ViroPower Expression System (Invitrogen). HEK293FT cells were plated in 10 cm plates at $10^6$ cells per plate. After 24 hours incubation, the cells were transfected with 3 µg RHGP22 and 9 µg ViroPower Packaging Mix using Lipofectimine 2000 (Invitrogen). The medium was changed after 5 hours incubation at 37° C. After 48 hours, viruses in the culture medium were filtrated through a 0.45 µm filter and tittered according to the manufacturer's instruction.

To construct the RHGP library, MDCK/Tet-off cells were plated in 15 cm plates at $2 \times 10^6$ cells per plate. The next day, the samples were washed with PBS and transduced with RHGP viruses in 6 µg/mL polybrene. The samples were incubated at 37° C. for 2 hours with mixing prior to replacement with fresh media. Forty-eight hours post-transduction, the cells were washed with PBS and infected with influenza virus A/Udorn/72 at a multiplicity of infection (MOI) of 0.1 for 2 hours in DMEM medium containing 0.2% BSA, 200 µg/mL hygromycin, 2 µg/mL bovine trypsin and 6 µg/mL Blasticidin with gentle mixing every 15 minutes. The media was then replenished with MEM. After two days, the cells were washed with PBS and infected again with influenza virus as indicated above. After the second round of infection, the samples were washed with PBS and incubated in conditioning media containing 200 µg/mL hygromycin and 6 µg/mL blasticidin. The medium was changed every 3 days until all non-transduced cells were killed and the virus resistant colonies had formed. Two weeks after second round of infection, the visible individual colonies were isolated and subcultured in 24-well plates.

Reversibility assay for influenza virus resistant cell clones. To verify reversibility of RHGP event, the MDCK/Tet-Off cells were cultured in absence or presence of Dox for 3 days. The cells were plated in 10 cm plates at $2 \times 10^6$ cells per plate and cultured with or without Dox. After 24 hours, the samples were infected with influenza virus A/Udorn/72 at MOI of $1 \times 10^{-2}$ and $1 \times 10^{-5}$, respectively. After 3 days, surviving cells were stained with crystal violet to visualize the remaining cells.

Identification of the candidate genes from influenza virus resistant clones $1 \times 10^6$ cells from each clone were suspended in lysis buffer containing 0.32 M Sucrose, 10 mM Tris pH 7.5, 5 mM $MgCl_2$ and 1% Triton X-100. The lysate was centrifuged at 1500×g for 15 min and the pellet was treated with 100 µg of proteinase K (Sigma) in proteinase K buffer containing 25 mM EDTA, 150 mM NaCl and 40 mM Tris, 0.5% SDS, pH 7.5. The mixture was incubated overnight at 37° C., treated with 50 µg RNase A (Sigma) and incubated at 37° C. for 2 hours. Genomic DNA was extracted with phenol/isoamyl alcohol/chloroform followed by precipitation with isopropanol. The DNA pellet was washed with 70% ethanol and dissolved in TE buffer (pH 7.5).

Genomic DNA (10 µg) was digested with restriction enzyme BamHI or XbaI, extracted with phenol/isoamyl alcohol/chloroform, precipitated with ethanol and dissolved in TE buffer. Digested DNA (2.5 µg) was self-ligated overnight using T4 ligase (Invitrogen) at 16° C. The ligated DNA was precipitated with ethanol and washed with 70% ethanol. The DNA pellet was dissolved in TE buffer and electroporated into DH10B ElectroMax competent cells (Invitrogen). Multiple colonies were isolated for plasmid DNA preparation and restriction enzyme digestion. The plasmid DNA was further used to identify the target genes by DNA sequencing and genome mapping.

Validation of host target genes with siRNA. The human duplex siRNA homologues for candidate gene MRPL42, COX5A, SLC25A25 and TAPT1 were prepared as recommended by the manufacturer. The siRNA NP-1496 sequence [SEQ ID NO.: 13] (GGAUCUUAUUUCUUCGGAGUU), which targets the nucleocapsid (NP) gene of influenza virus, provided a positive control (Ge et al., 2003). Non-targeting siRNA, siCONTROL1 provided a negative control. HEK293 cells were plated in 24-well plates at $1 \times 10^5$ cells per well, respectively. After 24 hours incubation, the cells were transfected with 20 nM of siRNA and TransIT-TKO, according to the manufacturer's instruction (Minis). The cells were re-transfected with siRNA after 24 hours incubation. Twenty-four hours after second round of transfection, the samples were washed with MEM followed by infection with influenza virus A/Udorn/72 (MOI 1). The cells were incubated for 1 hour with gentle rocking every 15 minutes. The culture medium from each well was collected 48 hours post-transfection and progeny viruses in the medium were titrated using standard plaque assays.

RESULTS

Construction of the RHGP Cellular Library

The central feature of RHGP is a unique lentiviral-based genetic element, known as a gene search vector (GSV), which was designed to interrogate the entire genome and identify targets that allow host cells to resist or survive infection with influenza virus. Our experimental strategy centered upon integration of the GSV at a single site in the genome, where it regulated expression of the target gene via an inducible promoter. The vector encoded for a self-inactivating lentiviral LTR, which prevented the GSV from re-emerging from a transduced cell. The RSV E/P promoter was used only for production of the GSV and was eliminated by the integration of the GSV into the host genome.

The GSV could integrate in either a sense or an antisense orientation. In the antisense configuration, the integration event itself inactivated one allele and facilitated expression of an antisense construct, which knocked down genes encoded on the other allele. In this way, RHGP facilitated homozygous perturbation of both gene copies in diploid cells. In the opposite (sense) orientation, RHGP facilitated overexpression of the target gene. This outcome could extend beyond simple overexpression of an entire gene (e.g., insertion upstream of the start site) since integration downstream of the start site could trigger overexpression of domains, which could produce a dominant-negative inhibitor of wild-type gene function. As such, RHGP allowed us to interrogate the entire cell genome to identify different types of events that allow host cells to resist or survive influenza infection.

To facilitate RHGP, a library of MDCK cells was transduced using a lentiviral-based GSV. As the average gene size in the genome is estimated to be 27 kb (Gupta and Varshney, 2004), we calculated that $10^5$ independent integration events would ensure random coverage of the entire genome (Li and Cohen, 1996). As outlined in the Materials and Methods, pRHGP22 was constructed using an expression cassette consisting of a pTRE-Tight-CMV promoter driving a blasticidin resistance gene, which provided a selectable marker under strict inducible control. The library of transduced host cells was then selected using blasticidin and surviving cells were screened for influenza resistance as detailed below.

Screening the Influenza Virus Resistant Phenotypes

To identify targets that render host cells resistant to influenza, an RHGP library was generated in MDCK cells and influenza challenge performed. This particular cell model was selected based on its well-established responsiveness to influenza infection and because the canine genome has been annotated and can be compared with human homologues. We conducted preliminary studies to ensure that MDCK cells were efficiently and entirely killed by A/Udorn/72 under the conditions utilized for selection. This outcome was essential to ensure that surviving cells arose as a result of the RHGP perturbation and not as an artifact of spontaneous resistance to influenza. Following library construction with the pRHGP22 GSV, a library consisting of at least $10^7$ independent MDCK clones was created to ensure 100-fold coverage of the genome. A low MOI (0.1) was employed during the library creation to minimize the transduction of any cell by more than one different GSV. As an additional means of confirming GSV integration, the MDCK library was incubated with a lethal concentration of blasticidin (administered 48 hours post-infection).

The library was challenged by infection with influenza A/Udorn/72 to select for influenza-resistant cells. We had previously established that infection with A/Udorn/72 (MOI of $10^{-1}$) reproducibly killed all MDCK cells within 48 hours. As a control, parallel cultures of mock-transduced cells were treated identically and no survivors were observed after 48 hours. We further sought to minimize artifacts by subjecting surviving cells to multiple rounds of lethal challenge. Thus, the samples were subjected to at least three rounds of influenza challenge, at which time no surviving cells were detected in any of the matched controls.

In the course of these studies, we considered that challenge at a high relative MOI of influenza might bias for certain types of targets. For example, survival at a high MOI might unintentionally favor targets associated with early stages of infection or bias against targets associated with later stage events. To preclude such bias, a parallel series of studies were conducted to compare survival in the context of viral challenge at low titer. For this, the clones were subjected to infection at low initial MOI (MOI of $10^{-5}$). The cultures were then evaluated over time and using multiple rounds of infection to ensure that all cells in the control samples had been killed by influenza.

After selecting for RHGP-transduced cells that survived challenge with influenza, clones were isolated by single cell cloning and expanded, yielding an average of 3,000 clones per experiment. Given the abundance of clones, a subset of 303 different influenza-resistant clones (10% of the total population) was selected at random and subjected to a second round of single cell cloning to ensure clonality (Table 2). These subclones were then subjected to a battery of studies to confirm the phenotype and identify the target genes. Each subclone was tested again for the ability to survive a lethal challenge with influenza. Parental MDCK host cells that had been transduced with an inactive Tet-off GSV provided a matched negative control. 129 different subclones (43% of the initial population) were isolated based on their ability to survive lethal challenge with influenza. Most of the down-selection at this stage resulted from colonies that failed to survive the single cell cloning process.

Reversibility Assay of the Virus Resistant Clones

A key feature of the RHGP technology is the ability to validate candidate targets via regulation by an inducible promoter. This allowed us to eliminate candidates that might have become resistant to influenza as a result of spontaneous mutation or other artifacts not related to RHGP. Since the promoter for the RHGP vector was under control of a Tet-off system, we compared influenza-mediated killing of the candidates in the presence or absence of Doxycycline. This study confirmed that 111 of the 129 surviving clones (86%) demonstrated reversible resistance to influenza challenge. The remaining 18 clones (14%) were de-prioritized to ensure that RHGP, and not unrelated artifacts, was responsible for the influenza-resistant phenotype.

Identification of the Host Gene by Genomic DNA Cloning

The RHGP gene search vector was designed to efficiently locate target genes and determine the orientation (sense or antisense) of the integration event. Specifically, the gene search vector encodes for an Ori-CAT reporter gene, which can be rescued by restriction enzyme-based genomic DNA cloning. Genomic DNA was isolated from the 111 clones that had demonstrated reversible resistance to influenza, yielding a total of 110 target genes (Table I). The resulting genomic DNA sequences flanking the RHGP vector insertion sites were subjected to genome mapping against the canine genome using the UCSC Genome Browser. Consistent with the experimental design, most targets consisted of a single integration site per clone. We were unable to isolate candidate genes from a small subset of candidates due to technical limitations. In addition, a minority of samples contained multiple integration events, which could have arisen as a result of multiple RHGP integration sites or if the subclone had not been clonal. Due to this ambiguity, the genes associated with multiple integration events were de-prioritized for further validation.

Figure 4:
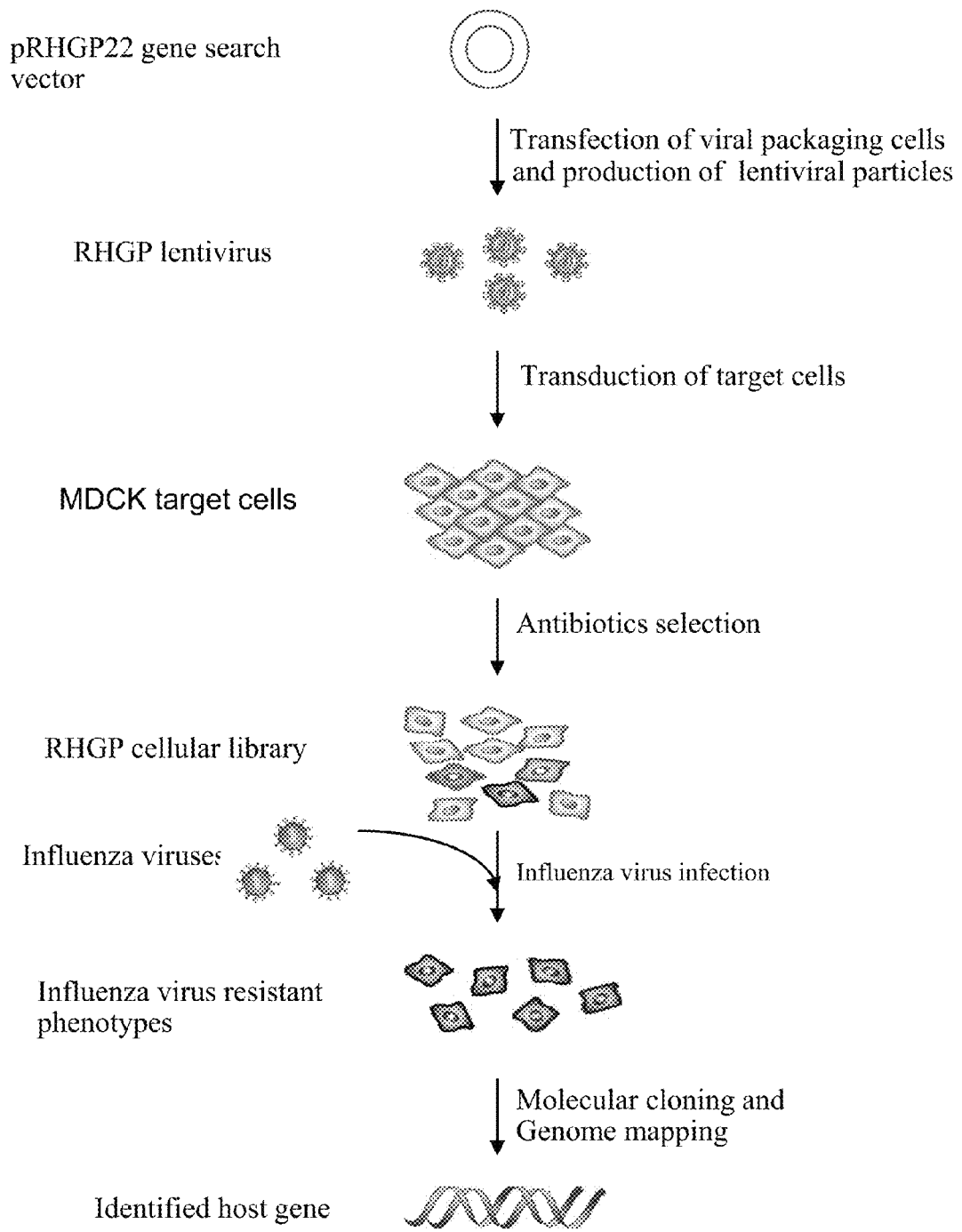
FIG. 4 is a flow chart depicting the steps involved in conducting a full RHGP investigation for influenza-related targets.

The site and orientation of integration offered by RHGP provided insight into the types of perturbations that allowed host cells to survive challenge with influenza (FIG. 4). Specifically, the RHGP perturbations were broadly divided into three groups: (1) "Antisense": Antisense integration events that facilitated disruption of one allele and antisense inhibition of the other allele; (2) "Sense Downstream": Integration in a sense orientation, which would be predicted to facilitate production of one or more domains, which could act as a dominant-negative inhibitor of the full-length gene product; and (3) "Sense-Upstream": Integration in a sense orientation upstream of the start site, which could facilitate overexpression of the entire target gene. Of the 99 known targets identified using RHGP, 56 targets (56% of total targets) represented "Antisense" knockdown of target expression. Another 35% of the targets represented "Sense-Downstream" events, likely conveying overexpression of dominant-negative inhibitors of wild-type gene expression. Consistent with this interpretation, we noted that one particular target, PTBP1, was independently identified as a target in two separate clones; one clone in an "Antisense" orientation and another in a "Sense-Downstream" orientation. The remaining 9% represented "Sense-Upstream" insertions. The orientation of 11 target genes (10% of the 110 targets sequenced herein) could not be ascertained because the gene itself had not been previously described and therefore assignment of orientation was not possible.

In a separate assessment, we asked if these 110 target genes had been linked previously with viral infection. Only four of the 110 targets identified herein (MDN1, GRK6, AKT1 and STXBP1) had been directly linked to viral infection (Table II), suggesting novel information about 106 targets (96%) identified using RHGP. By extending our analysis to related proteins, we found that 23 of 110 targets (21%) identified herein shared homology with or was a co-member of a superfamily with, host targets that had been linked previously with viral infection. These findings suggest RHGP identified novel functions for the preponderance (75%) of the host targets. Two targets identified herein (C4orf32 and C21orf33) had simply been described as open reading frames (orfs), with no function ascribed. Altogether, these findings suggest that RHGP-based interrogation of the host genome had identified both novel targets and/or ascribed novel functions to known genes.

Validation of Target Genes Using Naive Cells

RHGP identified a series of targets in MDCK cells that conferred resistance to influenza infection and the reversibility of the phenotype provided an initial validation for these targets. We then sought to verify these candidates using an independent experimental system to exclude outcomes that might arise as an artifact of the MDCK cells or RHGP technology. Since the targets genes had been isolated from canine-derived MDCK cells, we identified their human homologues and expressed siRNAs selective for these targets in human HEK-293 cells.

RHGP identified modifications that prevented influenza-mediated killing of host cells including targets that have been over-expressed or knocked-down. We were able to validate these targets using an inducible promoter within the RHGP vector to reverse the phenotype, thereby minimizing the potential for spontaneous artifacts that were not attributable to the RHGP strategy. This genome-wide screen allowed us to identify 110 novel targets that render host cells resistant to an otherwise lethal challenge with influenza virus. Of these targets, most (106 of 110) had not been previously linked with influenza. In addition, we ascribe novel functions to previously-unknown genes and orfs. As proof of concept, a subset of targets was further validated in independent studies using conventional siRNA approaches.

A recent series of siRNA-based studies identified host targets associated with infection by influenza, HIV, or West Nile virus (See, Table 3 for summary) (Brass et al., 2008; Hao et al., 2008; Konig et al., 2008; Krishnan et al., 2008). These earlier studies utilized host cells that were derived from different species, which increases the complexities of comparisons with our present findings. Compounding this, siRNA is increasingly utilized for target discovery but is intrinsically limited by the need for robust and sustained over-expression of the siRNA. The outcomes of some siRNA findings have also been clouded by questions of whether the siRNAs might non-specifically alter host defense mechanisms (Kleinman et al., 2008), which could be particularly problematic for applications of siRNA technology to antiviral disease. RHGP might also induce potential antiviral host defense mechanisms. For example, an antisense orientation of the GSV is expected to induce double stranded RNA, which itself can trigger host antiviral responses.

Tables

TABLE 2

Summary of RHGP-Based Discovery of Gene Perturbations that RenderHost Cells Resistant to a Lethal Challenge with Influenza Virus

| Property | Frequency |
|---|---|
| Influenza-resistant clones selected for continued investigation | 303 |
| Clones retaining influenza-resistant phenotype | 129 of 303 (43%) |
| Clones validated via RHGP reversibility | 111 of 129 (86%) |
| Targets Sequenced | 110 of 111 (99%) |
| Targets with demonstrated links to viral infection | 4 of 110 (4%) |
| Targets related to other genes with links to viral infection | 23 of 110 (21%) |
| Targets with no known links to viral infection | 83 of 110 (75%) |
| Targets not yet annotated | 11 of 110 (10%) |

Table 2. Shown is an overview of the progression of events associated with the RHGP-mediated identification of host targets that allow host cells to resist an otherwise lethal infection with influenza. Please note that the majority of specific targets (96%) and target families (75%) identified using RHGP were unique. RHGP also facilitated identification of targets that had net been annotated.

TABLE 3

Comparison of Common Families of Host-Oriented Targets Identified Using RHGP Versus siRNA Approaches.

| Influenza RHGP | Influenza Hao et al. 2008. Nature 454, 890 | HIV Brass et al. 2008. Science 319, 921 | HIV Konig et al. 2008. Cell 135, 49 | WNV Krishnan et al. 2008. Nature 455, 242 |
|---|---|---|---|---|
| N4BP2 | | | Nedd4 | NDFIP1 |
| MRPL42 | MRPL12 | | MRPL10 | |
| HERC6 | | | | HERC1 |
| SLC25A25, SLC30A9 | | SLC46A1 | SLC35A2 | SLC39A11, SLS9A3 and SLC16A4 |
| LSM4 | | LSM3 | | LSM8 |
| CSNK1D | | | | CSNK2A1 |
| COX5A | COX6A1 | | COX6B2 | |
| RAD51L1 | | | RAD21 | RAD51 |

TABLE 3-continued

Comparison of Common Families of Host-Oriented Targets
Identified Using RHGP Versus siRNA Approaches.

| Influenza RHGP | Influenza Hao et al. 2008. Nature 454, 890 | HIV Brass et al. 2008. Science 319, 921 | HIV Konig et al. 2008. Cell 135, 49 | WNV Krishnan et al. 2008. Nature 455, 242 |
|---|---|---|---|---|
| NDUFAF2, NDUFA7 | | NDUFB7 | | |
| MDN1 | | MDN1 | | |
| VPS34 (PIK3C3) | | VPS53 | | VPS33A |
| PKD2L2 | | PKD1L2 | | |
| SF3A3 | | | SF3A1, SF3B1 | |
| DDX17, DDX58 | DDX42 and DDX28 | DDX53, 55, 10, 3X | DDX23 | |
| GRK6 | | | | GRK6 |
| AKT1 | | AKT1 | | |
| LRRC16A | | LRRC8D | | |
| HEATR7A | | HEATR1 | | |
| CHM | | | | CHML |
| ADAM20 | | ADAM10 | | |
| STXBP1 | | | STXBP1 | |
| COG5 | | COG2, 3, 4 | | |
| ZNF7 | | ZNF12 | ZNF148 | ZNF214 |
| ARID1B | | | ARID1A | |

Table 3. Shown is an assessment of targets and target families identified using RHGP (this report) or siRNA. This Table is limited to target families common to both the current study and published findings (as indicated). While four targets (MDN1, GRK6, AKT1 and STXBP1 in bold) were shared, the remainder were unique, though some related superfamily members have been linked with infection by different viruses. Not shown are the 87 additional targets identified herein that had not commonality with previously-published information.

EXAMPLE 4

RHGP is Used to Identify Potential Targets for Controlling HIV Infectivity

Human Immunodeficiency Virus (HIV-1) is a global threat to public health. Current medicines that directly target the virus often are rendered ineffective in drug-resistant viral variants. An emerging concept to combat drug resistance is the idea of targeting host mechanisms that are essential for the function, survival and propagation of the virus, but not to the host itself. Herein, using Random Homozygous Gene Perturbation (RHGP) on human MT4 T cells, we identified a set of safe and effective host targets that are essential for these cells to survive a lethal infection with HIV-1$_{NL4-3}$. RHGP is a new technology that can sample all targets in a cell. This is possible through the engineering of a gene search vector (GSV), which can randomly integrate into host chromosome. The GSV can up or down-regulate any target in the cell in a reversible manner regulated by an inducer. Reversal of RHGP effect by inducer removal makes the engineered cells sensitive to HIV infection again. Using a siRNA approach, identified defined gene targets were validated and shown to be necessary for infection with either CXCR4 or CCR5 tropic viruses. These studies demonstrate the power of RHGP to identify novel gene candidates including gene sequences without prior knowledge of function (ESTs) for targeted intervention. These candidates are directly suitable for broad-spectrum drug development since gene disruptions during their discovery only exhibit negligible cytotoxicity.

Although Triple cocktail drug therapy (or HAART, Highly Active Anti-Retroviral Therapy) is able to effectively control HIV-1 replication, HAART-resistant HIV-1 strains are relentlessly emerging as a combination of the error-prone HIV viral reverse transcriptase with robust viral replication and incomplete patient compliance. In some areas, viruses resistant to triple drugs used in HARRT were isolated from nearly 20% of AIDS patients (Grant, Hecht et al. 2002; Richman, Morton et al. 2004). Such findings increase the urgency to identify new paradigms for the treatment of HIV-1 disease, especially those with mechanisms of action that are relatively insensitive to the development of resistance. Therapeutics targeting host gene products essential to HIV-1 infection, but not the host itself, could provide such a new modality of treatment since well-designed host targets might not place direct selective pressure on the pathogen.

It is well established that an interplay between the viruses and host cells determines the outcome of viral pathogenesis, ranging from the elimination of viruses to latent and lethal infections. HIV-1 is known to interact with host cellular proteins to aid their replication and evade immune attack. An example of this interplay is demonstrated by individuals who carry a defective cell surface receptor (CCR5) and are therefore resistant to HIV-1 infection (Liu, Paxton et al. 1996). Similar types of interactions have been reported in the literature and encompass nearly every step of HIV-1 life cycle: from viral entry requiring Env binding to the cellular receptor CD4 and coreceptors CXCR4 or CCR5, to the viral release in need of hijacking TSG101 by Gag p6 (Garrus, von Schwedler et al. 2001). Complete documentation of the interaction of HIV-1 proteins with those of the host cell is thus crucial to understanding the process of HIV-1 replication and pathogenesis. More importantly, such understanding could provide a cornerstone to improve therapeutic and prevention strategies to combat HIV/AIDS.

In light of the understood importance of host factors in HIV-1 infection, increasing investigation has begun to consider host targets for antiviral therapy. Host-directed therapeutics has been successfully used in the HIV/AIDS treatment by targeting viral receptor CD4 and/coreceptors CCR5 (Reeves and Piefer 2005; Wheeler, McHale et al. 2007) with biologics and small molecules to impact receptors that are necessary for the HIV binding and internalization. Laboratory investigation and early clinical trials suggest these agents may provide options for the treatment of HIV/AIDS.

Not all host genes discovered are suitable as therapeutic targets, especially those that are essential to the host itself. To distinguish among these targets, our laboratory has employed a novel technology, Random Homozygous Gene Perturbation (RHGP), to select for targets that are essential for HIV infection but which are not necessary for the growth, survival or function of non-infected cells. RHGP was designed to up- or down-regulate any gene in a eukaryotic cell and evaluate the outcome using objective measures of cellular behavior.

Herein, we applied RHGP and identified a set of host-oriented targets that allow host cells to resist lethal HIV infection. These novel targets include those genes whose functions relate to known biological pathways and ESTs whose functions have not been assigned. Identified genes were validated using other genetic approaches including siRNA. Therefore this investigation revealed potential new and safe gene targets for future drug development against HIV/AIDS.

MATERIALS AND METHODS

Cell Lines and Viruses

Cells including MT4, PM1 cells and TZM-b1 and viruses including drug resistant mutant viruses and R5 tropic variant were obtained from NIH AIDS Research and reference Reagent Program. HIV-1$_{NL4-3}$ were made from HEK293 after transfection of proviral DNA (the NIH AIDS program) and amplified in MT4 cells.

HIV-1 Infection and Determination of Infectivity and p24 Production

MT4 or PM1 cells were infected with HIV-1 at MOI of 0.001 by low speed centrifugation (1,200 g) for 1 hour. Supernatants collected post infection were then transferred to the TZM-b1 indicator cell line (Wei, Decker et al. 2002) for examination of infectivity. Relative Luminescence Unit (RLU) was obtained on TZM-b1 cells after they were treated with Bright-Glo Luciferase Assay System (Promega) 3 days later.

P24 amounts in the collected supernatants were also measured using HIV-1 p24 ELISA kit (Xpressbio, Thurmont, Md.) following the manufacturer's instructions.

Construction of the MT-4 R1 Cell Lines

RheoSwitch® Mammalian Inducible Expression System was purchased from New England Biolabs (NEB). Plasmid pNEB-R1 encoding the transactivator R1 was first linearized using restriction enzyme ScaI (NEB). MT4 cells were then transfected by electroporation using Eppendorf Multiporator (Eppendorf, AG 22331, Huammburg) under conditions of 360 v (voltage) and 100 ms (time). MT4 cells were selected using G-418 (400 µg/mL) and G-418 resistant cells were cloned by serial limited dilutions. After expansion, clones were examined at least twice for luminescence (relative luminescence units (RLUs) after transfection with an R1-responsive luciferase reporter gene (pGluc) using Gaussia Luciferase Assay Kit (NEB). We determined the RSL1 induction folds of luminescence from these cell clones as: RLUs obtained from samples in the presence of the inducer divided by RLUs from samples without inducer treatment. The fold from these clones ranged from 2-60 folds. Stable clones (#2-14) with highest induction were used to create RHGP libraries.

Construction of the RHGP Gene Search Vector, pRHGP12-RSN

The RHGP gene search vector, pRHGP12-RSN is one of a series of FGI's RHGP vectors constructed in the company using the lentivirus-based pLEST vector as a backbone (generously provided by Dr. Stanley Cohen, Stanford) (Lu, Wei et al. 2004). This vector was constructed with RheoSwitch Mammalian Inducible System (NEB). The Rheoswitch system contains five copies of the GAL4 response element (5XRE) upstream of a TATA box that results in high induction of transcription with low basal expression in the presence of RSL1 ligand. To construct the vector, the DNA sequence of Neo$^R$-TRE-CMV in pLEST was first replaced with a RheoSwitch (RS) inducible Expression cassette of Ori-CAT-RS opposite to 5'LTR site. The selection marker and reporter cassette containing Blasticidin (BS) resistant gene and an EGFP gene controlled by PKG promoter was inserted in the NheI site in an opposite orientation to the RS expression cassette. Two LoxP sites were inserted into downstream to the RS promoter and upstream to the p15A ori-CAT, respectively.

Production of Lentivirus Carrying GSV and Construction of RHGP Library

RHGP lentiviruses were produced using ViroPower Expression System (Invitrogen). HEK293FT cells were plated in 10 cm plates at $10^6$ cells per plate. After 24 hours incubation, the cells were transfected with 3 µg RHGP22-RSN and 9 µg ViroPower Packaging Mix using Lipofectimine 2000 (Invitrogen). The medium was changed after 5 hours incubation at 37° C. After 48 hours, viruses in the culture medium were filtrated through a 0.45 µm filter and titrated according to the manufacturer's instruction.

To construct the RHGP library, MT4-R1 cells were transduced with RHGP viruses in the presence of polybrene (6 µg/mL) by low speed centrifugation (1,200 g) for 1 hour. To minimize the potential for multiple insertions within a single cell, a low MOI (0.1) was employed during the library creation to minimize the likelihood that cells might be transduced by more than one different GSV. GSV integrated cells were selected using GBL medium (complete RPMI 1640 medium containing G418 (400 ug/ml), blasticidin (4 ug/ml) and RSL1 ligand (0.5 uM)).

Selection of RHGP Cell Clones Survived from HIV-1 Challenge

After infection with HIV-1$_{NL4-3}$, the MT4-R1 RHGP library was cultured in the same GBL medium. The individual surviving clones were established by serial limited dilutions and continuously expanded in GBL medium. Cell clones were further challenged with HIV-1 to confirm their resistance.

Reversibility

To verify reversibility of RHGP event, the viral resistant MT4 cell clones were cultured in the GBL medium or GBL medium without RSL1 for at least 3 days. After HIV-1 infection, viral production (infectivity and p24) in supernatants were examined as described above.

Identification of Candidate Genes from Virus Resistant Clones

The RHGP gene search vector was designed to efficiently discover target genes and determine the orientation (sense or antisense) of the integration event. The gene search vector contains an Ori-CAT reporter gene (FIG. 1), which can be rescued by restriction enzyme-based genomic DNA cloning.

Cells ($1 \times 10^6$) from each clone were suspended in lysis buffer (0.32 M Sucrose, 10 mM Tris pH 7.5, 5 mM MgCl$_2$ and 1% Triton X-100). After centrifugation, the pellet was treated with proteinase K (Sigma) and RNase A (Sigma) in the proteinase K buffer (25 mM EDTA, 150 mM NaCl and 40 mM Tris, 0.5% SDS, pH 7.5). Genomic DNA was extracted with phenol/isoamyl alcohol/chloroform followed by precipitation with isopropanol. The DNA pellet was washed with 70% ethanol and dissolved in TE buffer (pH 7.5).

After digestion with BamHI or XbaI and extraction with phenol/isoamyl alcohol/chloroform, Genomic DNA (10 μg) were precipitated with ethanol and dissolved in TE buffer. Digested DNA (2.5 μg) was self-ligated overnight using T4 ligase (Invitrogen) at 16° C. The ligated DNA was precipitated with ethanol and washed with 70% ethanol. The DNA pellet was dissolved in TE buffer and electroporated into DH10B ElectroMax competent cells (Invitrogen). Multiple colonies were isolated for plasmid DNA preparation and restriction enzyme digestion. The plasmid DNA was further used to identify the target genes by DNA sequencing and genome mapping. The resulting genomic DNA sequences flanking the RHGP vector insertion sites were subjected to genome mapping against the human genome using the UCSC Genome Browser.

Validation of Host Target Genes with siRNA

The human duplex siRNA homologues (siGNOME SMARTpool) for RHGP identified genes were prepared as recommended by the manufacturer (Dharmacon). The siRNA Rab 6A and HIV-1 tat were employed as positive controls (Brass, Dykxhoorn et al. 2008). Non-targeting siRNA (si-CONTROL1) was used as a negative control. MT4 or PM1 cells were cultured in complete RPMI 1640 medium overnight. The log-phase growing MT4 cells were transfected with 1.2 uM of siRNA by electroporation protocol, according to the manufacturer's instruction (Eppendorf). The PM1 cells were eletroporated under the same protocol except using pulse conditions of 200 v (voltage) and 200 ms (time). The cells were infected with HIV-1 variants 24 hours post transfection. Culture media were refreshed everyday and the cell viabilities were examined daily by trypan blue dye exclusion assay. Viral production (infectivity and p24) in supernatants were examined as described above.

RESULTS

Overview of Discovery of RHGP Targeted Gene

As outlined in the Materials and Methods, pRHGP12 was constructed using an expression cassette consisting of a constitutive promoter driving a Blasticidin resistance gene. GSV also contains the Rheoswitch promoter, which can be activated by a ligand. The presence of the ligand (promoter on) can thus produce a host transcript to elicit either up or down regulation of RHGP effect. The gene perturbation effects caused by RHGP was described in detail before (Sui, Bamba et al. 2009). We utilized this resource to interrogate the entire genome of human T lymphocytes to identify targets, whether up- or down-regulated, that allow these cells to survive an otherwise lethal infection with HIV-1.

MT4 T cells were engineered to stably express a transactivator R1, which can activate the built in promoter in RHGP to produce transcripts in the presence of an inducer RSL1. Following transduction with the RHGP vector and antibiotic selection to establish an "RHGP library" of genetic perturbations, the host cells were challenged with a lethal infection of HIV-1.

Survived cells were single cell cloned by limit dilution. To eliminate those survivors that might have arisen as a result of events unrelated to RHGP, the phenotype was confirmed by repeating HIV-1 challenge in the absence of RSL1. This study confirmed that RHGP itself, rather than other artifacts or spontaneous mutations, was directly responsible for cell survival in the face of HIV-1 infection. The genomic DNA from the surviving clones was then isolated and sequenced to identify the target gene as well as the orientation of the GSV integration (to determine if the outcome represents up- or down-regulation of the target.

Construction of the RHGP Cellular Library

A library of MT4-R1 cells with $10^5$ integration events was transduced using a lentiviral-based pRHGP12 GSV to ensure coverage of the host genome. As the average gene size in the genome is estimated to be 27 kb (Gupta and Varshney 2004), we calculated that these $10^5$ independent integration events would ensure random coverage of the entire genome. The library of transduced host cells was then selected using blasticidin. From a particular blasticidin resistant cell clone we found that the GSV was indeed integrated into host chromosome and an antisense transcript was only produced upon treatment of the inducer RSL1 (data not shown). As an additional means of confirming and maintaining R1 expression and GSV integration, the MT4 library was continuously incubated together with a lethal concentration of G418 and blasticidin in the subsequent experiments.

HIV-1 Resistant Clones Survived from Virus-Induced Cell Killing

Figure 11A:
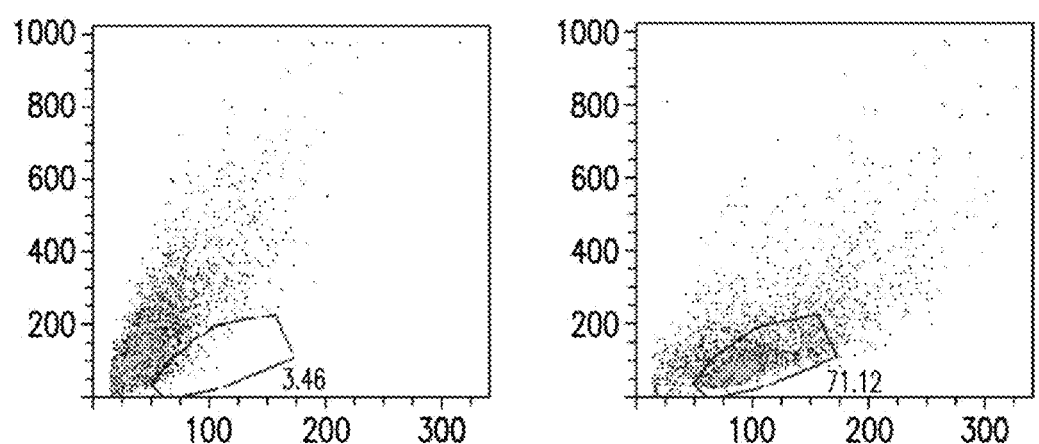
FIG. 11A demonstrates that MT4-R1 cells were killed by HIV-1 within 5 days, and addition of RSL 1 did not affect this killing. (Left panel).

MT4-R1 cells, similar to parental MT4 cells, were efficiently and entirely killed by HIV-1 NL4-3 (at a MOI of $10^{-4}$) within 5 days and addition of RSL1 did not affect this killing (FIG. 11A, left panel). These conditions were strictly utilized for the subsequent selections for survived cell clones in the presence of RSL1 to keep "promoters on". As an additional control, parallel cultures of mock-transduced cells were treated identically and no survivors were observed after 5 days. This outcome was essential to ensure that surviving cells arose as a result of the RHGP perturbation and not an artifact of spontaneous resistance to HIV-1. After cloning and expansion, survived cells were subjected to multiple rounds of infection to eliminate any susceptible cells. In the end we obtained 25 RHGP cell clones that are resistant to virus induced killing. FIG. 11A (right panel) shows survival of such one resistant clone after HIV-1 challenge.

Figure 11B:
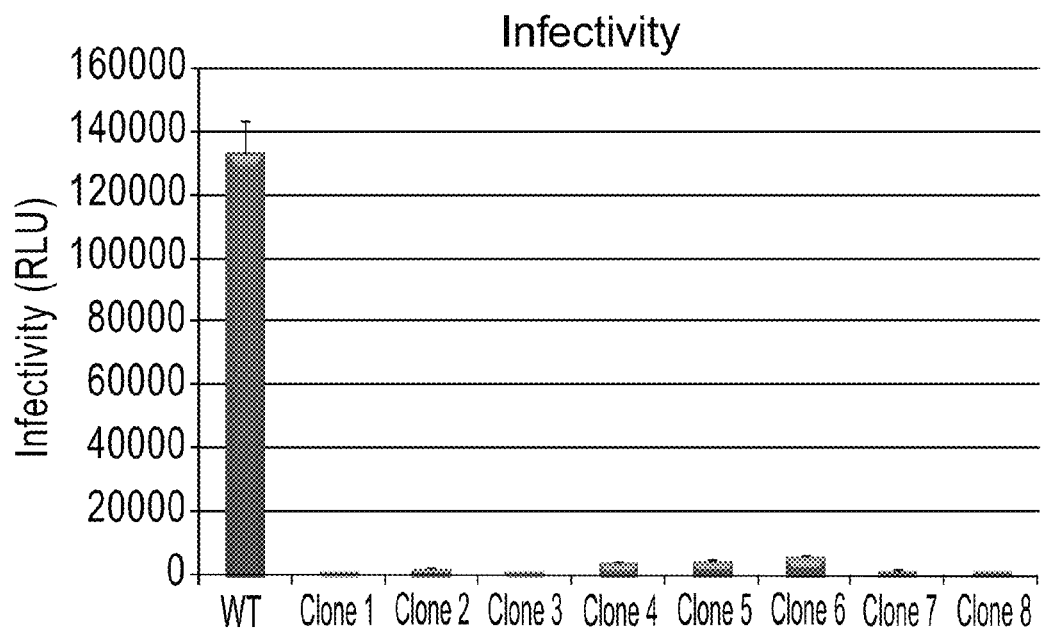
FIG. 11B demonstrates the failure of viral resistant RHGP cell clones to produce and release viruses, while 11C demonstrates that the resistant cell clones also demonstrated resistance in the presence of protease resistant viruses.

In parallel with genomic sequencing, we asked if these resistant cell clones continued to produce infectious viral particles upon HIV infection. After re-challenge of these resistant cell clones with HIV-$1_{NL4-3}$ in the presence of RSL1, the supernatants were collected at 4 dpi and were transferred to the TZM cells, which provide readout of infectivity. FIG. 11B shows a representative experiment that the derived viral resistant RHGP cell clones failed to produce and release progeny viruses. These findings were independently confirmed by determination of p24 in ELISA-based assays.

Figure 11C:
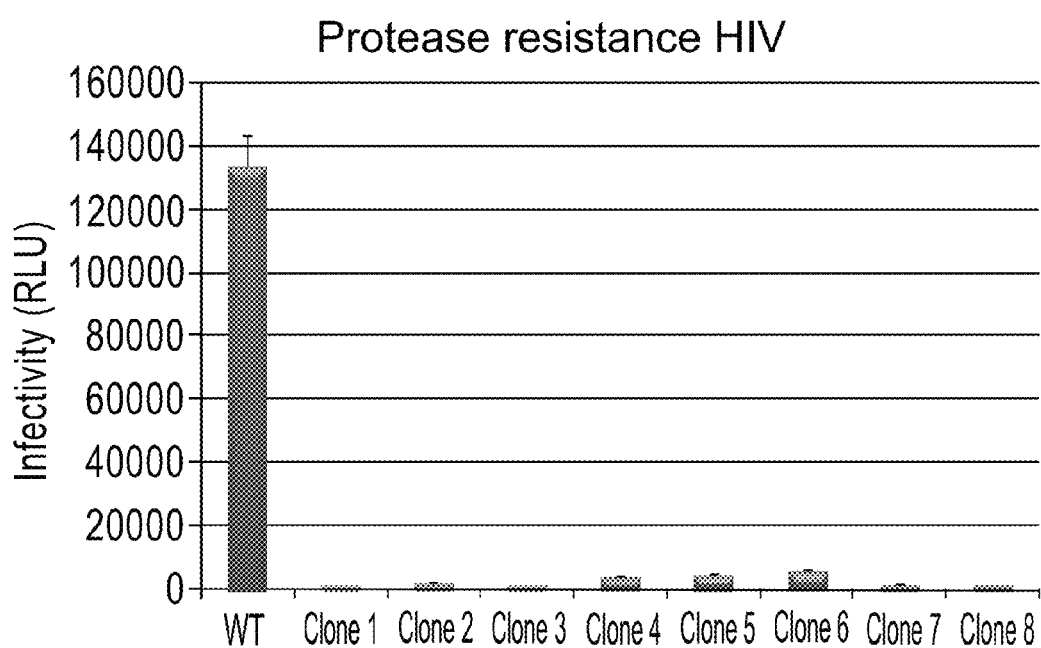
FIG. 11 illustrates the identification of Robo1 as a target for controlling HIV infection.

Although the results with wild-type HIV-$1_{NL4-3}$ were encouraging, we considered that a large unmet need for therapeutics is the application of new targets to viral variants that are resistant to conventional medicines. Therefore, we performed a parallel set of studies with HIV-1 variants with established resistance to protease inhibitors. The RHGP-transduced clones that resisted challenge with wild-type HIV also survived challenge in the face of protease-resistant variants. This outcome was not unique to host cell survival as infectivity assays as well as p24 ELISA confirmed the defective infection by mutant HIV-1 in the resistant cells (FIG. 11C). Together these results confirmed the cell clones we obtained are resistant to infection by both WT and drug resistant HIV-1 variants.

Reversibility Assay of the Virus Resistant Clones

Figure 12A:
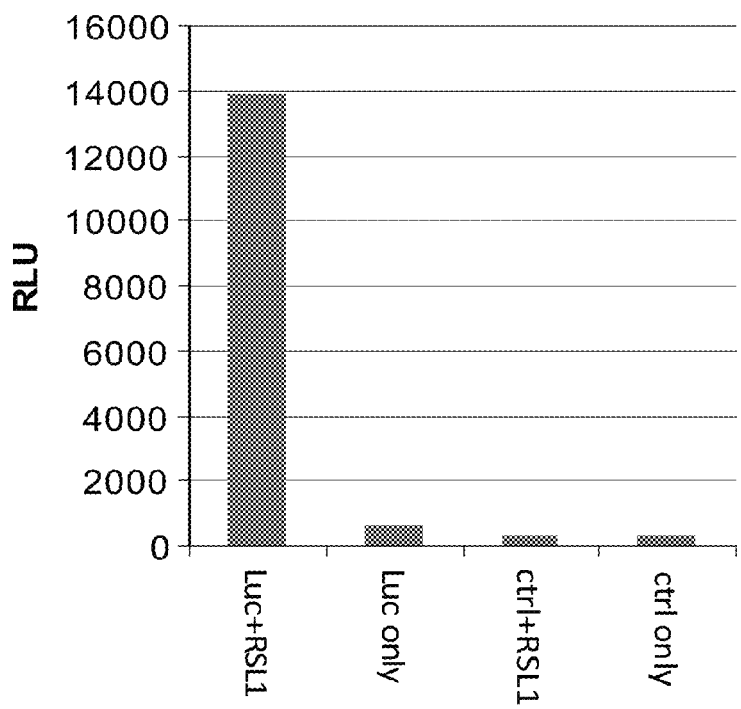
FIG. 12 reflects the effect of inhibiting RHGP-identified Robo1 on HIV infectivity. In Panel 11A, the ability to control activation of R1 through RSL1 is demonstrated. IN the lower panel, the impact of the presence of RSL1 on survival in the face of HIV challenge is presented.

A key feature of the RHGP technology is the ability to validate candidate targets via regulation by an inducible promoter. We first examined the inducible activity of transactivator R1 in the MT4-R1 cells that have been used to construct RHGP libraries. MT4-R1 cells were first transfected with an R1-responsive luciferase reporter gene (NEB) and cultured in the presence or absence of inducer RSL1. Luminescence (RLUs) was then examined MT4-R1 showed high and stable levels of luminescence in the presence of RSL1, but only background levels when RSL1 was not present (FIG. 12A). This result indicated that the activation ability of R1 is tightly controlled by RSL1.

Figure 12B:
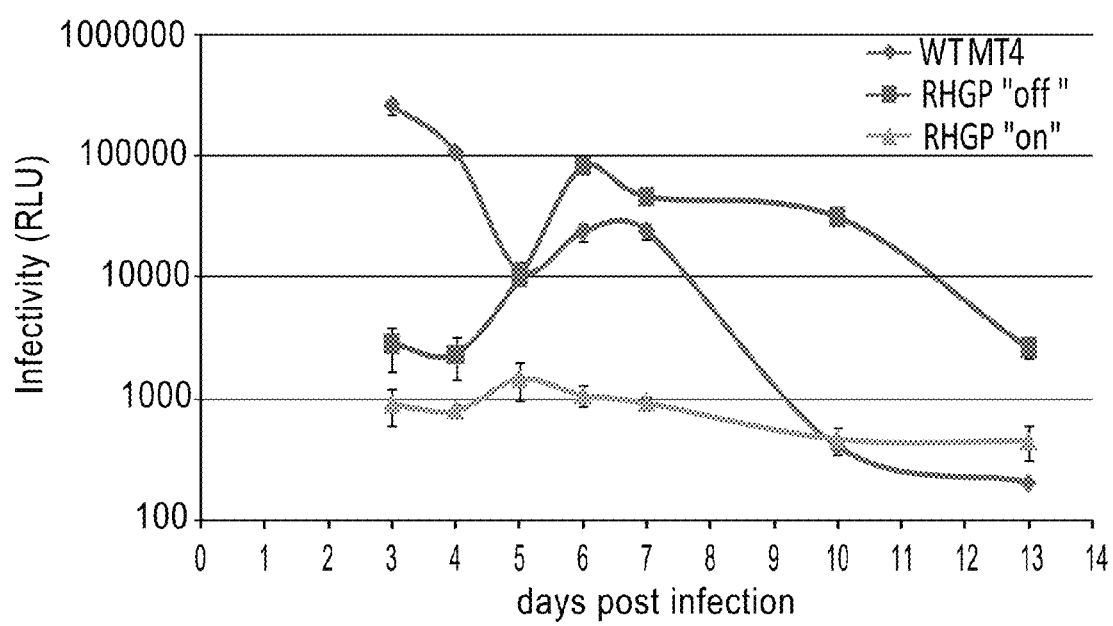
Figure 13:
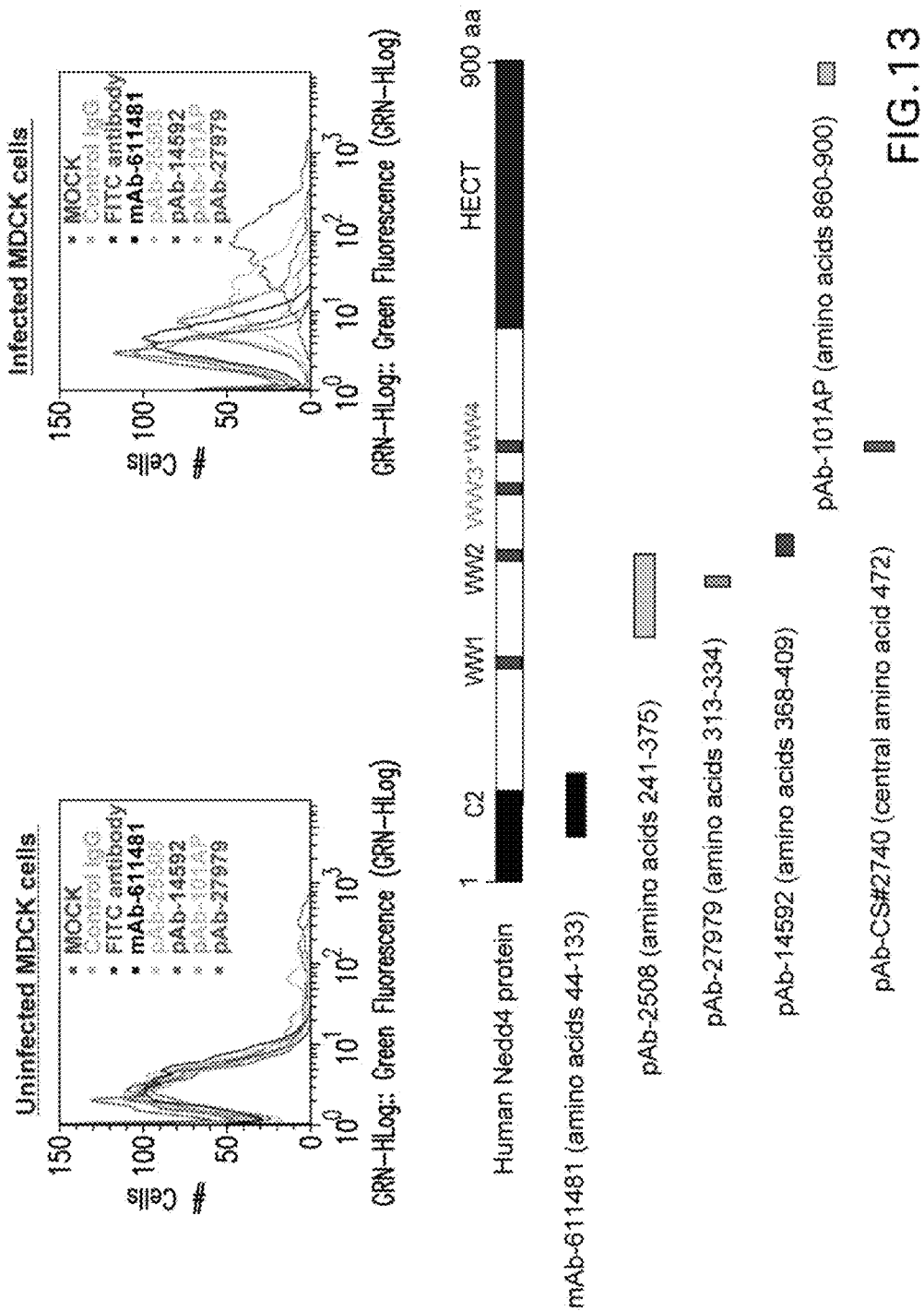
FIG. 13 depicts the generation of a variety of antibodies to Nedd4, the epitopes against which they were raised, and the identification of Nedd4 on the surface of infected MDCK cells.
Figure 14:
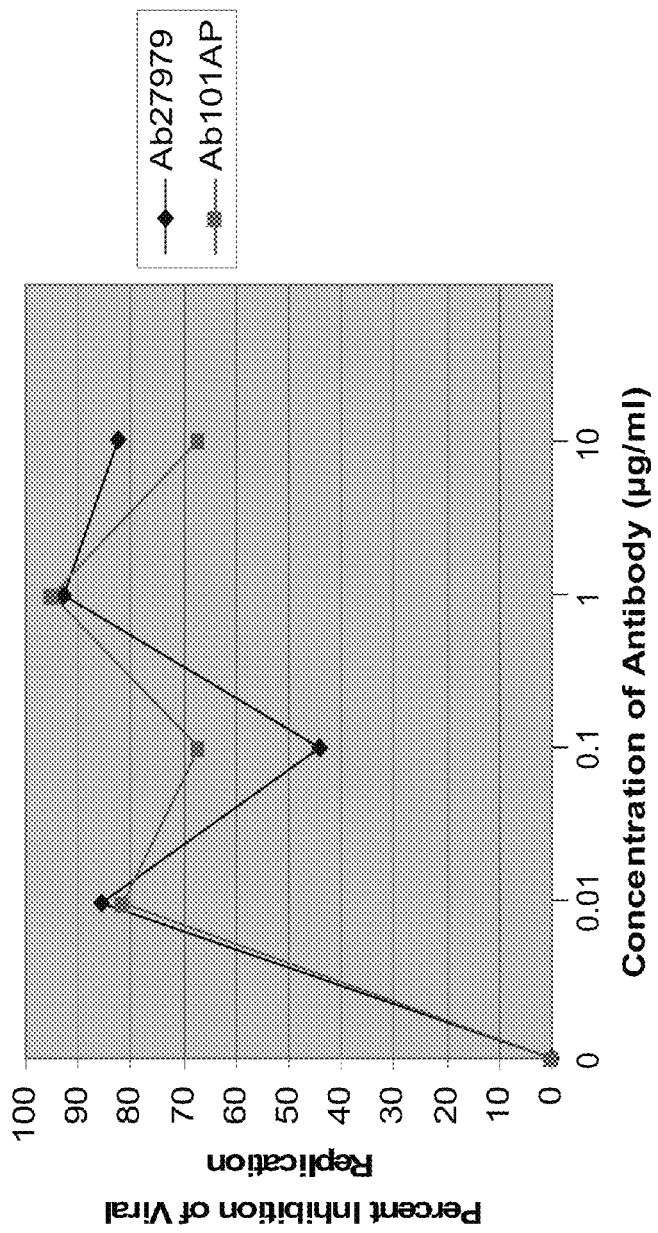
FIG. 14 is graph demonstrating the reduction of viral replication caused by Nedd4 antibodies.
Figure 15:
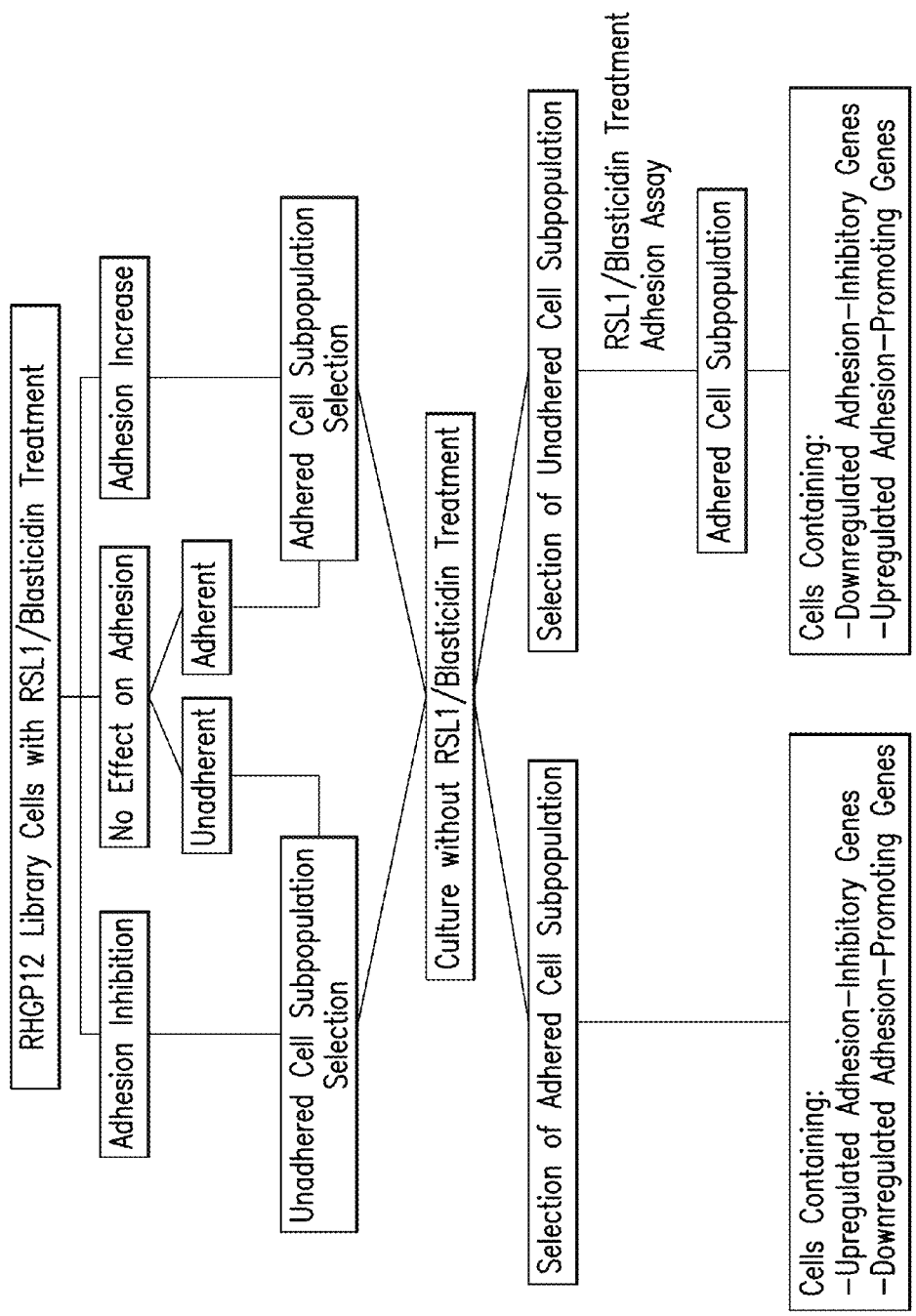
FIG. 15 is a flow chart illustrating the steps to take in the identification of targets for inhibiting cancer metastases using RHGP.

In order to confirm that acquirement of HIV-1 resistance on these clones was truly due to integration of RHGP, we then examined reversibility of viral production in these clones. Since the promoter for the RHGP vector was under control of the ligand controlled RheoSwitch Inducible transactivator R1, we could compare HIV-mediated killing of the candidates in the presence or absence of ligand RSL1. Our study confirmed that these surviving clones demonstrated reversible resistance to HIV-1 challenge. FIG. 12B shows the result of a representative cell clone from this series of experiments. When the ligand was absent in the cell culture during HIV-1 challenge, a robust viral production comparable to that produced from parental MT4 cells was observed for this cell clone. High levels of viral release persisted for many days until cells died from virus mediated killing.

Identification of the Host Gene by Genomic DNA Cloning

Genomic DNA was isolated from the viral resistant clones that had demonstrated reversible resistance to HIV-1. The 25 HIV-insensitive host cell clones with GSV integration sites yielded the identification of 21 distinct host cell targets. These GSV integrations included 12 previously-described genes and 2 non-annotated ESTs. Some of clones seemed were progeny from the same parent since the GSV had integrated in the same gene with the same orientation. Three clones had RHGP insertions in a region without genes or ESTs. We were unable to isolate candidate genes from 4 candidates due to partial loss of the Ori-CAT reporter gene.

The properties of these genes and ESTs are listed in Table 4. The site and orientation of integration offered by RHGP provided insight into the types of perturbations that allowed host cells to survive challenge with HIV-1. Specifically, the RHGP perturbations could be broadly divided into three groups: (1) "Antisense": Antisense integration events that facilitated disruption of one allele and antisense inhibition of the other allele; (2) "Sense Downstream": Integration in a sense orientation, which would be predicted to facilitate production of a dominant-negative inhibitor of the endogenous gene product; and (3) "Sense-Upstream": Integration in a sense orientation upstream of the start site, which would be predicted to facilitate over-expression of the target gene. Of the twelve (12) gene targets identified using RHGP, eight (8) targets represented "Antisense" knockdown of target expression. The other six (6) of the targets represented "Sense-Downstream" events, likely representing over-expression of dominant-negative inhibitors of wild-type gene expression. No "Sense-Upstream" insertions were identified in the current study. Based on these predictions, all of the candidate genes are likely downregulated by GSV integration event. This allowed us to directly use siRNA knock down approach on naive MT4 cells to recapitulate viral resistant phenotypes. Altogether, these findings suggest that RHGP-based interrogation of the host genome had identified both novel targets and/or ascribed novel functions to known genes.

Validation of Target Genes Using Naive Cells

RHGP identified a series of targets in MT4 cells that conferred resistance to HIV-1 infection and the reversibility of the phenotype provided an initial validation for these targets. We then sought to verify these candidates using an independent experimental system to exclude outcomes that might arise as spontaneous mutation or an artifact of our RHGP technology.

Duplex siRNAs targeting against these resistant genes were purchased from Dharmacon (Smartpool comprising of 4 individual siRNA). Non-targeting siRNAs provided a matched control for the transfection and reference standard. siRNA constructs specific for viral tat and a cellular target, Rab6A, were selected as positive controls based on recent reports that these siRNA were able to efficiently inhibit HIV-1 infection (Brass, Dykxhoorn et al. 2008).

siRNAs were transfected into naive MT4 cells via electroporation one day before HIV-1$_{NL4-3}$ infection. Supernatants were collected at day 2 post-infection. The infectious viral particles produced from treated cells were examined using TZM cell-based readouts. As indicated in FIG. 6A, duplex siRNAs against twelve (12) chosen target genes reduced HIV-1 virus production to levels comparable to those observed in the positive controls (Tat and Rab6A). Viability was also examined to exclude possible cytotoxic effects from siRNA treatment. Very similar percentages of viable cells were observed for all of the treated samples. These results confirmed our findings that these genes identified by RHGP are important in viral replication and validated the application of RHGP to identify novel host-based targets.

In order to examine whether these host gene candidates identified from cells survived from HIV-1$_{NL4-3}$ (a CXCR4-tropic virus) induced killing are also important to viral replication of an CCR5 tropic HIV-1 virus, the same siRNA approach was then used on CXCR4 and CCR5 dual expressing T cell line PM1 followed by infection with the R5-tropic HIV-1$_{ME1}$. Viral production of HIV-1$_{ME1}$ strain was significantly inhibited in the cells treated with specific siRNA targeting these twelve (12) gene targets (FIG. 6B). These results confirmed our findings that these genes identified by RHGP are important in replication of HIV-1 viruses including both X4 and R5 tropic variants and validated the application of RHGP to identify novel host-based targets.

In our present study we applied RHGP technology to conduct a genome-wide screen for host factors required for HIV-1 virus infection and we identified novel host-based targets that render cells resistant to an otherwise lethal challenge with HIV-1 virus. In addition, we ascribed novel anti-HIV-1 functions to previously-known genes and non-annotated ESTs. These targets were validated first using an inducible promoter incorporated within the RHGP vector to reverse the phenotype and then in naive cells using conventional siRNA approaches. We further found that the resultant targets were broadly applicable to different HIV variants, including drug sensitive and resistant isolates as well as CCR5 and CXCR4-tropic viruses.

Similar to the RHGP used in the earlier study which identified a panel of host target essential for survival in the face of an otherwise lethal influenza infection (Sui, Bamba et al. 2009), we used a lentiviral system to overcome the prior limitation of low titers of GSV production caused by MMLV based RHKO (Li and Cohen 1996). These improvements allowed us to sample the entire host genome and identify twelve (12) gene targets from the $10^5$ integration events invoked by the improved GSV. Consistent with prediction that a lentiviral vector favors single site insertion into sites of active gene transcription (Mitchell, Beitzel et al. 2004), all integration occurred in the active gene regions.

One unique feature of RHGP is that target expression is under control of an inducible promoter. Thus, the causal relationship between the phenotype (HIV-1 resistance) and the perturbed gene can be confirmed by withdrawal of the inducer. By validating these targets within the same experiment setting, this feature increases the efficiency of our discovery of therapeutic candidates. Indeed all the RHGP targets from resistant clones were successfully confirmed in the subsequent siRNA studies with naive cells. Depending on the location and direction of GSV insertion relative to a candidate gene, RHGP can also generate activation, often over-expression, of genes in mammalian cells. Although not observed in our current study, overexpression of a subset of targets including the B-cell CLL/lymphoma 2 (BCL2) allowed MDCK cells to survive influenza infection during discovery of host genes against influenza virus infection (Sui, Bamba et al. 2009). Instead of transient knock down effects generated by conventional approaches (e.g., siRNA), the RHGP phenotype is highly stable, which can facilitate mechanistic studies to characterize the roles of these perturbed genes in HIV-1 replication.

RHGP is not biased by prior knowledge of the target. Indeed from the HIV-1 resistant RHGP cell clones, we discovered 2 non-annotated ESTs were targeted by GSV (Table 1). Moreover, when we analyzed the gene targets using the PANTHER Classification System (Mi, Lazareva-Ulitsky et al. 2005), the putative molecular functions of many of them were still not classified (CASD1, GDAP2, TNRC6A, and TTC21B,) or unknown (CAMPSAP1L1 and GSTCD1). Two of them belong to Ubiquitin-protein ligase (HECW2 and DZIP3). In the remaining targets, one of each target is found in the following families: Immunoglobulin receptor or Defense/immunity protein (Robo1), signaling molecule (NLGN1), mRNA polyadenylation factor (CPSF1) and transporter or hydrolase (ATP8A1).

Among the candidate genes, Robo1 may serve as a very good therapeutic target. As a type I transmembrane protein it was originally identified as axon guidance receptor during neuronal development (Wong, Park et al. 2002). It was found that Robo1 also plays a role in T cell chemotaxis through interaction with CXCR4, a potential linkage with HIV infection (Wu, Feng et al. 2001; Prasad, Qamri et al. 2007). Whether it also binds CCR5 is worthwhile to examine. Using Western blot, we confirmed that Robo1 expression was reduced in the RHGP resistant clone and siRNA treated cells (unpublished data). Further investigation is needed to reveal that in Robo1-deficient CD4+ T cells viral replication is blocked in the viral entry step possibly during virion fusion of with cell membrane. Robo1 may possess potential new roles to support activity of HIV-1 coreceptor CCXR4 and CCR5 in HIV-1 replication. Similar to the therapeutic target of CCR5, antagonist and/or monoclonal antibody against Robo1 may therefore provide a new series of therapeutic regiment to treat AIDS. Applicants have caused to be deposited a monoclonal antibody to Robo1, accession number PTA-13191, at the American Type Culture Collection in Manassas, Va.

The list of identified HIV-1 resistant genes also includes two E3 ubiquitin ligases, HECW2 and DZIP3. Proteins from this family are found to be involved in protein sorting pathway and vesicular trafficking processes, which are also used by HIV-1 and other viruses during viral budding and release. One good example is TSG101, a ubiquitin-like ligases hijacked by HIV-1 Gag 6 for viral egress (Garrus, von Schwedler et al. 2001). HECW2 is highly homologous to another E3 ubiquitin ligase, NEDD4. While there is no direct evidence that HIV-1 viruses are using NEDD4, many other envelope viruses with a late domain of PPXY do require NEDD4 for their release from host cells. It is intriguing to speculate that these two gene products HECW2 and bZIP3 may be also important for HIV-1 maturation and egress.

TABLE 4

The property summary of identified HIV1 resistant host genes

| Target genes | Main known Function | Cellular Localization | C"# | Perturbation | siRNA validation |
| --- | --- | --- | --- | --- | --- |
| CASD1 CAS1 domain containing protein 1 precursor | O-acetyl-transferase | Multi-pass membrane Protein | 7 | Antisense intron 4 Downregulation | Yes |
| HECW2 HECT, C2 and WW domain-containing protein 2 | NEDD4 like E3 ubiquitf protein ligase 2 | Intracellular | 2 | Sense intron 15 ATG(sc) exon 7 Downregulation (DN) | Yes |
| ROBO1 roundabout protein homolog 1 | Axon guidance receptor and cell adhesion receptor | Type 1 membrane protein | 3 | Sense intron 2 ATG(sc) exon 1 Downregulation | Yes |
| NLGN1 member of the neuroligin family | Splice site specitif ligands for betaneurexins and may be involved in the formation and remodeling of central nervous system synapses | Neuronal cell surface | 3 | Antisense intron 3 Downregulation | Yes |
| DZIP3 (DAZ-interacting protein 3) | E3 Ubiquitin ligase proteins able to specifically bind RNA. Also called huRUL 138 (RNA-binding ubiquitin ligase of 138 kDa) | Intracellular | 3 | Antisense intron 1 Downregulation | Yes |
| CAMPSAP1L1 Calmodulin regulated spectrin-associated protein | Maybe involved in spectrin's function as a cytoskeletal protein providing a scaffolding and maintenance of plasma membrane | Membrane | 1 | Antisense intron 2 Downregulation | Yes |
| GSTCD1 gluathione S transferase (GST) C-terminal domain | A structural domain of GST, which conjugates reduced glutathione to a variety of targets to facilitate detoxification of the targets | Intracellular? | 4 | Antisense intron 5 Downregulation | Yes |
| CPSF1 Cleavage and polyadenylation specificity factor | It recognizes the AAUAAA signal in the RNA and facilitates both RNA cleavage amply a synthesis | Nucleus | 8 | Antisense intron 2 Downregulation | Yes |
| GDAP2 Ganglioside induced differentiation associated protein 2 | A signal transduction pathway during neuronal development | Intracellular | 1 | Sense last exon Downregulation (DN) | Yes |
| TNRC6A Trinucleotide repeat containing 6 protein | Post-transcriptional gene silencing through the RNA I and microRNA pathways. | Cytoplasmic bodies | 16 | Sense intron 4 ATG(sc) exon 1 Downregulation (DN) | Yes |

TABLE 4-continued

The property summary of identified HIV1 resistant host genes

| Target genes | Main known Function | Cellular Localization | C"# | Perturbation | siRNA validation |
|---|---|---|---|---|---|
| TTC21B Tetratricopeptide repeat domain 21B | May negatively modulate SH (Sonic Headgehog) signal transduction and may play a role in retrograde intraflagellar transport in cilia | Intracellular | 2 | Antisense intron 4 Downregulation | Yes |
| ATP8A1 Aminophospholipid transporter (APLT), Class 1, type 8A, member 1 | Transport of aminophospholipids from the outer to the inner leaflet of various membranes and the maintenance of asymmetric distribution of phospholipids, mainly in secretory vesicles | Membrane | 4 | Sense intron 4 ATG(sc) exon 1 Downregulation (DN) | Yes |
| Unknown ESTs | BE066906, AW817767, EB388641 AW300614 | | 3 2 | Sense Antisense | |

EXAMPLE 5

Further Investigation of Identified Potential Targets

The studies discussed above identified a novel host target that is essential for productive HIV infection—Robo1. Robo1 is a transmembrane receptor for soluble ligands known as SLITs. Robo1 is primarily expressed in the developing nervous system, where it regulates axon guidance. Robo1 is also expressed on lymphoid cells, where it similarly may play a role in regulating cell-cell interactions.

The extracellular structure of Robo1 is striking in that it consists of five stacked immunoglobulin (Ig) domains, which are supported by three tandem fibronectin type III (FN-III) domains. As such, Robo1 is predicted to extend relatively far out from the cell membrane. Such a property is often observed with cell-cell adhesion molecules since electrostatic repulsion of the negatively charged sugars on glycosylated proteins (glycoproteins and proteoglycans) serves as a barrier separating cells and preventing intimate interactions (such as membrane fusion). Indeed, we speculate that this mechanism might have evolved, in part, to prevent viruses from entering host cells.

We postulate that the extended projection of Robo1 from the cell membrane, in combination with the RHGP evidence for its essential role in viral infection, suggest that Robo1 might be involved in the uptake of virus, perhaps functioning as an initial site of virus-host binding or a co-receptor.

In support of this idea, Robo1 has been reported in the literature to interact with the chemokine receptor, CCR5. CCR5 in turn is known to function as a vital co-receptor for HIV infection. Indeed, CCR5 (as well as another chemokine receptor, CXCR4) are the targets of a series of recently approved or investigational new drugs to treat HIV infection.

As indicated in R J Shattock and J P Moore, *Nature Reviews Microbiology*, 1, 25; 2003, CCR5 does not protrude far from the cell membrane and it is postulated that CD4 binding to HIV-encoded gp120 provides the stability to overcome the well-understood electrostatic repulsion that would otherwise prevent HIV from coming into intimate contact with the T cell. This stability could then favor the subsequent interaction of CCR5 with viral proteins to mediate membrane fusion and internalization.

This model is interesting but it is important to recognize that the CD4 extracellular domain consists of 41 g-domains and thus CD4 is considerably shorter than Robo1. We therefore extend upon the existing models and postulate that Robo1 could function as an additional co-receptor, which is necessary for stabilizing an even earlier step of viral interaction than that mediated by CD4.

This hypothesis carries important potential implications for therapeutic interventions to prevent viral budding. For example, specific inhibitors of Robo1 or its viral binding partner could serve to prevent initial binding and/or prevent cell-cell spread of the infection. In experiments involving siRNA transfection to knock down HIV viral production, Robo1 knock-downs or gave out very low viral production values, leaving as low as 9% of the control value. Thus, inhibitors of Robo1 may effectively block spread of HIV-1 once cell initial cell infection occurs. These inhibitors could consist of, but are not necessarily limited to small molecules, aptamers and biologics (including antibodies, peptides and their derivatives).

At present, the viral binding partner for Robo1 is not known but we postulate different possibilities.

First, SLIT proteins (or other physiological ligands for Robo1) that are incorporated into the outer envelope of HIV particles as they bud from infected cells and these residual proteins could suffice to facilitate initial interactions with Robo1.

In addition or alternatively, Robo1 is understood to recognize a leucine-rich motif (LRR motif) encoded on its SLIT ligands. With this in mind, it is notable that HIV-encoded gp41 contains a relative prominence of leucine residues (16 of 123 residues; 13%); with localized regions that are particularly rich in these residues. The parent molecules of gp41 (gp160) contains 81 leucines (of 849 total residues; 9.5%). The other major protein encoded within gp160 is gp120, which contains 32 leucine residues (from a total of 455 residues; 7.0%) though there are prominent clusters of leucines in this molecule as well, at least one of which may resemble an LRR motif. HIV-encoded nef may also be exposed on the surface of virions and contains 17 leucine residues (from a total of 196 amino acids; 8.8%). This relative enrichment for leucines (and clusters) does not appear to represent a general trait of HIV since non-membrane exposed proteins such as reverse transcriptase utilize a small fraction of leucines (48 of 560; 8.5%), which are not so prominently clustered. Similarly HIV-1 Gag contains 41 leucines (of 508 total residues; 8.0%).

In addition to direct inhibition of viral attachment, flow cytometry data indicates that certain epitopes of Robo1 are preferentially exposed on the surface of HIV-infected cells. This finding raises the possibility for antibody-based targeting of infected cells for elimination via host-defense mechanisms (ADCC, CDC). In addition, these antibodies could be labeled with a toxin, radionuclide or other lethal agent to target infected cells. These types of activities would not necessarily be limited to antibodies as other antibodies, peptides, fusion proteins and biologics or small molecules that target these epitopes could also have activity for targeting infected cells.

Beyond HIV, recent data from Functional Genetics, Inc. suggests that certain epitopes on Robo1 are preferentially exposed on the surface of influenza-infected cells. This data could have implications for the broad-spectrum application of Robo1-based therapeutics. The mechanistic basis by which Robo1 is relevant to viruses beyond HIV are not known and the subject of current investigation.

To demonstrate the practical power of RHGP, certain of the targets identified in the Examples above were the subject of further investigation as potential host targets for therapeutic prevention or treatment of viral disease. In addition to Robo1 discussed immediately above, and PTCH1 discussed in the context of influenza above, Nedd4 was identified as above as a possible candidate for treatment of influenza. Nedd4 is also discussed in commonly owned U.S. patent application Ser. No. 11/939,122 filed Nov. 13, 2007, the entirety of which is incorporated herein by reference.

Nedd4 is a member of a class of proteins generally referred to as ESCRT proteins, and is typically found within the cell, where it interacts with other members of the ESCRT protein family to direct or carry proteins from one point to another within the cell. Antibodies to Nedd4 were prepared by standard measures. Although certain tissues of the human body do stain weakly for Nedd4 (e.g., colon, small intestine, liver hepatocytes) in general this protein is weakly expressed at the surface, if at all. Among the antibodies produced, Human Nedd4 antibodies Ab27979 and Ab101AP, both available from Functional Genetics, were prepared using conventional methods, but any antibody production method can be employed. FACS practiced with these and control antibodies raised against unrelated targets demonstrated that while Nedd4 stains not at all on the surface of MDCK cells that are not infected, MDCK cells infected with influenza (A/Udorn/72) exhibited large amounts of the protein on the surface. Like TSG101, it appears that as the viral apparatus takes over the cellular functions of the infected cell, Nedd4 is "hijacked" from its regular role and used to transport virions, or essential virion proteins, to the surface of the cell. FIG. 13.

Ab27979 (raised against an eptiope taken from the middle of the Nedd4 sequence, amino acids 313-334) and Ab101AP (raised against the c-terminus of the protein, Nedd4 amino acids 860-900)(See, FIG. 13) demonstrated strong ADCC mediated inhibition of influenza replication. At concentrations of 0.01 μg/ml and greater, these antibodies demonstrated better than 80% inhibition of viral replication in repeated in vitro experiments. (FIG. 14).

The experimental results discussed above were repeated against a variety of influenza strains, as one principal means of "escape" for influenza from conventional therapies is the introduction of small mutations, or new strains, that are sufficiently difference to avoid neutralization by the prior vaccine of treatment. Experiments demonstrated the antibody binding was persistent throughout the influenza strains compared, and related viruses (parainfluenza, RSV). The antibodies were used to demonstrate heavy staining on the surface by these antibodies against A/Udorn/72 (H3N2) using MDCK cells, A/Hong Kong/8/68 (H3N2) using MDCK cells, A/Japan/305/57 (H2N2) in HEK293 cells, A/Puerto Rico/8/34 (H1N1) in HEK293 cells, A/WSN/33 (H1N1) in HEK203 cells, B/Lee/40 in MDCK cells, HPIC-3 (human parainfluenza virus 3) in HEp-2 cells, CMV/AD-196 in MRC-5 cells and RSV/A2 in HEp-2 cells. These pan-viral results suggest that targeting human or mammalian (other mammals include pets and domesticated animals such as dogs, cats and related mammals and agricultural animals such as cows, sheep, pigs, goats, etc.) may be broadly effective, where conventional virus targeted treatments are commonly strain and host specific. Clearly, RHGP-TAIL technology provides the ability to rapidly identify genes and their encoded protein candidates for development as targets for intervention in a variety of situations.

EXAMPLE 6

RHGP Identification of Metastatic-Related Genes

As noted above, RHGP is not confined to identification of potential targets for the inhibition of viral infectivity. So long as a phenotype can be identified that is unique for the particular condition being considered, the use of RHGP gives a predictable result where the genes identified either promote or inhibit that phenotype. If the therapeutic agents are targeted at the protein encoded by the gene, as opposed to the gene itself, then the agent should give the corresponding effect.

Thus, one approach to improving cancer treatment is identifying agents that promote resistance to chemotherapy. Many potent chemotherapeutic agents are toxic to the host, a case of the cure being as bad as the disease. RHGP libraries are exposed to the chemotherapy agent. Those that survive the drug treatment are identified, and the genes whose perturbation caused the altered survival conditions, are selected, the orientation of the RHGP insert determined, as above, to determine whether over expression or reduced expression is responsible for the desired phenotype.

Survival is not the only characteristic that can be used as a phenotype in a RHGP search, however. In many cancers, it is development of the metastatic state that is particularly dangerous. Agents that could suppress the transformation of a tumor to a metastatic cancer would be of value in extending life and aiding support treatment. Tumors metastasize by emboli breaking off and entering the bloodstream. For effective metastases to form, the tumor emboli must bind to the endothelial wall of the blood vessel in which they have traveled. As shown by the flow chart in FIG. 15, RHGP can be used to interrogate perturbed cells for their ability to inhibit or promote adhesion. Therapeutic products which prevent a candidate targets ability to promote adhesion, such as antibodies which might bind the candidate, or products which enhance the reduction of adhesion, such as overexpression or administration of the candidates that inhibit adhesion, may similarly delay or suppress the formation of metastases.

Application of this RHGP investigation of adhesion phenotypes according to the flow chart of FIG. 15 has produced multiple candidates for investigation. The leading candidates are identified in FIG. 16, which reflects not only the identified candidate but whether it promotes or reduces adhesion, any identified utility or function, etc. Prosecution of each of these targets in turn may yield additional, well tolerated agents that are effective cancer treatment agents.

References cited throughout this patent application, and reated works, are listed below for better information.

Ataergin, S. A., Kindwall-Keller, T., Berger, N. A., and Lazarus, H. M. (2009). New generation pharmacotherapy in elderly multiple myeloma patients. *Expert Opinion on Pharmacotherapy* 10(1), 81-98.

Beckett, A. R., McKinney, S., Poon, S. S. S., Fee, J., and Aparicio, S. A. (2009). Identifying stromal-epithelial interactions in the mammary gland through genome-wide siRNA screening. *Cancer Research* 69(2), 85S-85S.

Campos, S. M. (2008). Anti-epidermal growth factor receptor strategies for advanced breast cancer. *Cancer Investigation* 26(8), 757-768.

Gottesman, M. M., and Ling, V. (2006). The molecular basis of multidrug resistance in cancer: The early years of P-glycoprotein research. *Febs Letters* 580(4), 998-1009.

Huesken, D., Lange, J., Mickanin, C., Weiler, J., Asselbergs, F., Warner, J., Meloon, B., Engel, S., Rosenberg, A., Cohen, D., Labow, M., Reinhardt, M., Natt, F., and Hall, J. (2005). Design of a genome-wide siRNA library using an artificial neural network. *Nature Biotechnology* 23(8), 995-1001.

Li, L., and Cohen, S. N. (1996). Tsg101: a novel tumor susceptibility gene isolated by controlled homozygous functional knockout of allelic loci in mammalian cells. *Cell* 85(3), 319-29.

Lih, C. J., Wei, W. S., and Cohen, S. N. (2006). Txr1: a transcriptional regulator of thrombospondin-1 that modulates cellular sensitivity to taxanes. *Genes & Development* 20(15), 2082-2095.

Liu, Y. G., Mitsukawa, N., Oosumi, T., and Whittier, R. F. (1995). Efficient Isolation and Mapping of *Arabidopsis-thaliana* T-DNA insert Junctions By Thermal Assymetric Interlaced PCR. *Plant Journal* 8(3), 457-463.

Madarnas, Y., Trudeau, M., Franek, J. A., McCready, D., Pritchard, K. I., and Messersmith, H. (2008). Adjuvant/neoadjuvant trastuzumab therapy in women with HER-2/neu-overexpressing breast cancer: A systematic review. *Cancer Treatment Reviews* 34(6), 539-557.

Pillai, M. M., Venkataraman, G. M., Kosak, S., and Torok-Storb, B. (2008). Integration site analysis in transgenic mice by thermal asymmetric interlaced (TAIL)-PCR: segregating multiple-integrant founder lines and determining zygosity. *Transgenic Research* 17(4), 749-754.

Pytel, D., Sliwinski, T., Poplawski, T., Ferriola, D., and Majsterek, I. (2009). Tyrosine Kinase Blockers: New Hope for Successful Cancer Therapy. *Anti-Cancer Agents in Medicinal Chemistry* 9(1), 66-76.

Reiske, H., Sui, B., Ung, H., Donahue, R., Li, W.-L., Goldblatt, M., Li, L., and Kinch, M. S. (2009). Identification of Annexin A13 as a Regulator of Chemotherapy Resistance Using Random Homozygous Gene Perturbation. *Analytical Quantitative Cytology Histology* In Press.

Yang, Y. L., Kitagaki, J., Wang, H., Hou, D. X., and Perantoni, A. O. (2009).

MMWR Jun. 27, 2008, 57 (25); 692-69.

MMWR April 2008, 57(15): 393-8.

Luscher-Mattli, M. (2000) *Arch. Virol.* 145, 2233-2248.

Tan, S.-L., Gnji, G. G., Paeper, P., Proll, S. & Katze, M. G. System biology and the host response to viral infection. *Nat. Biotechnol.* 25, 1383-1389 (2007).

Fox, J. L. Antivirals become a broader enterprise. *Nat. Biotechnol.* 25, 1395-1402 (2007).

Wheeler, J., McHale, M., Jackson, V. & Penny, M. Assessing theoretical risk and benefit suggested by genetic association studies of CCR5: experience in a drug development programme for maraviroc. *Antivir. Ther.* 12, 233-245 (2007).

Poli, G. IDrugs 2001, 4:1068-1071.

Lombardo, A., Genovese, P., Beausejour, C. M., Colleoni, S., Lee, Y-L., Kim, K. A., Ando, D., Urnov, F. D., Galli, C., Gregory, P. D., Holmes, M. C. and Naldini, L. *Nature Biotechnology* 25, 1298-1306 (2007).

Lamb, R A; Krug, R M. Orthomyxoviridae: The Viruses and Their Replication. In: Knipe D M, Howley P M., editors. *Fields Virology.* Lippincott, Williams & Wilkins; Philadelphia: 2001. pp. 1487-532.

Ludwig, S., Pleschka, S, and Wolff, T. A fatal relationship—influenza virus interactions with the host cell. *Viral Immunol.* 1999; 12:175-196.

Ahlquist, P., Noueiry, A. O., Lee, W. M., Kushner, D. B. & Dye, B. T. (2003) *J. Virol.* 77, 8181-8186.

Hao, L., Sakurai, A., Watanabe, T., Sorensen, E., Nidom, C. A., Newton, M. A., Ahlquist, P. and Kawaoka, Y. *Drosophila* RNAi screen identifies host genes important for influenza virus replication. Nature (2008).

Brass, A. L., Dykxhoorn, D. M., Benita, Y., Yan, N., Engelman, A., Xavier, R. J., Lieberman, J., and Elledge, S. J. (2008). Identification of host proteins required for HIV infection through a functional genomic screen. Science 319, 817-824.

Konig et al. Global Analysis of Host-Pathogen Interactions that Regulate Early-Stage HIV-1 Replication. Cell 135:49-60, 2008.

Krishnam, M. N., et al. RNA interference screen for human genes associated with West Nile virus infection. Nature (2008).

Li, L. and Cohen, S. N. (1996) "Tsg101: A novel tumor susceptibility gene isolated by controlled homozygous functional knockout of allelic loci in mammalian cells" Cell 85 (3):319-29.

Lu, Q. Wei, W. Kowalski, P. E. Chang, A. C. Y. and Cohen, S. N. EST-based genome-wide gene inactivation identifies ARAP3 as a host protein affecting cellular susceptibility to anthrax toxin. Proc. Natl. Acad. Sci. USA 101, 17246-17251 (2004)

Ge, Q. et al. RNA interference of influenza virus production by directly targeting mRNA for degradation and indirectly inhibiting all viral RNA transcription. Proc. Natl Acad. Sci. USA 100, 2718-2723 (2003).

Gupta, P. K. and Varshney, R. K., Ed. (eds) Cereal Genomics, Kluwer Academic publishers, 2004. p. 386.

Mitchell R S, Beitzel B F, Schroder A R W, Shinn P, Chen H, et al. (2004) Retroviral DNA integration: ASLV, HIV, and MLV show distinct target site preferences. PLoS Biol 2(8): e234.

Mi, H. et al. The PANTHER database of protein families, subfamilies, functions and pathways. Nucleic Acids Res. 33, D284D288 (2005).

Ndolo, E., George, M., Nguyen, H. and Dandekar, S. (2006) Virology 353, 374-387.

Baldwin, B., M. Kleinberg and S. Keay, 1996 Molecular cloning and expression of receptor peptides that block human cytomegalovirus/cell fusion. Biochem. Biophys. Res. Commun 219: 668-673.

Howell, G. R. Shindo, M. Murry, S. Gridley, T. Wilson, L. A. and Schimenti, J. C. Mutation of a Ubiquitously Expressed Mouse Transmembrane Protein (Tapt1) Causes Specific Skeletal Homeotic Transformations. Genetics 175:699-707 (2007)

Levine, B., Q. Huang, J. T. Issacs, J. C. Reed, D. E. Griffin, and J. M. Hardwick. 1993. Conversion of lytic to persistent alphavirusinfection by the bcl-2 cellular oncogene. Nature (London) 361:739-742.

Hinshaw, V. S., Olsen, C. W., Dybdahl-Sissoko, N. & Evans, D. Apoptosis: a mechanismof cell killing by influenzaAand B viruses. J. Virol. 68, 3667-3673 (1994).

Mishra S, Mishra J P, Kumar A. Activation of JNK-dependent pathway is required for HIV viral protein R-induced apoptosis in human monocytic cells: involvement of antiapoptotic BCL2 and c-IAP1 genes. *J Biol. Chem.* 2007 Feb. 16; 282(7):4288-300.

Wada M, Wada N A, Shirono H, Taniguchi K, Tsuchie H, Koga *J. Biochem Biophys Res Commun* 2001 Jun. 8; 284 (2):346-51.

Martinez, I., Lombardia, L., Blanca Garcia-Barreno, B. G., Dominguez, O. And Melero, J. A. Distinct gene subsets are induced at different time points after human respiratory syncytial virus infection of A549 cells. *J Gen Virol* 88 (2007), 570-581.

Ahlquist, P., Noueiry, A. O., Lee, W. M., Kushner, D. B., and Dye, B. T. (2003). Host factors in positive-strand RNA virus genome replication. *Journal of Virology* 77(15), 8181-8186.

Baldwin, B. R., Kleinberg, M., and Keay, S. (1996). Molecular cloning and expression of receptor peptides that block human cytomegalovirus cell fusion. *Biochemical and Biophysical Research Communications* 219(2), 668-673.

Belongia, E., Kieke, B., Coleman, L., Donahue, J., Irving, S., Meece, J., Vandermause, M., Shay, D., Gargiullo, P., Balish, A., Foust, A., Guo, L., Lindstrom, S., Xu, X., Klimov, A., Bresee, J., and Cox, N. (2008). Interim within-season estimate of the effectiveness of trivalent inactivated influenza vaccine—Marshfield, Wis., 2007-08 influenza season (Reprinted from vol 57, pg 393-398, 2008). *Jama-Journal of the American Medical Association* 299(20), 2381-2384.

Brass, A. L., Dykxhoorn, D. M., Benita, Y., Yan, N., Engelman, A., Xavier, R. J., Lieberman, J., and Elledge, S. J. (2008). Identification of host proteins required for HIV infection through a functional genomic screen. *Science* 319(5865), 921-926.

Chen, B. J., and Lamb, R. A. (2008). Mechanisms for enveloped virus budding: Can some viruses do without an ESCRT? *Virology* 372(2), 221-232.

Fox, J. L. (2007). Antivirals become a broader enterprise. Nature Biotechnology 25(12), 1395-1402.

Ge, Q., McManus, M. T., Nguyen, T., Shen, C. H., Sharp, P. A., Eisen, H. N., and Chen, J. Z. (2003). RNA interference of influenza virus production by directly targeting mRNA for degradation and indirectly inhibiting all viral RNA transcription. *Proceedings of the National Academy of Sciences of the United States of America* 100(5), 2718-2723.

Gupta, P. K., and Varshney, R. K. (2004). Cereal genomics: An overview. *Cereal Genomics*, 1-18.

Hao, L. H., Sakurai, A., Watanabe, T., Sørensen, E., Nidom, C. A., Newton, M. A., Ahlquist, P., and Kawaoka, Y. (2008). *Drosophila* RNAi screen identifies host genes important for influenza virus replication. *Nature* 454(7206), 890-U46.

Hinshaw, V. S., Olsen, C. W., Dybdahlsissoko, N., and Evans, D. (1994). Apoptosis—A Mechanism of Cell-Killing By Influenza-A and INfluenza-B Viruses *Journal of Virology* 68(6), 3667-3673.

Howell, G. R., Shindo, M., Murray, S., Gridley, T., Wilson, L. A., and Schimenti, J. C. (2007). Mutation of a ubiquitously expressed mouse transmembrane Protein (Tapt1) causes specific skeletal homeotic transformations. Genetics 175 (2), 699-707.

Kleinman, M. E., Yamada, K., Takeda, A., Chandrasekaran, V., Nozaki, M., Baffi, J. Z., Albuquerque, R. J. C., Yamasaki, S., Itaya, M., Pan, Y. Z., Appukuttan, B., Gibbs, D., Yang, Z. L., Kariko, K., Ambati, B. K., Wilgus, T. A., DiPietro, L. A., Sakurai, E., Zhang, K., Smith, J. R., Taylor, E. W., and Ambati, J. (2008). Sequence- and target-independent angiogenesis suppression by siRNA via TLR3. *Nature* 452(7187), 591-U1.

Konig, R., Zhou, Y. Y., Elleder, D., Diamond, T. L., Bonamy, G. M. C., Irelan, J. T., Chiang, C. Y., Tu, B. P., De Jesus, P. D., Lilley, C. E., Seidel, S., Opaluch, A. M., Caldwell, J. S., Weitzman, M. D., Kuhen, K. L., Bandyopadhyay, S., Ideker, T., Orth, A. P., Miraglia, L. J., Bushman, F. D., Young, J. A., and Chanda, S. K. (2008). Global analysis of host-pathogen interactions that regulate early-stage HIV-1 replication. *Cell* 135(1), 49-60.

Krishnan, M. N., Ng, A., Sukumaran, B., Gilfoy, F. D., Uchil, P. D., Sultana, H., Brass, A. L., Adametz, R., Tsui, M., Qian, F., Montgomery, R. R., Lev, S., Mason, P. W., Koski, R. A., Elledge, S. J., Xavier, R. J., Agaisse, H., and Fikrig, E. (2008). RNA interference screen for human genes associated with West Nile virus infection. *Nature* 455(7210), 242-U67.

Lamb, R. A., and Takeda, M. (2001). Death by influenza virus protein. *Nature Medicine* 7(12), 1286-1288.

Levine, B., Huang, Q., Isaacs, J. T., Reed, J. C., Griffin, D. E., and Hardwick, J. M. (1993). CONVERSION OF LYTIC TO PERSISTENT ALPHAVIRUS INFECTION BY THE BCL-2 CELLULAR ONCOGENE. *Nature* 361(6414), 739-742.

Li, L., and Cohen, S. N. (1996). Tsg101: a novel tumor susceptibility gene isolated by controlled homozygous functional knockout of allelic loci in mammalian cells. *Cell* 85(3), 319-29.

Lu, Q., Wei, W. S., Kowalski, P. E., Chang, A. C. Y., and Cohen, S. N. (2004). EST-based genome-wide gene inactivation identifies ARAP3 as a host protein affecting cellular susceptibility to anthrax toxin. *Proceedings of the National Academy of Sciences of the United States of America* 101(49), 17246-17251.

Ludwig, S., Pleschka, S., and Wolff, T. (1999). A fatal relationship—Influenza virus interactions with the host cell. *Viral Immunology* 12(3), 175-196.

Luscher-Mattli, M. (2000). Influenza chemotherapy: a review of the present state of art and of new drugs in development. *Archives of Virology* 145(11), 2233-2248.

Martinez, I., Lombardia, L., Garcia-Barreno, B., Dominguez, O., and Melero, J. A. (2007). Distinct gene subsets are induced at different time points after human respiratory syncytial virus infection of A549 cells. *Journal of General Virology* 88, 570-581.

Mi, H. Y., Lazareva-Ulitsky, B., Loo, R., Kejariwal, A., Vandergriff, J., Rabkin, S., Guo, N., Muruganujan, A., Doremieux, O., Campbell, M. J., Kitano, H., and Thomas, P. D. (2005). The PANTHER database of protein families, subfamilies, functions and pathways. *Nucleic Acids Research* 33, D284-D288.

Mishra, S., Mishra, J. P., and Kumar, A. (2007). Activation of JNK-dependent pathway is required for HIV viral protein R-induced apoptosis in human monocytic cells—Involvement of antiapoptotic BCL2 and c-IAP1 genes. *Journal of Biological Chemistry* 282(7), 4288-4300.

Mitchell, R. S., Beitzel, B. F., Schroder, A. R. W., Shinn, P., Chen, H. M., Berry, C. C., Ecker, J. R., and Bushman, F. D. (2004). Retroviral DNA integration: ASLV, HIV, and MLV show distinct target site preferences. *Plos Biology* 2(8), 1127-1137.

Ndolo, T., George, M., Nguyen, H., and Dandekar, S. (2006). Expression of simian immunodeficiency virus Nef protein in CD4(+) T cells leads to a molecular profile of viral persistence and immune evasion. *Virology* 353(2), 374-387.

Ong, A. K., and Hayden, F. G. (2007). John F Enders lecture 2006: Antivirals for influenza. *Journal of Infectious Diseases* 196(2), 181-190.

Reeves, J. D., and Piefer, A. J. (2005). Emerging drug targets for antiretroviral therapy. *Drugs* 65(13), 1747-66.

Tan, S. L., Ganji, G., Paeper, B., Proll, S., and Katze, M. G. (2007). Systems biology and the host response to viral infection. *Nature Biotechnology* 25(12), 1383-1389.

Thompson, W. W., Shay, D. K., Weintraub, E., Brammer, L., Cox, N., Anderson, L. J., and Fukuda, K. (2003). Mortality associated with influenza and respiratory syncytial virus in the United States. *Jama-Journal of the American Medical Association* 289(2), 179-186.

Wada, M., Wada, N. A., Shirono, H., Taniguchi, K., Tsuchie, H., and Koga, J. (2001) Amino-terminal fragment of urokinase-type plasminogen activator inhibits HIV-1 replication. *Biochemical and Biophysical Research Communications* 284(2), 346-351.

Wheeler, J., McHale, M., Jackson, V., and Penny, M. (2007). Assessing theoretical risk and benefit suggested by genetic association studies of CCR5: experience in a drug development programme for maraviroc. *Antiviral Therapy* 12(2), 233-245.

Garrus, J. E., U. K. von Schwedler, et al. (2001). "Tsg101 and the vacuolar protein sorting pathway are essential for HIV-1 budding." *Cell* 107(1): 55-65.

Grant, R. M., F. M. Hecht, et al. (2002). "Time trends in primary HIV-1 drug resistance among recently infected persons." *JAMA* 288(2): 181-8.

Gupta, P. K. and R. K. Varshney (2004). "Cereal genomics: An overview." *Cereal Genomics*: 1-18.

Kleinman, M. E., K. Yamada, et al. (2008). "Sequence- and target-independent angiogenesis suppression by siRNA via TLR3." *Nature* 452(7187): 591-U1.

Konig, R., Y. Y. Zhou, et al. (2008). "Global analysis of host-pathogen interactions that regulate early-stage HIV-1 replication." *Cell* 135(1): 49-60.

Li, L. and S. N. Cohen (1996). "Tsg101: a novel tumor susceptibility gene isolated by controlled homozygous functional knockout of allelic loci in mammalian cells." *Cell* 85(3): 319-29.

Liu, R., W. A. Paxton, et al. (1996). "Homozygous defect in HIV-1 coreceptor accounts for resistance of some multiply-exposed individuals to HIV-1 infection." *Cell* 86(3): 367-77.

Lu, Q., W. S. Wei, et al. (2004). "EST-based genome-wide gene inactivation identifies ARAP3 as a host protein affecting cellular susceptibility to anthrax toxin." *Proceedings of the National Academy of Sciences of the United States of America* 101(49): 17246-17251.

Mi, H. Y., B. Lazareva-Ulitsky, et al. (2005). "The PANTHER database of protein families, subfamilies, functions and pathways." *Nucleic Acids Research* 33: D284-D288.

Mitchell, R. S., B. F. Beitzel, et al. (2004). "Retroviral DNA integration: ASLV, HIV, and MLV show distinct target site preferences." *Plos Biology* 2(8): 1127-1137.

Prasad, A., Z. Qamri, et al. (2007). "Slit-2/Robo-1 modulates the CXCL12/CXCR4-induced chemotaxis of T cells." *J Leukoc Biol* 82(3): 465-76.

Reeves, J. D. and A. J. Piefer (2005). "Emerging drug targets for antiretroviral therapy." *Drugs* 65(13): 1747-66.

Richman, D. D., S. C. Morton, et al. (2004). "The prevalence of antiretroviral drug resistance in the United States." *AIDS* 18(10): 1393-401.

Sui, B., D. Bamba, et al. (2009). "The use of Random Homozygous Gene Perturbation to identify novel host-oriented targets for influenza." *Virology*.

Wei, X. P., J. M. Decker, et al. (2002). "Emergence of resistant human immunodeficiency virus type 1 in patients receiving fusion inhibitor (T-20) monotherapy." *Antimicrobial Agents and Chemotherapy* 46(6): 1896-1905.

Wheeler, J., M. McHale, et al. (2007). "Assessing theoretical risk and benefit suggested by genetic association studies of CCR5: experience in a drug development programme for maraviroc." *Antiviral Therapy* 12(2): 233-245.

Wong, K., H. T. Park, et al. (2002). "Slit proteins: molecular guidance cues for cells ranging from neurons to leukocytes." *Curr Opin Genet Dev* 12(5): 583-91.

Wu, J. Y., L. Feng, et al. (2001). "The neuronal repellent Slit inhibits leukocyte chemotaxis induced by chemotactic factors." *Nature* 410(6831): 948-52.

The invention disclosed in this application has been exemplified by multiple specific examples as well as generically discussed. The examples, including specific vector fragments, targets and procedures, are not intended to be limiting. In the absence of specific recitations found in the claims, the claims should not be considered to be limited to any exemplified embodiment, and should be read consistent with all aspects of the disclosure.

What is claimed is:

1. A method of inhibiting the infectivity of HIV in mammalian cells, comprising:
   selecting mammalian cells in need of inhibition of HIV infectivity and contacting said cells with an effective amount of an antibody that binds preferentially to Robo1 protein.

2. The method of claim 1, wherein said selecting is accomplished by selecting a mammal in need of reducing the infectivity of HIV and said contacting is achieved by administering said antibody to said mammal.

3. The method of claim 1, wherein said method comprises administering to said mammal a Robo 1 protein which induces said mammal to produce antibodies which bind preferentially to Robo1 protein, thereby contacting cells of said mammal with said antibodies produced.

4. The method of claim 2, wherein said antibody is a monoclonal antibody.

* * * * *